(12) United States Patent
Kelly et al.

(10) Patent No.: US 11,168,145 B2
(45) Date of Patent: Nov. 9, 2021

(54) PLECTIN-1 BINDING ANTIBODIES AND USES THEREOF

(71) Applicant: ZIELBIO, INC., Charlottesville, VA (US)

(72) Inventors: Kimberly A. Kelly, Goochland, VA (US); Julien Dimastromatteo, Charlottesville, VA (US)

(73) Assignee: ZIELBIO, INC., Charlottesville, VA (US)

( * ) Notice: Subject to any disclaimer, the term of this patent is extended or adjusted under 35 U.S.C. 154(b) by 101 days.

(21) Appl. No.: 16/091,928

(22) PCT Filed: Apr. 7, 2017

(86) PCT No.: PCT/US2017/026711
§ 371 (c)(1),
(2) Date: Oct. 5, 2018

(87) PCT Pub. No.: WO2017/177199
PCT Pub. Date: Oct. 12, 2017

(65) Prior Publication Data
US 2019/0119397 A1 Apr. 25, 2019

Related U.S. Application Data

(60) Provisional application No. 62/320,117, filed on Apr. 8, 2016.

(51) Int. Cl.
| | | |
|---|---|---|
| *C07K 16/30* | (2006.01) | |
| *C07K 16/18* | (2006.01) | |
| *A61K 47/69* | (2017.01) | |
| *A61K 47/68* | (2017.01) | |
| *A61K 35/00* | (2006.01) | |
| *A61K 49/00* | (2006.01) | |

(52) U.S. Cl.
CPC ............ *C07K 16/30* (2013.01); *A61K 35/00* (2013.01); *A61K 47/6803* (2017.08); *A61K 47/6849* (2017.08); *A61K 47/6929* (2017.08); *A61K 49/0002* (2013.01); *C07K 16/18* (2013.01); *C07K 2317/33* (2013.01); *C07K 2317/73* (2013.01); *C07K 2317/77* (2013.01); *C07K 2317/92* (2013.01)

(58) Field of Classification Search
CPC .............. C07K 16/30; A61K 47/6929; A61K 47/6803; A61K 47/6849; A61K 35/00
See application file for complete search history.

(56) References Cited

U.S. PATENT DOCUMENTS

| | | |
|---|---|---|
| 2003/0118592 A1 | 6/2003 | Ledbetter et al. |
| 2004/0101874 A1 | 5/2004 | Ghosh et al. |
| 2005/0164324 A1* | 7/2005 | Gygi .................. G01N 33/6842 435/23 |
| 2009/0186031 A1 | 7/2009 | Wood et al. |
| 2010/0279932 A1 | 11/2010 | Ledbetter et al. |
| 2011/0271357 A1* | 11/2011 | Kim .................. A61P 35/00 800/13 |
| 2015/0151010 A1* | 6/2015 | Kelly .................. A61K 38/08 424/1.69 |
| 2015/0299334 A1 | 10/2015 | Bamdad |
| 2016/0137725 A1* | 5/2016 | Gu .................. G01N 33/543 436/501 |
| 2017/0087257 A1 | 3/2017 | Kelly et al. |
| 2017/0267719 A1 | 9/2017 | Madamsetty et al. |
| 2020/0268900 A1 | 8/2020 | Kelly |

FOREIGN PATENT DOCUMENTS

| | | |
|---|---|---|
| WO | WO 2009/036092 A2 | 3/2009 |
| WO | WO 2017/177199 A2 | 10/2017 |
| WO | WO 2019/075216 A1 | 4/2019 |

OTHER PUBLICATIONS

International Search Report and Written Opinion dated Sep. 22, 2017 for International Application No. PCT/US2017/026711, 13 pages.
International Search Report and Written Opinion dated Jan. 24, 2019 for International Application No. PCT/US2018/055438, 15 pages.
Abcam Product Datasheet, "Immunogen: A recombinant fragment comprising the C-terminal 220 amino acids of plectin," Jan. 19, 2015; retrieved from http://www.abcam.com/plectin-antibody-e398p-ab32528.html; 6 pages.
Aho, S. et al., "Plectin Serves as an Autoantigen in Paraneoplastic Pemphigus," The Journal of Investigative Dermatology, 113(3):422-423 (1999).
Antonow, D. & Thurston, D. E., "Synthesis of DNA-Interactive Pyroolo[2,1-c][1,4]benzodiazepines (PBDs)," Chem. Rev., 111:2815-2864 (2011).
Brentnall, T. A. et al., "Early Diagnosis and Treatment of Pancreatic Dysplasia in Patients with a Family History of Pancreatic Cancer," Ann Intern. Med., 131:247-255 (1999).
Canto, M. I. et al., "Screening for Pancreatic Neoplasia in High-Risk Individuals: An EUS-Based Approach," Clinical Gastroenterolgoy and Hepatology, 2:606-621 (2004).
Cheng, C.-C. et al., "Plectin deficiency in liver cancer cells promotes cell migration and sensitivity to sorafenib treatment," Cell Ahesion & Migration, 12(1):19-27 (2018).
Cipolla, L. et al., "Pyrrolo[2,1-c][1,4]benzodiazepine as a Scaffold for the Design and Synthesis of Anti-Tumour Drugs," Anti-Cancer Agents in Medicinal Chemistry, 9:1-31 (2009).
Gerratana, B., "Biosynthesis, Synthesis, and Biological Activities of Pyrrolobenzodiazepines," Med Res Rev, 32(2):254-293 (2012).

(Continued)

*Primary Examiner* — Lei Yao
(74) *Attorney, Agent, or Firm* — Cooley LLP

(57) ABSTRACT

Aspects of the disclosure provide compositions and methods for treating cancer characterized by surface expression of plectin-1. In some embodiments, the disclosure provides anti-plectin-1 antibodies. In some embodiments, the anti-plectin-1 antibodies are conjugated to a targeted moiety (e.g., a therapeutic moiety or a detectable label).

10 Claims, 10 Drawing Sheets
Specification includes a Sequence Listing.

(56) References Cited

OTHER PUBLICATIONS

Goggins, M. "Molecular Markers of Early Pancreatic Cancer," J Clin Oncol, 23:4524-4531 (2005).
Köhler, G. & Milstein, C., "Continuous cultures of fused cells secreting antibody of predefined specificity," Nature, 256:495-497 (1975).
Li, D. et al., "Pancreatic Cancer," Lancet, 363:1049-1057 (2004).
Pelaez-Luna, M. et al., "Resectability of Presymptomatic Pancreatic Cancer and Its Relationship to Onset of Diabetes: A Retrospective Review of CT Scans and Fasting Glucose Values Prior to Diagnosis," Am J Gastroenterol, 102:2157-2163 (2007).
Proby, C. et al., "Human Autoantibodies against HD1/Plectin in Paraneoplastic Pemphigus," J Invest Dermatol, 112:153-156 (1999).
Rikardsen, O. G. et al., "Plectin as a prognostic marker in non-metastatic oral squamous cell carcinoma," BMC Oral Heatlh, 15:98 (2015), 9 pages; doi:10.1186/s12903-015-0084-9.
Shin, S. J. et al., "Unexpected gain of function for the scaffolding protein plectin due to mislocalization in pancreatic cancer," PNAS, 110(48):19414-19419 (2013).
Sonnenberg, A. & Liem, R. K. H., "Plakins in development and disease," Experimental Cell Research, 313:2189-2203 (2007).
UniProtKB—Q15149, Oct. 14, 2008, http://www.uniprot.org/uniprot/Q15149, 19 pages.
Wayback Machine, https://web.archive.org/web/*/http://www.abcam.com/plectin-antibody-e398p-ab32528.html, Aug. 25, 2017, used to establish Abcam Product Databsheet, 3 pages.
Yeo, C. J. et al., "A prospective randomized trial of pancreaticogastrostomy versus pancreaticojejunostomy after pancreaticoduodenectomy," Annals of Surgery, 222(4):580-592 (1995).

* cited by examiner

SEQUENCE LISTING

<160> NUMBER OF SEQ ID NOS: 93

<210> SEQ ID NO 1
<211> LENGTH: 4684
<212> TYPE: PRT
<213> ORGANISM: Homo sapiens

<400> SEQUENCE: 1

```
Met Val Ala Gly Met Leu Met Pro Arg Asp Gln Leu Arg Ala Ile Tyr
1               5                   10                  15

Glu Val Leu Phe Arg Glu Gly Val Met Val Ala Lys Lys Asp Arg Arg
                20                  25                  30

Pro Arg Ser Leu His Pro His Val Pro Gly Val Thr Asn Leu Gln Val
            35                  40                  45

Met Arg Ala Met Ala Ser Leu Arg Ala Arg Gly Leu Val Arg Glu Thr
    50                  55                  60

Phe Ala Trp Cys His Phe Tyr Trp Tyr Leu Thr Asn Glu Gly Ile Ala
65                  70                  75                  80

His Leu Arg Gln Tyr Leu His Leu Pro Pro Glu Ile Val Pro Ala Ser
                85                  90                  95

Leu Gln Arg Val Arg Arg Pro Val Ala Met Val Met Pro Ala Arg Arg
                100                 105                 110

Thr Pro His Val Gln Ala Val Gln Gly Pro Leu Gly Ser Pro Pro Lys
            115                 120                 125

Arg Gly Pro Leu Pro Thr Glu Glu Gln Arg Val Tyr Arg Arg Lys Glu
        130                 135                 140

Leu Glu Glu Val Ser Pro Glu Thr Pro Val Val Pro Ala Thr Thr Gln
145                 150                 155                 160

Arg Thr Leu Ala Arg Pro Gly Pro Glu Pro Ala Pro Ala Thr Asp Glu
                165                 170                 175

Arg Asp Arg Val Gln Lys Lys Thr Phe Thr Lys Trp Val Asn Lys His
                180                 185                 190

Leu Ile Lys Ala Gln Arg His Ile Ser Asp Leu Tyr Glu Asp Leu Arg
            195                 200                 205

Asp Gly His Asn Leu Ile Ser Leu Leu Glu Val Leu Ser Gly Asp Ser
        210                 215                 220

Leu Pro Arg Glu Lys Gly Arg Met Arg Phe His Lys Leu Gln Asn Val
225                 230                 235                 240

Gln Ile Ala Leu Asp Tyr Leu Arg His Arg Gln Val Lys Leu Val Asn
                245                 250                 255

Ile Arg Asn Asp Asp Ile Ala Asp Gly Asn Pro Lys Leu Thr Leu Gly
                260                 265                 270

Leu Ile Trp Thr Ile Ile Leu His Phe Gln Ile Ser Asp Ile Gln Val
            275                 280                 285

Ser Gly Gln Ser Glu Asp Met Thr Ala Lys Glu Lys Leu Leu Leu Trp
        290                 295                 300

Ser Gln Arg Met Val Glu Gly Tyr Gln Gly Leu Arg Cys Asp Asn Phe
305                 310                 315                 320

Thr Ser Ser Trp Arg Asp Gly Arg Leu Phe Asn Ala Ile Ile His Arg
                325                 330                 335

His Lys Pro Leu Leu Ile Asp Met Asn Lys Val Tyr Arg Gln Thr Asn
                340                 345                 350

Leu Glu Asn Leu Asp Gln Ala Phe Ser Val Ala Glu Arg Asp Leu Gly
            355                 360                 365
```

-continued

```
Val Thr Arg Leu Leu Asp Pro Glu Asp Val Asp Val Pro Gln Pro Asp
    370             375             380
Glu Lys Ser Ile Ile Thr Tyr Val Ser Ser Leu Tyr Asp Ala Met Pro
385             390             395             400
Arg Val Pro Asp Val Gln Asp Gly Val Arg Ala Asn Glu Leu Gln Leu
                405             410             415
Arg Trp Gln Glu Tyr Arg Glu Leu Val Leu Leu Leu Gln Trp Met
            420             425             430
Arg His His Thr Ala Ala Phe Glu Glu Arg Arg Phe Pro Ser Ser Phe
        435             440             445
Glu Glu Ile Glu Ile Leu Trp Ser Gln Phe Leu Lys Phe Lys Glu Met
450             455             460
Glu Leu Pro Ala Lys Glu Ala Asp Lys Asn Arg Ser Lys Gly Ile Tyr
465             470             475             480
Gln Ser Leu Glu Gly Ala Val Gln Ala Gly Gln Leu Lys Val Pro Pro
                485             490             495
Gly Tyr His Pro Leu Asp Val Gly Lys Glu Trp Gly Lys Leu His Val
            500             505             510
Ala Ile Leu Glu Arg Glu Lys Gln Leu Arg Ser Glu Phe Glu Arg Leu
        515             520             525
Glu Cys Leu Gln Arg Ile Val Thr Lys Leu Gln Met Glu Ala Gly Leu
530             535             540
Cys Glu Glu Gln Leu Asn Gln Ala Asp Ala Leu Leu Gln Ser Asp Val
545             550             555             560
Arg Leu Leu Ala Ala Gly Lys Val Pro Gln Arg Ala Gly Glu Val Glu
                565             570             575
Arg Asp Leu Asp Lys Ala Asp Ser Met Ile Arg Leu Leu Phe Asn Asp
            580             585             590
Val Gln Thr Leu Lys Asp Gly Arg His Pro Gln Gly Glu Gln Met Tyr
        595             600             605
Arg Arg Val Tyr Arg Leu His Glu Arg Leu Val Ala Ile Arg Thr Glu
610             615             620
Tyr Asn Leu Arg Leu Lys Ala Gly Val Ala Pro Ala Thr Gln Val
625             630             635             640
Ala Gln Val Thr Leu Gln Ser Val Gln Arg Arg Pro Glu Leu Glu Asp
                645             650             655
Ser Thr Leu Arg Tyr Leu Gln Asp Leu Leu Ala Trp Val Glu Glu Asn
            660             665             670
Gln His Arg Val Asp Gly Ala Glu Trp Gly Val Asp Leu Pro Ser Val
        675             680             685
Glu Ala Gln Leu Gly Ser His Arg Gly Leu His Gln Ser Ile Glu Glu
690             695             700
Phe Arg Ala Lys Ile Glu Arg Ala Arg Ser Asp Glu Gly Gln Leu Ser
705             710             715             720
Pro Ala Thr Arg Gly Ala Tyr Arg Asp Cys Leu Gly Arg Leu Asp Leu
                725             730             735
Gln Tyr Ala Lys Leu Leu Asn Ser Ser Lys Ala Arg Leu Arg Ser Leu
            740             745             750
Glu Ser Leu His Ser Phe Val Ala Ala Thr Lys Glu Leu Met Trp
        755             760             765
Leu Asn Glu Lys Glu Glu Glu Val Gly Phe Asp Trp Ser Asp Arg
770             775             780
Asn Thr Asn Met Thr Ala Lys Lys Glu Ser Tyr Ser Ala Leu Met Arg
```

-continued

```
            785                 790                 795                 800
        Glu Leu Glu Leu Lys Glu Lys Ile Lys Glu Leu Gln Asn Ala Gly
                            805                 810                 815

Asp Arg Leu Leu Arg Glu Asp His Pro Ala Arg Pro Thr Val Glu Ser
                            820                 825                 830

Phe Gln Ala Ala Leu Gln Thr Gln Trp Ser Trp Met Leu Gln Leu Cys
                            835                 840                 845

Cys Cys Ile Glu Ala His Leu Lys Glu Asn Ala Ala Tyr Phe Gln Phe
                            850                 855                 860

Phe Ser Asp Val Arg Glu Ala Glu Gly Gln Leu Gln Lys Leu Gln Glu
        865                 870                 875                 880

Ala Leu Arg Arg Lys Tyr Ser Cys Asp Arg Ser Ala Thr Val Thr Arg
                            885                 890                 895

Leu Glu Asp Leu Leu Gln Asp Ala Gln Asp Gly Lys Glu Gln Leu Asn
                            900                 905                 910

Glu Tyr Lys Gly His Leu Ser Gly Leu Ala Lys Arg Ala Lys Ala Val
                            915                 920                 925

Val Gln Leu Lys Pro Arg His Pro Ala His Pro Met Arg Gly Arg Leu
                            930                 935                 940

Pro Leu Leu Ala Val Cys Asp Tyr Lys Gln Val Glu Val Thr Val His
        945                 950                 955                 960

Lys Gly Asp Glu Cys Gln Leu Val Gly Pro Ala Gln Pro Ser His Trp
                            965                 970                 975

Lys Val Leu Ser Ser Ser Gly Ser Glu Ala Ala Val Pro Ser Val Cys
                            980                 985                 990

Phe Leu Val Pro Pro Asn Gln  Glu Ala Gln Glu Ala  Val Thr Arg
                            995                 1000                1005

Leu Glu  Ala Gln His Gln Ala  Leu Val Thr Leu Trp  His Gln Leu
                 1010                1015                1020

His Val  Asp Met Lys Ser Leu  Leu Ala Trp Gln Ser  Leu Arg Arg
                 1025                1030                1035

Asp Val  Gln Leu Ile Arg Ser  Trp Ser Leu Ala Thr  Phe Arg Thr
                 1040                1045                1050

Leu Lys  Pro Glu Glu Gln Arg  Gln Ala Leu His Ser  Leu Glu Leu
                 1055                1060                1065

His Tyr  Gln Ala Phe Leu Arg  Asp Ser Gln Asp Ala  Gly Gly Phe
                 1070                1075                1080

Gly Pro  Glu Asp Arg Leu Met  Ala Glu Arg Glu Tyr  Gly Ser Cys
                 1085                1090                1095

Ser His  His Tyr Gln Gln Leu  Leu Gln Ser Leu Glu  Gln Gly Ala
                 1100                1105                1110

Gln Glu  Glu Ser Arg Cys Gln  Arg Cys Ile Ser Glu  Leu Lys Asp
                 1115                1120                1125

Ile Arg  Leu Gln Leu Glu Ala  Cys Glu Thr Arg Thr  Val His Arg
                 1130                1135                1140

Leu Arg  Leu Pro Leu Asp Lys  Glu Pro Ala Arg Glu  Cys Ala Gln
                 1145                1150                1155

Arg Ile  Ala Glu Gln Gln Lys  Ala Gln Ala Glu Val  Glu Gly Leu
                 1160                1165                1170

Gly Lys  Gly Val Ala Arg Leu  Ser Ala Glu Ala Glu  Lys Val Leu
                 1175                1180                1185

Ala Leu  Pro Glu Pro Ser Pro  Ala Ala Pro Thr Leu  Arg Ser Glu
                 1190                1195                1200
```

```
Leu Glu Leu Thr Leu Gly Lys Leu Glu Gln Val Arg Ser Leu Ser
1205                1210                1215

Ala Ile Tyr Leu Glu Lys Leu Lys Thr Ile Ser Leu Val Ile Arg
1220                1225                1230

Gly Thr Gln Gly Ala Glu Val Leu Arg Ala His Glu Glu Gln
1235                1240                1245

Leu Lys Glu Ala Gln Ala Val Pro Ala Thr Leu Pro Glu Leu Glu
1250                1255                1260

Ala Thr Lys Ala Ser Leu Lys Lys Leu Arg Ala Gln Ala Glu Ala
1265                1270                1275

Gln Gln Pro Thr Phe Asp Ala Leu Arg Asp Glu Leu Arg Gly Ala
1280                1285                1290

Gln Glu Val Gly Glu Arg Leu Gln Gln Arg His Gly Glu Arg Asp
1295                1300                1305

Val Glu Val Glu Arg Trp Arg Glu Arg Val Ala Gln Leu Leu Glu
1310                1315                1320

Arg Trp Gln Ala Val Leu Ala Gln Thr Asp Val Arg Gln Arg Glu
1325                1330                1335

Leu Glu Gln Leu Gly Arg Gln Leu Arg Tyr Tyr Arg Glu Ser Ala
1340                1345                1350

Asp Pro Leu Gly Ala Trp Leu Gln Asp Ala Arg Arg Arg Gln Glu
1355                1360                1365

Gln Ile Gln Ala Met Pro Leu Ala Asp Ser Gln Ala Val Arg Glu
1370                1375                1380

Gln Leu Arg Gln Glu Gln Ala Leu Leu Glu Glu Ile Glu Arg His
1385                1390                1395

Gly Glu Lys Val Glu Glu Cys Gln Arg Phe Ala Lys Gln Tyr Ile
1400                1405                1410

Asn Ala Ile Lys Asp Tyr Glu Leu Gln Leu Val Thr Tyr Lys Ala
1415                1420                1425

Gln Leu Glu Pro Val Ala Ser Pro Ala Lys Lys Pro Lys Val Gln
1430                1435                1440

Ser Gly Ser Glu Ser Val Ile Gln Glu Tyr Val Asp Leu Arg Thr
1445                1450                1455

His Tyr Ser Glu Leu Thr Thr Leu Thr Ser Gln Tyr Ile Lys Phe
1460                1465                1470

Ile Ser Glu Thr Leu Arg Arg Met Glu Glu Glu Arg Leu Ala
1475                1480                1485

Glu Gln Gln Arg Ala Glu Glu Arg Glu Arg Leu Ala Glu Val Glu
1490                1495                1500

Ala Ala Leu Glu Lys Gln Arg Gln Leu Ala Glu Ala His Ala Gln
1505                1510                1515

Ala Lys Ala Gln Ala Glu Arg Glu Ala Lys Glu Leu Gln Gln Arg
1520                1525                1530

Met Gln Glu Glu Val Val Arg Arg Glu Glu Ala Ala Val Asp Ala
1535                1540                1545

Gln Gln Gln Lys Arg Ser Ile Gln Glu Glu Leu Gln Gln Leu Arg
1550                1555                1560

Gln Ser Ser Glu Ala Glu Ile Gln Ala Lys Ala Arg Gln Ala Glu
1565                1570                1575

Ala Ala Glu Arg Ser Arg Leu Arg Ile Glu Glu Glu Ile Arg Val
1580                1585                1590
```

```
Val Arg Leu Gln Leu Glu Ala Thr Glu Arg Gln Arg Gly Gly Ala
    1595                1600                1605

Glu Gly Glu Leu Gln Ala Leu Arg Ala Arg Ala Glu Glu Ala Glu
    1610                1615                1620

Ala Gln Lys Arg Gln Ala Gln Glu Glu Ala Glu Arg Leu Arg Arg
    1625                1630                1635

Gln Val Gln Asp Glu Ser Gln Arg Lys Arg Gln Ala Glu Val Glu
    1640                1645                1650

Leu Ala Ser Arg Val Lys Ala Glu Ala Glu Ala Arg Glu Lys
    1655                1660                1665

Gln Arg Ala Leu Gln Ala Leu Glu Glu Leu Arg Leu Gln Ala Glu
    1670                1675                1680

Glu Ala Glu Arg Arg Leu Arg Gln Ala Glu Val Glu Arg Ala Arg
    1685                1690                1695

Gln Val Gln Val Ala Leu Glu Thr Ala Gln Arg Ser Ala Glu Ala
    1700                1705                1710

Glu Leu Gln Ser Lys Arg Ala Ser Phe Ala Glu Lys Thr Ala Gln
    1715                1720                1725

Leu Glu Arg Ser Leu Gln Glu Glu His Val Ala Val Ala Gln Leu
    1730                1735                1740

Arg Glu Glu Ala Glu Arg Arg Ala Gln Gln Gln Ala Glu Ala Glu
    1745                1750                1755

Arg Ala Arg Glu Glu Ala Glu Arg Glu Leu Glu Arg Trp Gln Leu
    1760                1765                1770

Lys Ala Asn Glu Ala Leu Arg Leu Arg Leu Gln Ala Glu Glu Val
    1775                1780                1785

Ala Gln Gln Lys Ser Leu Ala Gln Ala Glu Ala Glu Lys Gln Lys
    1790                1795                1800

Glu Glu Ala Glu Arg Glu Ala Arg Arg Arg Gly Lys Ala Glu Glu
    1805                1810                1815

Gln Ala Val Arg Gln Arg Glu Leu Ala Glu Gln Glu Leu Glu Lys
    1820                1825                1830

Gln Arg Gln Leu Ala Glu Gly Thr Ala Gln Gln Arg Leu Ala Ala
    1835                1840                1845

Glu Gln Glu Leu Ile Arg Leu Arg Ala Glu Thr Glu Gln Gly Glu
    1850                1855                1860

Gln Gln Arg Gln Leu Leu Glu Glu Leu Ala Arg Leu Gln Arg
    1865                1870                1875

Glu Ala Ala Ala Thr Gln Lys Arg Gln Glu Leu Glu Ala Glu
    1880                1885                1890

Leu Ala Lys Val Arg Ala Glu Met Glu Val Leu Leu Ala Ser Lys
    1895                1900                1905

Ala Arg Ala Glu Glu Glu Ser Arg Ser Thr Ser Glu Lys Ser Lys
    1910                1915                1920

Gln Arg Leu Glu Ala Glu Ala Gly Arg Phe Arg Glu Leu Ala Glu
    1925                1930                1935

Glu Ala Ala Arg Leu Arg Ala Leu Ala Glu Glu Ala Lys Arg Gln
    1940                1945                1950

Arg Gln Leu Ala Glu Glu Asp Ala Ala Arg Gln Arg Ala Glu Ala
    1955                1960                1965

Glu Arg Val Leu Ala Glu Lys Leu Ala Ala Ile Gly Glu Ala Thr
    1970                1975                1980

Arg Leu Lys Thr Glu Ala Glu Ile Ala Leu Lys Glu Lys Glu Ala
```

```
                    1985                1990                1995
Glu  Asn  Glu  Arg  Leu  Arg  Arg  Leu  Ala  Glu  Asp  Glu  Ala  Phe  Gln
          2000                2005                2010

Arg  Arg  Arg  Leu  Glu  Glu  Gln  Ala  Ala  Gln  His  Lys  Ala  Asp  Ile
          2015                2020                2025

Glu  Glu  Arg  Leu  Ala  Gln  Leu  Arg  Lys  Ala  Ser  Asp  Ser  Glu  Leu
          2030                2035                2040

Glu  Arg  Gln  Lys  Gly  Leu  Val  Glu  Asp  Thr  Leu  Arg  Gln  Arg  Arg
          2045                2050                2055

Gln  Val  Glu  Glu  Glu  Ile  Leu  Ala  Leu  Lys  Ala  Ser  Phe  Glu  Lys
          2060                2065                2070

Ala  Ala  Ala  Gly  Lys  Ala  Glu  Leu  Glu  Leu  Glu  Leu  Gly  Arg  Ile
          2075                2080                2085

Arg  Ser  Asn  Ala  Glu  Asp  Thr  Leu  Arg  Ser  Lys  Glu  Gln  Ala  Glu
          2090                2095                2100

Leu  Glu  Ala  Ala  Arg  Gln  Arg  Gln  Leu  Ala  Ala  Glu  Glu  Glu  Arg
          2105                2110                2115

Arg  Arg  Arg  Glu  Ala  Glu  Glu  Arg  Val  Gln  Lys  Ser  Leu  Ala  Ala
          2120                2125                2130

Glu  Glu  Glu  Ala  Ala  Arg  Gln  Arg  Lys  Ala  Ala  Leu  Glu  Glu  Val
          2135                2140                2145

Glu  Arg  Leu  Lys  Ala  Lys  Val  Glu  Glu  Ala  Arg  Arg  Leu  Arg  Glu
          2150                2155                2160

Arg  Ala  Glu  Gln  Glu  Ser  Ala  Arg  Gln  Leu  Gln  Leu  Ala  Gln  Glu
          2165                2170                2175

Ala  Ala  Gln  Lys  Arg  Leu  Gln  Ala  Glu  Glu  Lys  Ala  His  Ala  Phe
          2180                2185                2190

Ala  Val  Gln  Gln  Lys  Glu  Gln  Glu  Leu  Gln  Gln  Thr  Leu  Gln  Gln
          2195                2200                2205

Glu  Gln  Ser  Val  Leu  Asp  Gln  Leu  Arg  Gly  Glu  Ala  Glu  Ala  Ala
          2210                2215                2220

Arg  Arg  Ala  Ala  Glu  Glu  Ala  Glu  Glu  Ala  Arg  Val  Gln  Ala  Glu
          2225                2230                2235

Arg  Glu  Ala  Ala  Gln  Ser  Arg  Arg  Gln  Val  Glu  Glu  Ala  Glu  Arg
          2240                2245                2250

Leu  Lys  Gln  Ser  Ala  Glu  Glu  Gln  Ala  Gln  Ala  Arg  Ala  Gln  Ala
          2255                2260                2265

Gln  Ala  Ala  Ala  Glu  Lys  Leu  Arg  Lys  Glu  Ala  Glu  Gln  Glu  Ala
          2270                2275                2280

Ala  Arg  Arg  Ala  Gln  Ala  Glu  Gln  Ala  Ala  Leu  Arg  Gln  Lys  Gln
          2285                2290                2295

Ala  Ala  Asp  Ala  Glu  Met  Glu  Lys  His  Lys  Lys  Phe  Ala  Glu  Gln
          2300                2305                2310

Thr  Leu  Arg  Gln  Lys  Ala  Gln  Val  Glu  Gln  Glu  Leu  Thr  Thr  Leu
          2315                2320                2325

Arg  Leu  Gln  Leu  Glu  Glu  Thr  Asp  His  Gln  Lys  Asn  Leu  Leu  Asp
          2330                2335                2340

Glu  Glu  Leu  Gln  Arg  Leu  Lys  Ala  Glu  Ala  Thr  Glu  Ala  Ala  Arg
          2345                2350                2355

Gln  Arg  Ser  Gln  Val  Glu  Glu  Leu  Phe  Ser  Val  Arg  Val  Gln
          2360                2365                2370

Met  Glu  Glu  Leu  Ser  Lys  Leu  Lys  Ala  Arg  Ile  Glu  Ala  Glu  Asn
          2375                2380                2385
```

```
Arg Ala Leu Ile Leu Arg Asp Lys Asp Asn Thr Gln Arg Phe Leu
    2390                2395                2400

Gln Glu Glu Ala Glu Lys Met Lys Gln Val Ala Glu Glu Ala Ala
    2405                2410                2415

Arg Leu Ser Val Ala Ala Gln Glu Ala Ala Arg Leu Arg Gln Leu
    2420                2425                2430

Ala Glu Glu Asp Leu Ala Gln Gln Arg Ala Leu Ala Glu Lys Met
    2435                2440                2445

Leu Lys Glu Lys Met Gln Ala Val Gln Glu Ala Thr Arg Leu Lys
    2450                2455                2460

Ala Glu Ala Glu Leu Leu Gln Gln Gln Lys Glu Leu Ala Gln Glu
    2465                2470                2475

Gln Ala Arg Arg Leu Gln Glu Asp Lys Glu Gln Met Ala Gln Gln
    2480                2485                2490

Leu Ala Glu Glu Thr Gln Gly Phe Gln Arg Thr Leu Glu Ala Glu
    2495                2500                2505

Arg Gln Arg Gln Leu Glu Met Ser Ala Glu Ala Glu Arg Leu Lys
    2510                2515                2520

Leu Arg Val Ala Glu Met Ser Arg Ala Gln Ala Arg Ala Glu Glu
    2525                2530                2535

Asp Ala Gln Arg Phe Arg Lys Gln Ala Glu Glu Ile Gly Glu Lys
    2540                2545                2550

Leu His Arg Thr Glu Leu Ala Thr Gln Glu Lys Val Thr Leu Val
    2555                2560                2565

Gln Thr Leu Glu Ile Gln Arg Gln Gln Ser Asp His Asp Ala Glu
    2570                2575                2580

Arg Leu Arg Glu Ala Ile Ala Glu Leu Glu Arg Glu Lys Glu Lys
    2585                2590                2595

Leu Gln Gln Glu Ala Lys Leu Leu Gln Leu Lys Ser Glu Glu Met
    2600                2605                2610

Gln Thr Val Gln Gln Glu Gln Leu Leu Gln Glu Thr Gln Ala Leu
    2615                2620                2625

Gln Gln Ser Phe Leu Ser Glu Lys Asp Ser Leu Leu Gln Arg Glu
    2630                2635                2640

Arg Phe Ile Glu Gln Glu Lys Ala Lys Leu Glu Gln Leu Phe Gln
    2645                2650                2655

Asp Glu Val Ala Lys Ala Gln Gln Leu Arg Glu Glu Gln Gln Arg
    2660                2665                2670

Gln Gln Gln Gln Met Glu Gln Glu Arg Gln Arg Leu Val Ala Ser
    2675                2680                2685

Met Glu Glu Ala Arg Arg Arg Gln His Glu Ala Glu Glu Gly Val
    2690                2695                2700

Arg Arg Lys Gln Glu Glu Leu Gln Gln Leu Glu Gln Gln Arg Arg
    2705                2710                2715

Gln Gln Glu Glu Leu Leu Ala Glu Glu Asn Gln Arg Leu Arg Glu
    2720                2725                2730

Gln Leu Gln Leu Leu Glu Glu Gln His Arg Ala Ala Leu Ala His
    2735                2740                2745

Ser Glu Glu Val Thr Ala Ser Gln Val Ala Ala Thr Lys Thr Leu
    2750                2755                2760

Pro Asn Gly Arg Asp Ala Leu Asp Gly Pro Ala Ala Glu Ala Glu
    2765                2770                2775
```

```
Pro Glu His Ser Phe Asp Gly Leu Arg Arg Lys Val Ser Ala Gln
2780                2785                2790

Arg Leu Gln Glu Ala Gly Ile Leu Ser Ala Glu Leu Gln Arg
2795                2800                2805

Leu Ala Gln Gly His Thr Thr Val Asp Glu Leu Ala Arg Arg Glu
2810                2815                2820

Asp Val Arg His Tyr Leu Gln Gly Arg Ser Ser Ile Ala Gly Leu
2825                2830                2835

Leu Leu Lys Ala Thr Asn Glu Lys Leu Ser Val Tyr Ala Ala Leu
2840                2845                2850

Gln Arg Gln Leu Leu Ser Pro Gly Thr Ala Leu Ile Leu Leu Glu
2855                2860                2865

Ala Gln Ala Ala Ser Gly Phe Leu Leu Asp Pro Val Arg Asn Arg
2870                2875                2880

Arg Leu Thr Val Asn Glu Ala Val Lys Glu Gly Val Val Gly Pro
2885                2890                2895

Glu Leu His His Lys Leu Leu Ser Ala Glu Arg Ala Val Thr Gly
2900                2905                2910

Tyr Lys Asp Pro Tyr Thr Gly Gln Gln Ile Ser Leu Phe Gln Ala
2915                2920                2925

Met Gln Lys Gly Leu Ile Val Arg Glu His Gly Ile Arg Leu Leu
2930                2935                2940

Glu Ala Gln Ile Ala Thr Gly Gly Val Ile Asp Pro Val His Ser
2945                2950                2955

His Arg Val Pro Val Asp Val Ala Tyr Arg Arg Gly Tyr Phe Asp
2960                2965                2970

Glu Glu Met Asn Arg Val Leu Ala Asp Pro Ser Asp Asp Thr Lys
2975                2980                2985

Gly Phe Phe Asp Pro Asn Thr His Glu Asn Leu Thr Tyr Leu Gln
2990                2995                3000

Leu Leu Glu Arg Cys Val Glu Asp Pro Glu Thr Gly Leu Cys Leu
3005                3010                3015

Leu Pro Leu Thr Asp Lys Ala Ala Lys Gly Gly Glu Leu Val Tyr
3020                3025                3030

Thr Asp Ser Glu Ala Arg Asp Val Phe Glu Lys Ala Thr Val Ser
3035                3040                3045

Ala Pro Phe Gly Lys Phe Gln Gly Lys Thr Val Thr Ile Trp Glu
3050                3055                3060

Ile Ile Asn Ser Glu Tyr Phe Thr Ala Glu Gln Arg Arg Asp Leu
3065                3070                3075

Leu Arg Gln Phe Arg Thr Gly Arg Ile Thr Val Glu Lys Ile Ile
3080                3085                3090

Lys Ile Ile Ile Thr Val Val Glu Glu Gln Glu Gln Lys Gly Arg
3095                3100                3105

Leu Cys Phe Glu Gly Leu Arg Ser Leu Val Pro Ala Ala Glu Leu
3110                3115                3120

Leu Glu Ser Arg Val Ile Asp Arg Glu Leu Tyr Gln Gln Leu Gln
3125                3130                3135

Arg Gly Glu Arg Ser Val Arg Asp Val Ala Glu Val Asp Thr Val
3140                3145                3150

Arg Arg Ala Leu Arg Gly Ala Asn Val Ile Ala Gly Val Trp Leu
3155                3160                3165

Glu Glu Ala Gly Gln Lys Leu Ser Ile Tyr Asn Ala Leu Lys Lys
```

```
              3170            3175           3180
Asp Leu Leu Pro Ser Asp Met Ala Val Ala Leu Leu Glu Ala Gln
    3185            3190           3195

Ala Gly Thr Gly His Ile Ile Asp Pro Ala Thr Ser Ala Arg Leu
    3200            3205           3210

Thr Val Asp Glu Ala Val Arg Ala Gly Leu Val Gly Pro Glu Phe
    3215            3220           3225

His Glu Lys Leu Leu Ser Ala Glu Lys Ala Val Thr Gly Tyr Arg
    3230            3235           3240

Asp Pro Tyr Thr Gly Gln Ser Val Ser Leu Phe Gln Ala Leu Lys
    3245            3250           3255

Lys Gly Leu Ile Pro Arg Glu Gln Gly Leu Arg Leu Leu Asp Ala
    3260            3265           3270

Gln Leu Ser Thr Gly Gly Ile Val Asp Pro Ser Lys Ser His Arg
    3275            3280           3285

Val Pro Leu Asp Val Ala Cys Ala Arg Gly Cys Leu Asp Glu Glu
    3290            3295           3300

Thr Ser Arg Ala Leu Ser Ala Pro Arg Ala Asp Ala Lys Ala Tyr
    3305            3310           3315

Ser Asp Pro Ser Thr Gly Glu Pro Ala Thr Tyr Gly Glu Leu Gln
    3320            3325           3330

Gln Arg Cys Arg Pro Asp Gln Leu Thr Gly Leu Ser Leu Leu Pro
    3335            3340           3345

Leu Ser Glu Lys Ala Ala Arg Ala Arg Gln Glu Leu Tyr Ser
    3350            3355           3360

Glu Leu Gln Ala Arg Glu Thr Phe Glu Lys Thr Pro Val Glu Val
    3365            3370           3375

Pro Val Gly Gly Phe Lys Gly Arg Thr Val Thr Val Trp Glu Leu
    3380            3385           3390

Ile Ser Ser Glu Tyr Phe Thr Ala Glu Gln Arg Gln Glu Leu Leu
    3395            3400           3405

Arg Gln Phe Arg Thr Gly Lys Val Thr Val Glu Lys Val Ile Lys
    3410            3415           3420

Ile Leu Ile Thr Ile Val Glu Glu Val Glu Thr Leu Arg Gln Glu
    3425            3430           3435

Arg Leu Ser Phe Ser Gly Leu Arg Ala Pro Val Pro Ala Ser Glu
    3440            3445           3450

Leu Leu Ala Ser Gly Val Leu Ser Arg Ala Gln Phe Glu Gln Leu
    3455            3460           3465

Lys Asp Gly Lys Thr Thr Val Lys Asp Leu Ser Glu Leu Gly Ser
    3470            3475           3480

Val Arg Thr Leu Leu Gln Gly Ser Gly Cys Leu Ala Gly Ile Tyr
    3485            3490           3495

Leu Glu Asp Thr Lys Glu Lys Val Ser Ile Tyr Glu Ala Met Arg
    3500            3505           3510

Arg Gly Leu Leu Arg Ala Thr Thr Ala Ala Leu Leu Leu Glu Ala
    3515            3520           3525

Gln Ala Ala Thr Gly Phe Leu Val Asp Pro Val Arg Asn Gln Arg
    3530            3535           3540

Leu Tyr Val His Glu Ala Val Lys Ala Gly Val Val Gly Pro Glu
    3545            3550           3555

Leu His Glu Gln Leu Leu Ser Ala Glu Lys Ala Val Thr Gly Tyr
    3560            3565           3570
```

-continued

Arg Asp Pro Tyr Ser Gly Ser Thr Ile Ser Leu Phe Gln Ala Met
3575                3580                3585

Gln Lys Gly Leu Val Leu Arg Gln His Gly Ile Arg Leu Leu Glu
3590                3595                3600

Ala Gln Ile Ala Thr Gly Gly Ile Ile Asp Pro Val His Ser His
3605                3610                3615

Arg Val Pro Val Asp Val Ala Tyr Gln Arg Gly Tyr Phe Ser Glu
3620                3625                3630

Glu Met Asn Arg Val Leu Ala Asp Pro Ser Asp Thr Lys Gly
3635                3640                3645

Phe Phe Asp Pro Asn Thr His Glu Asn Leu Thr Tyr Arg Gln Leu
3650                3655                3660

Leu Glu Arg Cys Val Glu Asp Pro Glu Thr Gly Leu Arg Leu Leu
3665                3670                3675

Pro Leu Lys Gly Ala Glu Lys Ala Glu Val Val Glu Thr Thr Gln
3680                3685                3690

Val Tyr Thr Glu Glu Thr Arg Arg Ala Phe Glu Glu Thr Gln
3695                3700                3705

Ile Asp Ile Pro Gly Gly Gly Ser His Gly Gly Ser Thr Met Ser
3710                3715                3720

Leu Trp Glu Val Met Gln Ser Asp Leu Ile Pro Glu Glu Gln Arg
3725                3730                3735

Ala Gln Leu Met Ala Asp Phe Gln Ala Gly Arg Val Thr Lys Glu
3740                3745                3750

Arg Met Ile Ile Ile Ile Glu Ile Ile Glu Lys Thr Glu Ile
3755                3760                3765

Ile Arg Gln Gln Gly Leu Ala Ser Tyr Asp Tyr Val Arg Arg Arg
3770                3775                3780

Leu Thr Ala Glu Asp Leu Phe Glu Ala Arg Ile Ile Ser Leu Glu
3785                3790                3795

Thr Tyr Asn Leu Leu Arg Glu Gly Thr Arg Ser Leu Arg Glu Ala
3800                3805                3810

Leu Glu Ala Glu Ser Ala Trp Cys Tyr Leu Tyr Gly Thr Gly Ser
3815                3820                3825

Val Ala Gly Val Tyr Leu Pro Gly Ser Arg Gln Thr Leu Ser Ile
3830                3835                3840

Tyr Gln Ala Leu Lys Lys Gly Leu Leu Ser Ala Glu Val Ala Arg
3845                3850                3855

Leu Leu Leu Glu Ala Gln Ala Ala Thr Gly Phe Leu Leu Asp Pro
3860                3865                3870

Val Lys Gly Glu Arg Leu Thr Val Asp Glu Ala Val Arg Lys Gly
3875                3880                3885

Leu Val Gly Pro Glu Leu His Asp Arg Leu Leu Ser Ala Glu Arg
3890                3895                3900

Ala Val Thr Gly Tyr Arg Asp Pro Tyr Thr Glu Gln Thr Ile Ser
3905                3910                3915

Leu Phe Gln Ala Met Lys Lys Glu Leu Ile Pro Thr Glu Glu Ala
3920                3925                3930

Leu Arg Leu Leu Asp Ala Gln Leu Ala Thr Gly Gly Ile Val Asp
3935                3940                3945

Pro Arg Leu Gly Phe His Leu Pro Leu Glu Val Ala Tyr Gln Arg
3950                3955                3960

```
Gly Tyr Leu Asn Lys Asp Thr His Asp Gln Leu Ser Glu Pro Ser
    3965                3970                3975

Glu Val Arg Ser Tyr Val Asp Pro Ser Thr Asp Glu Arg Leu Ser
    3980                3985                3990

Tyr Thr Gln Leu Leu Arg Arg Cys Arg Arg Asp Asp Gly Thr Gly
    3995                4000                4005

Gln Leu Leu Leu Pro Leu Ser Asp Ala Arg Lys Leu Thr Phe Arg
    4010                4015                4020

Gly Leu Arg Lys Gln Ile Thr Met Glu Glu Leu Val Arg Ser Gln
    4025                4030                4035

Val Met Asp Glu Ala Thr Ala Leu Gln Leu Arg Glu Gly Leu Thr
    4040                4045                4050

Ser Ile Glu Glu Val Thr Lys Asn Leu Gln Lys Phe Leu Glu Gly
    4055                4060                4065

Thr Ser Cys Ile Ala Gly Val Phe Val Asp Ala Thr Lys Glu Arg
    4070                4075                4080

Leu Ser Val Tyr Gln Ala Met Lys Lys Gly Ile Ile Arg Pro Gly
    4085                4090                4095

Thr Ala Phe Glu Leu Leu Glu Ala Gln Ala Ala Thr Gly Tyr Val
    4100                4105                4110

Ile Asp Pro Ile Lys Gly Leu Lys Leu Thr Val Glu Glu Ala Val
    4115                4120                4125

Arg Met Gly Ile Val Gly Pro Glu Phe Lys Asp Lys Leu Leu Ser
    4130                4135                4140

Ala Glu Arg Ala Val Thr Gly Tyr Lys Asp Pro Tyr Ser Gly Lys
    4145                4150                4155

Leu Ile Ser Leu Phe Gln Ala Met Lys Lys Gly Leu Ile Leu Lys
    4160                4165                4170

Asp His Gly Ile Arg Leu Leu Glu Ala Gln Ile Ala Thr Gly Gly
    4175                4180                4185

Ile Ile Asp Pro Glu Glu Ser His Arg Leu Pro Val Glu Val Ala
    4190                4195                4200

Tyr Lys Arg Gly Leu Phe Asp Glu Glu Met Asn Glu Ile Leu Thr
    4205                4210                4215

Asp Pro Ser Asp Asp Thr Lys Gly Phe Phe Asp Pro Asn Thr Glu
    4220                4225                4230

Glu Asn Leu Thr Tyr Leu Gln Leu Met Glu Arg Cys Ile Thr Asp
    4235                4240                4245

Pro Gln Thr Gly Leu Cys Leu Leu Pro Leu Lys Glu Lys Lys Arg
    4250                4255                4260

Glu Arg Lys Thr Ser Ser Lys Ser Ser Val Arg Lys Arg Arg Val
    4265                4270                4275

Val Ile Val Asp Pro Glu Thr Gly Lys Glu Met Ser Val Tyr Glu
    4280                4285                4290

Ala Tyr Arg Lys Gly Leu Ile Asp His Gln Thr Tyr Leu Glu Leu
    4295                4300                4305

Ser Glu Gln Glu Cys Glu Trp Glu Glu Ile Thr Ile Ser Ser Ser
    4310                4315                4320

Asp Gly Val Val Lys Ser Met Ile Ile Asp Arg Arg Ser Gly Arg
    4325                4330                4335

Gln Tyr Asp Ile Asp Asp Ala Ile Ala Lys Asn Leu Ile Asp Arg
    4340                4345                4350

Ser Ala Leu Asp Gln Tyr Arg Ala Gly Thr Leu Ser Ile Thr Glu
```

```
               4355                4360                4365

Phe Ala Asp Met Leu Ser Gly Asn Ala Gly Phe Arg Ser Arg
         4370                4375                4380

Ser Ser Ser Val Gly Ser Ser Ser Tyr Pro Ile Ser Pro Ala
         4385                4390                4395

Val Ser Arg Thr Gln Leu Ala Ser Trp Ser Asp Pro Thr Glu Glu
         4400                4405                4410

Thr Gly Pro Val Ala Gly Ile Leu Asp Thr Glu Thr Leu Glu Lys
         4415                4420                4425

Val Ser Ile Thr Glu Ala Met His Arg Asn Leu Val Asp Asn Ile
         4430                4435                4440

Thr Gly Gln Arg Leu Leu Glu Ala Gln Ala Cys Thr Gly Gly Ile
         4445                4450                4455

Ile Asp Pro Ser Thr Gly Glu Arg Phe Pro Val Thr Asp Ala Val
         4460                4465                4470

Asn Lys Gly Leu Val Asp Lys Ile Met Val Asp Arg Ile Asn Leu
         4475                4480                4485

Ala Gln Lys Ala Phe Cys Gly Phe Glu Asp Pro Arg Thr Lys Thr
         4490                4495                4500

Lys Met Ser Ala Ala Gln Ala Leu Lys Lys Gly Trp Leu Tyr Tyr
         4505                4510                4515

Glu Ala Gly Gln Arg Phe Leu Glu Val Gln Tyr Leu Thr Gly Gly
         4520                4525                4530

Leu Ile Glu Pro Asp Thr Pro Gly Arg Val Pro Leu Asp Glu Ala
         4535                4540                4545

Leu Gln Arg Gly Thr Val Asp Ala Arg Thr Ala Gln Lys Leu Arg
         4550                4555                4560

Asp Val Gly Ala Tyr Ser Lys Tyr Leu Thr Cys Pro Lys Thr Lys
         4565                4570                4575

Leu Lys Ile Ser Tyr Lys Asp Ala Leu Asp Arg Ser Met Val Glu
         4580                4585                4590

Glu Gly Thr Gly Leu Arg Leu Leu Glu Ala Ala Ala Gln Ser Thr
         4595                4600                4605

Lys Gly Tyr Tyr Ser Pro Tyr Ser Val Ser Gly Ser Gly Ser Thr
         4610                4615                4620

Ala Gly Ser Arg Thr Gly Ser Arg Thr Gly Ser Arg Ala Gly Ser
         4625                4630                4635

Arg Arg Gly Ser Phe Asp Ala Thr Gly Ser Gly Phe Ser Met Thr
         4640                4645                4650

Phe Ser Ser Ser Ser Tyr Ser Ser Ser Gly Tyr Gly Arg Arg Tyr
         4655                4660                4665

Ala Ser Gly Ser Ser Ala Ser Leu Gly Gly Pro Glu Ser Ala Val
         4670                4675                4680

Ala

<210> SEQ ID NO 2
<211> LENGTH: 344
<212> TYPE: PRT
<213> ORGANISM: Artificial Sequence
<220> FEATURE:
<223> OTHER INFORMATION: Synthetic Polypeptide

<400> SEQUENCE: 2

Met Arg Ser His His His His His His His His His Arg Ser Gly
1               5                   10                  15
```

```
Thr Gly Asp Asp Asp Lys Ala Met Ala Asp Ile Gly Ser Glu Phe
        20                  25                  30

Glu Leu Arg Arg Gln Ala Cys Gly Phe Arg Ser Arg Ser Ser Val
            35                  40                  45

Gly Ser Ser Ser Tyr Pro Ile Ser Pro Ala Val Ser Arg Thr Gln
 50                  55                  60

Leu Ala Ser Trp Ser Asp Pro Thr Glu Glu Thr Gly Pro Val Ala Gly
 65                  70                  75                  80

Ile Leu Asp Thr Glu Thr Leu Glu Lys Val Ser Ile Thr Glu Ala Met
                 85                  90                  95

His Arg Asn Leu Val Asp Asn Ile Thr Gly Gln Arg Leu Leu Glu Ala
             100                 105                 110

Gln Ala Cys Thr Gly Gly Ile Ile Asp Pro Ser Thr Gly Glu Arg Phe
         115                 120                 125

Pro Val Thr Asp Ala Val Asn Lys Gly Leu Val Asp Lys Ile Met Val
 130                 135                 140

Asp Arg Ile Asn Leu Ala Gln Lys Ala Phe Cys Gly Phe Glu Asp Pro
145                 150                 155                 160

Arg Thr Lys Thr Lys Met Ser Ala Ala Gln Ala Leu Lys Lys Gly Trp
                165                 170                 175

Leu Tyr Tyr Glu Ala Gly Gln Arg Phe Leu Glu Val Gln Tyr Leu Thr
            180                 185                 190

Gly Gly Leu Ile Glu Pro Asp Thr Pro Gly Arg Val Pro Leu Asp Glu
        195                 200                 205

Ala Leu Gln Arg Gly Thr Val Asp Ala Arg Thr Ala Gln Lys Leu Arg
    210                 215                 220

Asp Val Gly Ala Tyr Ser Lys Tyr Leu Thr Cys Pro Lys Thr Lys Leu
225                 230                 235                 240

Lys Ile Ser Tyr Lys Asp Ala Leu Asp Arg Ser Met Val Glu Glu Gly
                245                 250                 255

Thr Gly Leu Arg Leu Leu Glu Ala Ala Ala Gln Ser Thr Lys Gly Tyr
            260                 265                 270

Tyr Ser Pro Tyr Ser Val Ser Gly Ser Gly Ser Thr Ala Gly Ser Arg
        275                 280                 285

Thr Gly Ser Arg Thr Gly Ser Arg Ala Gly Ser Arg Arg Gly Ser Phe
    290                 295                 300

Asp Ala Thr Gly Ser Gly Phe Ser Met Thr Phe Ser Ser Ser Ser Tyr
305                 310                 315                 320

Ser Ser Ser Gly Tyr Gly Arg Arg Tyr Ala Ser Gly Ser Ser Ser Leu
                325                 330                 335

Gly Gly Pro Glu Ser Ala Val Ala
            340

<210> SEQ ID NO 3
<211> LENGTH: 540
<212> TYPE: PRT
<213> ORGANISM: Artificial Sequence
<220> FEATURE:
<223> OTHER INFORMATION: Synthetic Polypeptide

<400> SEQUENCE: 3

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30
```

```
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Val Pro Arg
            210                 215                 220
Gly Ser Glu Phe Glu Leu Arg Arg Gln Ala Cys Gly Phe Arg Ser Arg
225                 230                 235                 240
Ser Ser Ser Val Gly Ser Ser Ser Tyr Pro Ile Ser Pro Ala Val
                245                 250                 255
Ser Arg Thr Gln Leu Ala Ser Trp Ser Asp Pro Thr Glu Glu Thr Gly
            260                 265                 270
Pro Val Ala Gly Ile Leu Asp Thr Glu Thr Leu Glu Lys Val Ser Ile
            275                 280                 285
Thr Glu Ala Met His Arg Asn Leu Val Asp Asn Ile Thr Gly Gln Arg
            290                 295                 300
Leu Leu Glu Ala Gln Ala Cys Thr Gly Gly Ile Ile Asp Pro Ser Thr
305                 310                 315                 320
Gly Glu Arg Phe Pro Val Thr Asp Ala Val Asn Lys Gly Leu Val Asp
                325                 330                 335
Lys Ile Met Val Asp Arg Ile Asn Leu Ala Gln Lys Ala Phe Cys Gly
                340                 345                 350
Phe Glu Asp Pro Arg Thr Lys Thr Lys Met Ser Ala Ala Gln Ala Leu
            355                 360                 365
Lys Lys Gly Trp Leu Tyr Tyr Glu Ala Gly Gln Arg Phe Leu Glu Val
            370                 375                 380
Gln Tyr Leu Thr Gly Gly Leu Ile Glu Pro Asp Thr Pro Gly Arg Val
385                 390                 395                 400
Pro Leu Asp Glu Ala Leu Gln Arg Gly Thr Val Asp Ala Arg Thr Ala
                405                 410                 415
Gln Lys Leu Arg Asp Val Gly Ala Tyr Ser Lys Tyr Leu Thr Cys Pro
                420                 425                 430
Lys Thr Lys Leu Lys Ile Ser Tyr Lys Asp Ala Leu Asp Arg Ser Met
            435                 440                 445
```

```
Val Glu Glu Gly Thr Gly Leu Arg Leu Leu Glu Ala Ala Gln Ser
450                 455                 460

Thr Lys Gly Tyr Tyr Ser Pro Tyr Ser Val Ser Gly Ser Gly Ser Thr
465                 470                 475                 480

Ala Gly Ser Arg Thr Gly Ser Arg Thr Gly Ser Arg Ala Gly Ser Arg
                485                 490                 495

Arg Gly Ser Phe Asp Ala Thr Gly Ser Gly Phe Ser Met Thr Phe Ser
                500                 505                 510

Ser Ser Ser Tyr Ser Ser Ser Gly Tyr Gly Arg Arg Tyr Ala Ser Gly
            515                 520                 525

Ser Ser Ser Leu Gly Gly Pro Glu Ser Ala Val Ala
            530                 535                 540

<210> SEQ ID NO 4
<211> LENGTH: 1398
<212> TYPE: DNA
<213> ORGANISM: Artificial Sequence
<220> FEATURE:
<223> OTHER INFORMATION: Synthetic Polynucleotide

<400> SEQUENCE: 4
atgaacttcg ggctcagctt gattttcctt gccctcattt taaaaggtgt ccagtgtgag      60
gtgcagctgg tggagtctgg gggagacttg gtgaagcctg agggtccct gaaactctcc     120 tgtgcagcct ctggattcac tttcagtagg tatggcatgt cttgggttcg ccagactcca     180
gacaagaggc tggagtgggt cgcaaccatt agtattggtg gtacttacac ctactatcca     240
gacagtatga aggggcgatt caccatctcc agagacaatg ccaagaacac cctgtacctg     300
caaatgagca gtctgaagtc tgaggacaca gccatgtatt actgtgcaag acggggtat      360 ggtaactact cttactatgg tatggactac tggggtcaag gaacctcagt caccgtctcc     420
tcagccaaaa cgacaccccc atctgtctat ccactggccc ctggatctgc tgcccaaact     480
aactccatgg tgaccctggg atgcctggtc aagggctatt ccctgagcc agtgacagtg     540 acctggaact ctggatccct gtccagcggt gtgcacacct tcccagctgt cctgcagtct     600
gacctctaca ctctgagcag ctcagtgact gtccccctcca gcacctggcc cagcgagacc     660
gtcacctgca acgttgccca cccggccagc agcaccaagg tggacaagaa aattgtgccc     720
agggattgtg gttgtaagcc ttgcatatgt acagtcccag aagtatcatc tgtcttcatc     780
ttccccccaa agcccaagga tgtgctcacc attactctga ctcctaaggt cacgtgtgtt     840
gtggtagaca tcagcaagga tgatcccgag gtccagttca gctggtttgt agatgatgtg     900
gaggtgcaca cagctcagac gcaaccccgg gaggagcagt tcaacagcac tttccgctca     960
gtcagtgaac ttcccatcat gcaccaggac tggctcaatg gcaaggagtt caaatgcagg    1020
gtcaacagtg cagctttccc tgcccccatc gagaaaacca tctccaaaac caaaggcaga    1080
ccgaaggctc cacaggtgta caccattcca cctcccaagg agcagatggc caaggataaa    1140
gtcagtctga cctgcatgat aacagacttc ttccctgaag acattactgt ggagtggcag    1200
tggaatgggc agccagcgga gaactacaag aacactcagc ccatcatgga cacagatggc    1260
tcttacttcg tctacagcaa gctcaatgtg cagaagagca ctgggaggc aggaaatact    1320 ttcacctgct ctgtgttaca tgagggcctg cacaaccacc atactgagaa gagcctctcc    1380
cactctcctg gtaaatga                                                  1398

<210> SEQ ID NO 5
<211> LENGTH: 57
```

```
<212> TYPE: DNA
<213> ORGANISM: Artificial Sequence
<220> FEATURE:
<223> OTHER INFORMATION: Synthetic Polynucleotide

<400> SEQUENCE: 5
atgaacttcg ggctcagctt gattttcctt gccctcattt taaaaggtgt ccagtgt        57

<210> SEQ ID NO 6
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 6
gaggtgcagc tggtggagtc tgggggagac ttggtgaagc ctggagggtc cctgaaactc        60
tcctgtgcag cctctggatt cactttcagt                                        90

<210> SEQ ID NO 7
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 7
aggtatggca tgtct                                                        15

<210> SEQ ID NO 8
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 8
tgggttcgcc agactccaga caagaggctg gagtgggtcg ca                          42

<210> SEQ ID NO 9
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 9
accattagta ttggtggtac ttacacctac tatccagaca gtatgaaggg g                51

<210> SEQ ID NO 10
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 10
cgattcacca tctccagaga caatgccaag aacaccctgt acctgcaaat gagcagtctg        60
aagtctgagg acacagccat gtattactgt gcaaga                                 96

<210> SEQ ID NO 11
<211> LENGTH: 39
<212> TYPE: DNA
<213> ORGANISM: Artificial Sequence
<220> FEATURE:
```

<223> OTHER INFORMATION: Synthetic Polynucleotide

<400> SEQUENCE: 11
cgggggtatg gtaactactc ttactatggt atggactac          39

<210> SEQ ID NO 12
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 12
tggggtcaag gaacctcagt caccgtctcc tca          33

<210> SEQ ID NO 13
<211> LENGTH: 366
<212> TYPE: DNA
<213> ORGANISM: Artificial Sequence
<220> FEATURE:
<223> OTHER INFORMATION: Synthetic Polynucleotide

<400> SEQUENCE: 13
gaggtgcagc tggtggagtc tgggggagac ttggtgaagc ctggagggtc cctgaaactc          60
tcctgtgcag cctctggatt cactttcagt aggtatggca tgtcttgggt tcgccagact         120
ccagacaaga ggctggagtg ggtcgcaacc attagtattg gtggtactta cacctactat         180
ccagacagta tgaagggggcg attcaccatc tccagagaca atgccaagaa caccctgtac         240
ctgcaaatga gcagtctgaa gtctgaggac acagccatgt attactgtgc aagacggggg         300
tatggtaact actcttacta tggtatggac tactggggtc aaggaacctc agtcaccgtc         360
tcctca                                                                     366

<210> SEQ ID NO 14
<211> LENGTH: 972
<212> TYPE: DNA
<213> ORGANISM: Artificial Sequence
<220> FEATURE:
<223> OTHER INFORMATION: Synthetic Polynucleotide

<400> SEQUENCE: 14
gccaaaacga caccccatc tgtctatcca ctggcccctg gatctgctgc ccaaactaac          60
tccatggtga ccctgggatg cctggtcaag ggctatttcc ctgagccagt gacagtgacc         120
tggaactctg gatccctgtc cagcggtgtg cacaccttcc cagctgtcct gcagtctgac         180
ctctacactc tgagcagctc agtgactgtc ccctccagca cctggcccag cgagaccgtc         240
acctgcaacg ttgcccaccc ggccagcagc accaaggtgg acaagaaaat tgtgcccagg         300
gattgtggtt gtaagccttg catatgtaca gtcccagaag tatcatctgt cttcatcttc         360
cccccaaagc caaggatgt gctcaccatt actctgactc ctaaggtcac gtgtgttgtg         420
gtagacatca gcaaggatga tcccgaggtc cagttcagct ggtttgtaga tgatgtggag         480
gtgcacacag ctcagacgca accccgggag gagcagttca acagcacttt ccgctcagtc         540
agtgaacttc ccatcatgca ccaggactgg ctcaatggca aggagttcaa atgcagggtc         600
aacagtgcag ctttccctgc ccccatcgag aaaaccatct ccaaaaccaa aggcagaccg         660
aaggctccac aggtgtacac cattccacct cccaaggagc agatggccaa ggataaagtc         720
agtctgacct gcatgataac agacttcttc cctgaagaca ttactgtgga gtggcagtgg         780
aatgggcagc cagcggagaa ctacaagaac actcagccca tcatggacac agatggctct         840

```
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aa                                                         972
```

<210> SEQ ID NO 15
<211> LENGTH: 201
<212> TYPE: PRT
<213> ORGANISM: Artificial Sequence
<220> FEATURE:
<223> OTHER INFORMATION: Synthetic Polypeptide

<400> SEQUENCE: 15

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Arg Tyr Gly Met Ser Trp Val Arg Gln Thr Pro Asp Lys Arg Leu
    50                  55                  60

Glu Trp Val Ala Thr Ile Ser Ile Gly Gly Thr Tyr Thr Tyr Tyr Pro
65                  70                  75                  80

Asp Ser Met Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Arg Gly Tyr Gly Asn Tyr Ser Tyr Tyr Gly Met
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp
        195                 200
```

<210> SEQ ID NO 16
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 16

```
Met Asn Phe Gly Leu Ser Leu Ile Phe Leu Ala Leu Ile Leu Lys Gly
1               5                   10                  15

Val Gln Cys
```

<210> SEQ ID NO 17
<211> LENGTH: 30
<212> TYPE: PRT
<213> ORGANISM: Artificial Sequence
<220> FEATURE:
<223> OTHER INFORMATION: Synthetic Polypeptide

```
<400> SEQUENCE: 17

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 18

Arg Tyr Gly Met Ser
1               5

<210> SEQ ID NO 19
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 19

Trp Val Arg Gln Thr Pro Asp Lys Arg Leu Glu Trp Val Ala
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 20

Thr Ile Ser Ile Gly Gly Thr Tyr Thr Tyr Tyr Pro Asp Ser Met Lys
1               5                   10                  15

Gly

<210> SEQ ID NO 21
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 21

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Arg
            20                  25                  30

<210> SEQ ID NO 22
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 22

Arg Gly Tyr Gly Asn Tyr Ser Tyr Tyr Gly Met Asp Tyr
1               5                   10
```

```
<210> SEQ ID NO 23
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 23

Trp Gly Gln Gly Thr Ser Val Thr Val Ser Ser
1               5                   10

<210> SEQ ID NO 24
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 24

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ile Gly Gly Thr Tyr Thr Tyr Tyr Pro Asp Ser Met
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Gly Tyr Gly Asn Tyr Ser Tyr Tyr Gly Met Asp Tyr Trp
            100                 105                 110

Gly Gln Gly Thr Ser Val Thr Val Ser Ser
        115                 120

<210> SEQ ID NO 25
<211> LENGTH: 324
<212> TYPE: PRT
<213> ORGANISM: Artificial Sequence
<220> FEATURE:
<223> OTHER INFORMATION: Synthetic Polypeptide

<400> SEQUENCE: 25

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125
```

Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Val Glu
145                 150                 155                 160

Val His Thr Ala Gln Thr Gln Pro Arg Glu Glu Gln Phe Asn Ser Thr
            165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
            245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 26
<211> LENGTH: 720
<212> TYPE: DNA
<213> ORGANISM: Artificial Sequence
<220> FEATURE:
<223> OTHER INFORMATION: Synthetic Polynucleotide

<400> SEQUENCE: 26
atgaggttct ctgctcagct tctggggctg cttgtgctct ggatccctgg atccactgca    60
gatattgtga tgacgcaggc tgcattctcc aatccagtca ctcttggaac atcagcttcc   120
atctcctgca ggtctagtaa gagtctccta catagtaatg catcactta tttgtattgg    180 tatctgcaga agccaggcca gtctcctcag ctcctgattt atcagatgtc aaccttgcc    240 tcaggagtcc cagacaggtt cagtagcagt gggtcaggaa ctgatttcac actgagaatc   300
agcagagtgg aggctgagga tgtgggtgtt tattactgtg ctcaaaatct agaacttccg   360
ctcacgttcg gtgctgggac caagctggag ctgaaacggg ctgatgctgc accaactgta   420
tccatcttcc caccatccag tgagcagtta acatctggag gtgcctcagt cgtgtgcttc   480
ttgaacaact tctaccccaa agacatcaat gtcaagtgga agattgatgg cagtgaacga   540
caaaatggcg tcctgaacag ttggactgat caggacagca agacagcac ctacagcatg   600 agcagcaccc tcacgttgac caaggacgag tatgaacgac ataacagcta cctgtgtgag   660
gccactcaca gacatcaac ttcacccatt gtcaagagct caacaggaa tgagtgttag    720

<210> SEQ ID NO 27
<211> LENGTH: 60
<212> TYPE: DNA
<213> ORGANISM: Artificial Sequence
<220> FEATURE:

-continued

<223> OTHER INFORMATION: Synthetic Polynucleotide

<400> SEQUENCE: 27
atgaggttct ctgctcagct tctggggctg cttgtgctct ggatccctgg atccactgca    60

<210> SEQ ID NO 28
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 28
gatattgtga tgacgcaggc tgcattctcc aatccagtca ctcttggaac atcagcttcc    60
atctcctgc                                                            69

<210> SEQ ID NO 29
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 29
aggtctagta agagtctcct acatagtaat ggcatcactt atttgtat                 48

<210> SEQ ID NO 30
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 30
tggtatctgc agaagccagg ccagtctcct cagctcctga tttat                    45

<210> SEQ ID NO 31
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 31
cagatgtcca accttgcctc a                                              21

<210> SEQ ID NO 32
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 32
ggagtcccag acaggttcag tagcagtggg tcaggaactg atttcacact gagaatcagc    60
agagtggagg ctgaggatgt gggtgtttat tactgt                              96

<210> SEQ ID NO 33
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 33

-continued

```
gctcaaaatc tagaacttcc gctcacg                                        27

<210> SEQ ID NO 34
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 34
ttcggtgctg ggaccaagct ggagctgaaa                                     30

<210> SEQ ID NO 35
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 35
gatattgtga tgacgcaggc tgcattctcc aatccagtca ctcttggaac atcagcttcc    60
atctcctgca ggtctagtaa gagtctccta catagtaatg catcactta tttgtattgg    120 tatctgcaga agccaggcca gtctcctcag ctcctgattt atcagatgtc caaccttgcc   180
tcaggagtcc cagacaggtt cagtagcagt gggtcaggaa ctgatttcac actgagaatc   240
agcagagtgg aggctgagga tgtgggtgtt tattactgtg ctcaaaatct agaacttccg   300
ctcacgttcg gtgctgggac caagctggag ctgaaa                             336

<210> SEQ ID NO 36
<211> LENGTH: 382
<212> TYPE: DNA
<213> ORGANISM: Artificial Sequence
<220> FEATURE:
<223> OTHER INFORMATION: Synthetic Polynucleotide

<400> SEQUENCE: 36
ctgtgctcaa aatctagaac ttccgctcac gttcggtgct gggaccaagc tggagctgaa    60
acgggctgat gctgcaccaa ctgtatccat cttcccacca tccagtgagc agttaacatc   120
tggaggtgcc tcagtcgtgt gcttcttgaa caacttctac cccaaagaca tcaatgtcaa   180
gtggaagatt gatggcagtg aacgacaaaa tggcgtcctg aacagttgga ctgatcagga   240
cagcaaagac agcacctaca gcatgagcag cacccctcacg ttgaccaagg acgagtatga   300
acgacataac agctatacct gtgaggccac tcacaagaca tcaacttcac ccattgtcaa   360
gagcttcaac aggaatgagt gt                                            382

<210> SEQ ID NO 37
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 37

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
            20                  25                  30

Val Thr Leu Gly Thr Ser Ala Ser Ile Ser Cys Arg Ser Ser Lys Ser
        35                  40                  45
```

```
Leu Leu His Ser Asn Gly Ile Thr Tyr Leu Tyr Trp Tyr Leu Gln Lys
         50                  55                  60

Pro Gly Gln Ser Pro Gln Leu Leu Ile Tyr Gln Met Ser Asn Leu Ala
 65                  70                  75                  80

Ser Gly Val Pro Asp Arg Phe Ser Ser Gly Ser Gly Thr Asp Phe
             85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Leu Thr Phe Gly Ala Gly Thr Lys
            115                 120                 125

Leu Glu Leu Lys Arg Ala Asp Ala Ala Pro Thr Val Ser Ile Phe Pro
        130                 135                 140

Pro Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235

<210> SEQ ID NO 38
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 38

Met Arg Phe Ser Ala Gln Leu Leu Gly Leu Leu Val Leu Trp Ile Pro
1               5                   10                  15

Gly Ser Thr Ala
            20

<210> SEQ ID NO 39
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 39

Asp Ile Val Met Thr Gln Ala Ala Phe Ser Asn Pro Val Thr Leu Gly
1               5                   10                  15

Thr Ser Ala Ser Ile Ser Cys
            20

<210> SEQ ID NO 40
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 40
```

Arg Ser Ser Lys Ser Leu Leu His Ser Asn Gly Ile Thr Tyr Leu Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 41

Trp Tyr Leu Gln Lys Pro Gly Gln Ser Pro Gln Leu Leu Ile Tyr
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 42

Gln Met Ser Asn Leu Ala Ser
1               5

<210> SEQ ID NO 43
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 43

Gly Val Pro Asp Arg Phe Ser Ser Gly Ser Gly Thr Asp Phe Thr
1               5                   10                  15

Leu Arg Ile Ser Arg Val Glu Ala Glu Asp Val Gly Val Tyr Tyr Cys
                20                  25                  30

<210> SEQ ID NO 44
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 44

Ala Gln Asn Leu Glu Leu Pro Leu Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 45

Phe Gly Ala Gly Thr Lys Leu Glu Leu Lys
1               5                   10

<210> SEQ ID NO 46
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 46

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110

<210> SEQ ID NO 47
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 47

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 48
<211> LENGTH: 1410
<212> TYPE: DNA
<213> ORGANISM: Artificial Sequence
<220> FEATURE:
<223> OTHER INFORMATION: Synthetic Polynucleotide

<400> SEQUENCE: 48
atggcttggg tgtggacctt gctattcctg atggcagctg cccaaagtat ccaagcacag      60
atccagttgg tgcagtctgg acctgagctg aagaagcctg agagacagt caagatctcc     120 tgcaaggctt ctggttatac cttcacagac tattcaatgc actgggtgaa gcaggctcca     180
ggaaagggtt taaagtggat gggctggata aacactgaga ctggtgagcc aacatatgca     240
gatgacttca agggacggtt tgccttctct ttggaaacct ctgccagcac tgcctatttg     300
cagatcaaca acctcaaaaa tgaggacacg gctacatatt tctgtgcccc cggagggttt     360
gcttactggg gccaagggac tctggtcact gtctctgcag ccaaaacaac cccccatca     420 gtctatccac tggcccctgg gtgtggagat acaactggtt cctccgtgac tctgggatgc     480

```
ctggtcaagg gctacttccc tgagtcagtg actgtgactt ggaactctgg atccctgtcc      540
agcagtgtgc acaccttccc agctctcctg cagtctggac tctacactat gagcagctca      600
gtgactgtcc cctccagcac ctggccaagt cagaccgtca cctgcagcgt tgctcaccca      660
gccagcagca ccacggtgga caaaaaactt gagcccagcg ggcccatttc aacaatcaac      720
ccctgtcctc catgcaagga gtgtcacaaa tgcccagctc ctaacctcga gggtggacca      780
tccgtcttca tcttccctcc aaatatcaag gatgtactca tgatctccct gacacccaag      840
gtcacgtgtg tggtggtgga tgtgagcgag gatgacccag acgtccagat cagctggttt      900
gtgaacaacg tggaagtaca cacagctcag acacaaaccc atagagagga ttacaacagt      960
actatccggg tggtcagcac cctcccccatc cagcaccagg actggatgag tggcaaggag     1020
ttcaaatgca aggtcaacaa caaagacctc ccatcaccca tcgagagaac catctcaaaa     1080
attaaagggc tagtcagagc tccacaagta tacatcttgc cgccaccagc agagcagttg     1140
tccaggaaag atgtcagtct cacttgcctg gtcgtgggct tcaaccctgg agacatcagt     1200
gtggagtgga ccagcaatgg gcatacagag gagaactaca aggacaccgc accagtcctg     1260
gactctgacg gttcttactt catatatagc aagctcaata tgaaaacaag caagtgggag     1320
aaaacagatt ccttctcatg caacgtgaga cacgagggtc tgaaaaatta ctacctgaag     1380
aagaccatct cccggtctcc gggtaaatga                                       1410

<210> SEQ ID NO 49
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 49
atggcttggg tgtggacctt gctattcctg atggcagctg cccaaagtat ccaagca         57

<210> SEQ ID NO 50
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 50
cagatccagt tggtgcagtc tggacctgag ctgaagaagc ctggagagac agtcaagatc      60
tcctgcaagg cttctggtta taccttcaca                                        90

<210> SEQ ID NO 51
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 51
gactattcaa tgcac                                                        15

<210> SEQ ID NO 52
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 52
tgggtgaagc aggctccagg aaagggttta aagtggatgg gc                42

<210> SEQ ID NO 53
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 53
tggataaaca ctgagactgg tgagccaaca tatgcagatg acttcaaggg a       51

<210> SEQ ID NO 54
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 54
cggtttgcct tctctttgga aacctctgcc agcactgcct atttgcagat caacaacctc   60
aaaaatgagg acacggctac atatttctgt gccccc                              96

<210> SEQ ID NO 55
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 55
ggagggtttg cttac                                                     15

<210> SEQ ID NO 56
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 56
tggggccaag ggactctggt cactgtctct gca                                 33

<210> SEQ ID NO 57
<211> LENGTH: 342
<212> TYPE: DNA
<213> ORGANISM: Artificial Sequence
<220> FEATURE:
<223> OTHER INFORMATION: Synthetic Polynucleotide

<400> SEQUENCE: 57
cagatccagt tggtgcagtc tggacctgag ctgaagaagc ctggagagac agtcaagatc    60
tcctgcaagg cttctggtta taccttcaca gactattcaa tgcactgggt gaagcaggct   120
ccaggaaagg gtttaaagtg gatgggctgg ataaacactg agactggtga gccaacatat   180
gcagatgact tcaagggacg gtttgccttc tctttggaaa cctctgccag cactgcctat   240
ttgcagatca acaacctcaa aaatgaggac acggctacat atttctgtgc ccccggaggg   300
tttgcttact ggggccaagg gactctggtc actgtctctg ca                     342

<210> SEQ ID NO 58
<211> LENGTH: 1008
```

<212> TYPE: DNA
<213> ORGANISM: Artificial Sequence
<220> FEATURE:
<223> OTHER INFORMATION: Synthetic Polynucleotide

<400> SEQUENCE: 58

```
gccaaaacaa cacccccatc agtctatcca ctggcccctg ggtgtggaga tacaactggt    60
tcctccgtga ctctgggatg cctggtcaag ggctacttcc ctgagtcagt gactgtgact   120
tggaactctg gatccctgtc cagcagtgtg cacaccttcc cagctctcct gcagtctgga   180
ctctacacta tgagcagctc agtgactgtc ccctccagca cctggccaag tcagaccgtc   240
acctgcagcg ttgctcaccc agccagcagc accacggtgg acaaaaaact gagcccagc   300
gggcccattt caacaatcaa ccctgtcct ccatgcaagg agtgtcacaa atgcccagct   360
cctaacctcg agggtggacc atccgtcttc atcttccctc caaatatcaa ggatgtactc   420
atgatctccc tgacacccaa ggtcacgtgt gtggtggtgg atgtgagcga ggatgaccca   480
gacgtccaga tcagctggtt tgtgaacaac gtggaagtac acacagctca gacacaaacc   540
catagagagg attacaacag tactatccgg gtggtcagca ccctccccat ccagcaccag   600
gactggatga gtggcaagga gttcaaatgc aaggtcaaca caaagacct cccatcaccc   660
atcgagagaa ccatctcaaa aattaaaggg ctagtcagag ctccacaagt atacatcttg   720
ccgccaccag cagagcagtt gtccaggaaa gatgtcagtc tcacttgcct ggtcgtgggc   780
ttcaaccctg agacatcag tgtggagtgg accagcaatg ggcatacaga ggagaactac   840
aaggacaccg caccagtcct ggactctgac ggttcttact tcatatatag caagctcaat   900
atgaaaacaa gcaagtggga gaaacagat tccttctcat gcaacgtgag acacgagggt   960
ctgaaaaatt actacctgaa gaagaccatc tcccggtctc cgggtaaa                 1008
```

<210> SEQ ID NO 59
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 59

```
Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ser Met His Trp Val Lys Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Pro Gly Gly Phe Ala Tyr Trp Gly Gln Gly Thr Leu
        115                 120                 125

Val Thr Val Ser Ala Ala Lys Thr Thr Pro Pro Ser Val Tyr Pro Leu
    130                 135                 140

Ala Pro Gly Cys Gly Asp Thr Thr Gly Ser Ser Val Thr Leu Gly Cys
```

```
            145                 150                 155                 160
        Leu Val Lys Gly Tyr Phe Pro Glu Ser Val Thr Val Thr Trp Asn Ser
                        165                 170                 175

Gly Ser Leu Ser Ser Val His Thr Phe Pro Ala Leu Leu Gln Ser
                    180                 185                 190

Gly Leu Tyr Thr Met Ser Ser Val Thr Val Pro Ser Ser Thr Trp
                    195                 200                 205

Pro Ser Gln Thr Val Thr Cys Ser Val Ala His Pro Ala Ser Ser Thr
                210                 215                 220

Thr Val Asp Lys Lys Leu Glu Pro Ser Gly Pro Ile Ser Thr Ile Asn
        225                 230                 235                 240

Pro Cys Pro Pro Cys Lys Glu Cys His Lys Cys Pro Ala Pro Asn Leu
                        245                 250                 255

Glu Gly Gly Pro Ser Val Phe Ile Phe Pro Pro Asn Ile Lys Asp Val
                    260                 265                 270

Leu Met Ile Ser Leu Thr Pro Lys Val Thr Cys Val Val Asp Val
                275                 280                 285

Ser Glu Asp Asp Pro Asp Val Gln Ile Ser Trp Phe Val Asn Asn Val
            290                 295                 300

Glu Val His Thr Ala Gln Thr Gln Thr His Arg Glu Asp Tyr Asn Ser
        305                 310                 315                 320

Thr Ile Arg Val Val Ser Thr Leu Pro Ile Gln His Gln Asp Trp Met
                        325                 330                 335

Ser Gly Lys Glu Phe Lys Cys Lys Val Asn Asn Lys Asp Leu Pro Ser
                    340                 345                 350

Pro Ile Glu Arg Thr Ile Ser Lys Ile Lys Gly Leu Val Arg Ala Pro
                355                 360                 365

Gln Val Tyr Ile Leu Pro Pro Pro Ala Glu Gln Leu Ser Arg Lys Asp
            370                 375                 380

Val Ser Leu Thr Cys Leu Val Val Gly Phe Asn Pro Gly Asp Ile Ser
        385                 390                 395                 400

Val Glu Trp Thr Ser Asn Gly His Thr Glu Glu Asn Tyr Lys Asp Thr
                        405                 410                 415

Ala Pro Val Leu Asp Ser Asp Gly Ser Tyr Phe Ile Tyr Ser Lys Leu
                    420                 425                 430

Asn Met Lys Thr Ser Lys Trp Glu Lys Thr Asp Ser Phe Ser Cys Asn
                435                 440                 445

Val Arg His Glu Gly Leu Lys Asn Tyr Tyr Leu Lys Lys Thr Ile Ser
            450                 455                 460

Arg Ser Pro Gly Lys
        465

<210> SEQ ID NO 60
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 60

Met Ala Trp Val Trp Thr Leu Leu Phe Leu Met Ala Ala Gln Ser
1               5                   10                  15

Ile Gln Ala

<210> SEQ ID NO 61
```

```
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 61

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr
            20                  25                  30

<210> SEQ ID NO 62
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 62

Asp Tyr Ser Met His
1               5

<210> SEQ ID NO 63
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 63

Trp Val Lys Gln Ala Pro Gly Lys Gly Leu Lys Trp Met Gly
1               5                   10

<210> SEQ ID NO 64
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 64

Trp Ile Asn Thr Glu Thr Gly Glu Pro Thr Tyr Ala Asp Asp Phe Lys
1               5                   10                  15

Gly

<210> SEQ ID NO 65
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 65

Arg Phe Ala Phe Ser Leu Glu Thr Ser Ala Ser Thr Ala Tyr Leu Gln
1               5                   10                  15

Ile Asn Asn Leu Lys Asn Glu Asp Thr Ala Thr Tyr Phe Cys Ala Pro
            20                  25                  30

<210> SEQ ID NO 66
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 66

Gly Gly Phe Ala Tyr
1               5

<210> SEQ ID NO 67
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 67

Trp Gly Gln Gly Thr Leu Val Thr Val Ser Ala
1               5                   10

<210> SEQ ID NO 68
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 68

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Pro Gly Gly Phe Ala Tyr Trp Gly Gln Gly Thr Leu Val Thr Val
            100                 105                 110

Ser Ala

<210> SEQ ID NO 69
<211> LENGTH: 336
<212> TYPE: PRT
<213> ORGANISM: Artificial Sequence
<220> FEATURE:
<223> OTHER INFORMATION: Synthetic Polypeptide

<400> SEQUENCE: 69

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95
```

```
Leu Glu Pro Ser Gly Pro Ile Ser Thr Ile Asn Pro Cys Pro Pro Cys
                100                 105                 110

Lys Glu Cys His Lys Cys Pro Ala Pro Asn Leu Glu Gly Gly Pro Ser
            115                 120                 125

Val Phe Ile Phe Pro Pro Asn Ile Lys Asp Val Leu Met Ile Ser Leu
        130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 70
<211> LENGTH: 720
<212> TYPE: DNA
<213> ORGANISM: Artificial Sequence
<220> FEATURE:
<223> OTHER INFORMATION: Synthetic Polynucleotide

<400> SEQUENCE: 70
atgaggtgcc tagctgagtt cctggggctg cttgtgctct ggatccctgg agccattggg    60
gatattgtga tgactcaggc tgcaccctct gtacctgtca ctcctggaga gtcagtatcc   120
atctcctgca ggtctagtaa gagtctcctg catagtaatg caacacttta cttgtattgg   180
ttcctgcaga ggccaggcca gtctcctcag ctcctgatat atcggatgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacatct agaatatccg   360
ctcacgttcg gtgctgggac caagctggag ctgaaacggg ctgatgctgc accaactgta   420
tccatcttcc caccatccag tgagcagtta acatctggag gtgcctcagt cgtgtgcttc   480
ttgaacaact ctaccccaa agacatcaat gtcaagtgga gattgatgg cagtgaacga   540 caaaatggcg tcctgaacag ttggactgat caggacagca agacagcac ctacagcatg   600 agcagcaccc tcacgttgac caaggacgag tatgaacgca taacagcta tcctgtgag   660 gccactcaca agacatcaac ttcacccatt gtcaagagct caacaggaa tgagtgttag   720
```

<210> SEQ ID NO 71
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 71
atgaggtgcc tagctgagtt cctggggctg cttgtgctct ggatccctgg agccattggg    60

<210> SEQ ID NO 72
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 72
gatattgtga tgactcaggc tgcaccctct gtacctgtca ctcctggaga gtcagtatcc    60
atctcctgc                                                            69

<210> SEQ ID NO 73
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 73
aggtctagta agagtctcct gcatagtaat ggcaacactt acttgtat                 48

<210> SEQ ID NO 74
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 74
tggttcctgc agaggccagg ccagtctcct cagctcctga tatat                    45

<210> SEQ ID NO 75
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 75
cggatgtcca accttgcctc a                                              21

<210> SEQ ID NO 76
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 76
ggagtcccag acaggttcag tgcagtggg tcaggaactg ctttcacact gagaatcagt     60
agagtggagg ctgaggatgt gggtgtttat tactgt                              96

<210> SEQ ID NO 77
<211> LENGTH: 27

```
<212> TYPE: DNA
<213> ORGANISM: Artificial Sequence
<220> FEATURE:
<223> OTHER INFORMATION: Synthetic Polynucleotide

<400> SEQUENCE: 77
atgcaacatc tagaatatcc gctcacg                                              27

<210> SEQ ID NO 78
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 78
ttcggtgctg ggaccaagct ggagctgaaa                                           30

<210> SEQ ID NO 79
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 79
gatattgtga tgactcaggc tgcaccctct gtacctgtca ctcctggaga gtcagtatcc          60
atctcctgca ggtctagtaa gagtctcctg catagtaatg gcaacactta cttgtattgg        120
ttcctgcaga ggccaggcca gtctcctcag ctcctgatat atcggatgtc caaccttgcc        180
tcaggagtcc cagacaggtt cagtggcagt gggtcaggaa ctgctttcac actgagaatc        240
agtagagtgg aggctgagga tgtgggtgtt tattactgta tgcaacatct agaatatccg        300
ctcacgttcg gtgctgggac caagctggag ctgaaa                                   336

<210> SEQ ID NO 80
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 80
cgggctgatg ctgcaccaac tgtatccatc ttcccaccat ccagtgagca gttaacatct         60
ggaggtgcct cagtcgtgtg cttcttgaac aacttctacc ccaaagacat caatgtcaag        120
tggaagattg atggcagtga acgacaaaat ggcgtcctga cagttggac tgatcaggac         180 agcaaagaca gcacctacag catgagcagc accctcacgt tgaccaagga cgagtatgaa        240
cgacataaca gctatacctg tgaggccact cacaagacat caacttcacc cattgtcaag        300
agcttcaaca ggaatgagtg t                                                   321

<210> SEQ ID NO 81
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 81

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
```

```
            20                  25                  30
Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Leu Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 82
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 82

Met Arg Cys Leu Ala Glu Phe Leu Gly Leu Leu Val Leu Trp Ile Pro
1               5                   10                  15

Gly Ala Ile Gly
            20

<210> SEQ ID NO 83
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 83

Asp Ile Val Met Thr Gln Ala Ala Pro Ser Val Pro Val Thr Pro Gly
1               5                   10                  15

Glu Ser Val Ser Ile Ser Cys
            20

<210> SEQ ID NO 84
<211> LENGTH: 16
<212> TYPE: PRT
<213> ORGANISM: Artificial Sequence
<220> FEATURE:
```

<223> OTHER INFORMATION: Synthetic Polypeptide

<400> SEQUENCE: 84

Arg Ser Ser Lys Ser Leu Leu His Ser Asn Gly Asn Thr Tyr Leu Tyr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 85

Trp Phe Leu Gln Arg Pro Gly Gln Ser Pro Gln Leu Leu Ile Tyr
1               5                   10                  15

<210> SEQ ID NO 86
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 86

Arg Met Ser Asn Leu Ala Ser
1               5

<210> SEQ ID NO 87
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 87

Gly Val Pro Asp Arg Phe Ser Gly Ser Gly Ser Gly Thr Ala Phe Thr
1               5                   10                  15

Leu Arg Ile Ser Arg Val Glu Ala Glu Asp Val Gly Val Tyr Tyr Cys
            20                  25                  30

<210> SEQ ID NO 88
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 88

Met Gln His Leu Glu Tyr Pro Leu Thr
1               5

<210> SEQ ID NO 89
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 89

Phe Gly Ala Gly Thr Lys Leu Glu Leu Lys Arg
1               5                   10

<210> SEQ ID NO 90
<211> LENGTH: 113
<212> TYPE: PRT

<213> ORGANISM: Artificial Sequence
<220> FEATURE:
<223> OTHER INFORMATION: Synthetic Polypeptide

<400> SEQUENCE: 90

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

Arg

<210> SEQ ID NO 91
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 91

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 92
<211> LENGTH: 364
<212> TYPE: PRT
<213> ORGANISM: Homo sapiens

<400> SEQUENCE: 92

Ser Ser Ser Asp Gly Val Val Lys Ser Met Ile Ile Asp Arg Arg Ser
1               5                   10                  15

Gly Arg Gln Tyr Asp Ile Asp Asp Ala Ile Ala Lys Asn Leu Ile Asp
            20                  25                  30

Arg Ser Ala Leu Asp Gln Tyr Arg Ala Gly Thr Leu Ser Ile Thr Glu
        35                  40                  45

Phe Ala Asp Met Leu Ser Gly Asn Ala Gly Gly Phe Arg Ser Arg Ser
    50                  55                  60

```
Ser Ser Val Gly Ser Ser Ser Tyr Pro Ile Ser Pro Ala Val Ser
 65                  70                  75                  80

Arg Thr Gln Leu Ala Ser Trp Ser Asp Pro Thr Glu Thr Gly Pro
                 85                  90                  95

Val Ala Gly Ile Leu Asp Thr Glu Thr Leu Glu Lys Val Ser Ile Thr
            100                 105                 110

Glu Ala Met His Arg Asn Leu Val Asp Asn Ile Thr Gly Gln Arg Leu
            115                 120                 125

Leu Glu Ala Gln Ala Cys Thr Gly Gly Ile Ile Asp Pro Ser Thr Gly
130                 135                 140

Glu Arg Phe Pro Val Thr Asp Ala Val Asn Lys Gly Leu Val Asp Lys
145                 150                 155                 160

Ile Met Val Asp Arg Ile Asn Leu Ala Gln Lys Ala Phe Cys Gly Phe
                165                 170                 175

Glu Asp Pro Arg Thr Lys Thr Lys Met Ser Ala Ala Gln Ala Leu Lys
            180                 185                 190

Lys Gly Trp Leu Tyr Tyr Glu Ala Gly Gln Arg Phe Leu Glu Val Gln
            195                 200                 205

Tyr Leu Thr Gly Gly Leu Ile Glu Pro Asp Thr Pro Gly Arg Val Pro
210                 215                 220

Leu Asp Glu Ala Leu Gln Arg Gly Thr Val Asp Ala Arg Thr Ala Gln
225                 230                 235                 240

Lys Leu Arg Asp Val Gly Ala Tyr Ser Lys Tyr Leu Thr Cys Pro Lys
                245                 250                 255

Thr Lys Leu Lys Ile Ser Tyr Lys Asp Ala Leu Asp Arg Ser Met Val
            260                 265                 270

Glu Glu Gly Thr Gly Leu Arg Leu Leu Glu Ala Ala Ala Gln Ser Thr
            275                 280                 285

Lys Gly Tyr Tyr Ser Pro Tyr Ser Val Ser Gly Ser Gly Ser Thr Ala
            290                 295                 300

Gly Ser Arg Thr Gly Ser Arg Thr Gly Ser Arg Ala Gly Ser Arg Arg
305                 310                 315                 320

Gly Ser Phe Asp Ala Thr Gly Ser Gly Phe Ser Met Thr Phe Ser Ser
                325                 330                 335

Ser Ser Tyr Ser Ser Ser Gly Tyr Gly Arg Arg Tyr Ala Ser Gly Ser
            340                 345                 350

Ser Ala Ser Leu Gly Gly Pro Glu Ser Ala Val Ala
            355                 360

<210> SEQ ID NO 93
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 93

Gly Gly Gly Ser
1
```

PLECTIN-1 BINDING ANTIBODIES AND USES THEREOF

RELATED APPLICATIONS

This Application is a national stage filing under 35 U.S.C. § 371 of international application number PCT/US2017/026711, filed Apr. 7, 2017, which claims the benefit of the filing date under 35 U.S.C. § 119(e) of U.S. provisional application Ser. No. 62/320,117, filed Apr. 8, 2016, entitled "PLECTIN-1 BINDING ANTIBODIES AND USES THEREOF", the entire contents of each of which are incorporated herein by reference.

BACKGROUND

Pancreatic ductal adenocarcinoma (PDAC) is the 4th leading cause of cancer death in the United States showing a rapid clinical course leading to death. Once diagnosed, PDAC has a median survival of 6 months and a 5-year survival rate of only 3 percent (Li et al., Lancet 363:1049-1057 (2004)).

As chemotherapy and radiotherapy have only modest benefits, and surgery is only possible in 20% of patients, early detection that allows surgical resection offers the best hope for longer survival (Yeo et al., Ann Surg 222:580-588 (1995); discussion 588-592). Indeed, the detection of PDAC or high-grade precursors in high-risk patient groups (e.g., hereditary cancer syndromes, chronic pancreatitis, and new-onset diabetes) represents a critical unmet need in the cancer diagnostic portfolio (Brentnall et al., Ann. Intern. Med. 131:247-255 (1999); Canto et al., Clin. Gastroenterol. Hepatol. 2:606-621 (2004)).

Serum CA-19-9 is the clinically used biomarker; however, it lacks the sensitivity needed to detect early-stage PDAC (Goggins, J. Clin. Oncol. 23:4524-4531 (2005)). In addition, cross-sectional abdominal imaging has proven to be unreliable to detect early-stage PDAC in high-risk patients (Pelaez-Luna et al., Am J Gastroenterol 102:2157-2163 (2007)).

Thus a high priority in this field of medicine is the identification of biomarkers for the development of binding ligands as diagnostics, such as imaging probes for detecting pre-neoplastic/early invasive lesions and for use in treatments.

SUMMARY

Aspects of the present disclosure relate to a recognition that successful development of clinically useful antibody-based agents, such as antibody drug conjugates (ADCs), is influenced by the specificity and selectivity of the agent for its target. Plectin-1 is a useful biomarker for a variety of cancers, including ovarian, esophageal, and head and neck squamous cells carcinomas, as well as pancreatic ductal adenocarcinoma. In contrast with antibody targets, such as CD30, which is targeted by Brentuximab vedotin, and Her2, which is targeted by Ado-trastuzumab Emtansine, plectin-1 is a particularly useful target because it is present on the cell surface exclusively in certain cancer cells (e.g., pancreatic ductal adenocarcinoma cells, ovarian cancer cells, etc.), thus giving exquisite specificity and selectivity. Accordingly, in some embodiments, the disclosure relates to antibodies and antigen binding fragments that bind specifically to plectin-1 on the surface of cancer cells, and methods of use thereof. In some embodiments, binding of an anti-plectin-1 antibody as described by the disclosure to a plectin-1 expressing cell induces death (e.g., triggers apoptosis) of the cell.

In some aspects, the disclosure provides an antibody or antigen binding fragment that specifically binds an amino acid sequence having at least 85% identity to SEQ ID NO: 92. In some aspects, the disclosure provides an antibody or antigen binding fragment that specifically binds an amino acid sequence having at least 90%, at least 95%, at least 96%, at least 97% at least 98% or at least 99% identity to SEQ ID NO: 92. In some embodiments, the antibody specifically binds an amino acid sequence set forth as: SEQ ID NO: 92.

In some aspects, the disclosure provides an antibody, or antigen binding fragment, that specifically binds to cell-surface exposed plectin-1 antigen and that comprises six complementarity determining regions (CDRs): CDRH1, CDRH2, CDRH3, CDRL1, CDRL2, and CDRL3, wherein CDRH1 comprises a sequence as set forth in SEQ ID NO: 18, CDRH2 comprises a sequence as set forth in SEQ ID NO: 20, CDRH3 comprises a sequence as set forth in SEQ ID NO: 22, CDRL1 comprises a sequence as set forth in SEQ ID NO: 40, CDRL2 comprises a sequence as set forth in SEQ ID NO: 42, and CDRL3 comprises a sequence as set forth in SEQ ID NO: 44; or wherein CDRH1 comprises a sequence as set forth in SEQ ID NO: 62, CDRH2 comprises a sequence as set forth in SEQ ID NO: 64, CDRH3 comprises a sequence as set forth in SEQ ID NO: 66, CDRL1 comprises a sequence as set forth in SEQ ID NO: 84, CDRL2 comprises a sequence as set forth in SEQ ID NO: 86, and CDRL3 comprises a sequence as set forth in SEQ ID NO: 88.

In some embodiments, CDRH1 comprises a sequence as set forth in SEQ ID NO: 18, CDRH2 comprises a sequence as set forth in SEQ ID NO: 20, CDRH3 comprises a sequence as set forth in SEQ ID NO: 22, CDRL1 comprises a sequence as set forth in SEQ ID NO: 40, CDRL2 comprises a sequence as set forth in SEQ ID NO: 42, and CDRL3 comprises a sequence as set forth in SEQ ID NO: 44.

In some aspects, the disclosure provides an antibody or antigen binding fragment that specifically binds to cell-surface exposed plectin-1, wherein the antibody or antigen binding fragment comprises variable heavy chain region comprising a complementarity determining region 3 (CDRH3) having a sequence set forth as: SEQ ID NO: 22 or SEQ ID NO: 66. In some embodiments, the antibody further comprises a light chain variable region comprising a complementarity determining region 3 (CDRL3) having a sequence set forth as: SEQ ID NO: 44 or SEQ ID NO: 88.

In some embodiments, the antibody, or antigen binding fragment comprises the heavy chain variable domain sequence of SEQ ID NO: 24. In some embodiments, the antibody, or antigen binding fragment comprises the light chain variable domain sequence of SEQ ID NO: 46. In some embodiments, the antibody, or antigen binding fragment comprises the heavy chain variable domain sequence of SEQ ID NO: 24 and the light chain variable domain sequence of SEQ ID NO: 46.

In some embodiments, the antibody, or antigen binding fragment CDRH1 comprises a sequence as set forth in SEQ ID NO: 62, CDRH2 comprises a sequence as set forth in SEQ ID NO: 64, CDRH3 comprises a sequence as set forth in SEQ ID NO: 66, CDRL1 comprises a sequence as set forth in SEQ ID NO: 84, CDRL2 comprises a sequence as set forth in SEQ ID NO: 86, and CDRL3 comprises a sequence as set forth in SEQ ID NO: 88.

In some embodiments, the antibody, or antigen binding fragment comprises the heavy chain variable domain sequence of SEQ ID NO: 68. In some embodiments, the antibody, or antigen binding fragment comprises the light chain variable domain sequence of SEQ ID NO: 90. In some embodiments, the antibody, or antigen binding fragment comprises the heavy chain variable domain sequence of SEQ ID NO: 68 and the light chain variable domain sequence of SEQ ID NO: 90.

In some aspects, the disclosure provides an antibody or antigen binding fragment that specifically binds to a cell-surface exposed plectin-1, wherein the antibody or antigen binding fragment comprises a heavy chain variable region having a sequence set forth as: SEQ ID NO: 24 or SEQ ID NO: 68. In some embodiments, the antibody or antigen binding fragment further comprises a light chain variable region having a sequence set forth as: SEQ ID NO: 46 or SEQ ID NO: 90.

In some embodiments, the antibody comprises a heavy chain variable region having a sequence set forth as: SEQ ID NO 24 and a light chain variable region having a sequence set forth as: SEQ ID NO: 46.

In some embodiments, the antibody comprises a heavy chain variable region having a sequence set forth as: SEQ ID NO 68 and a light chain variable region having a sequence set forth as: SEQ ID NO: 90.

In some aspects, the disclosure provides an antibody that comprises a heavy chain variable region having a sequence set that shares at least 85% identity with SEQ ID NO: 15 and a light chain variable region that shares at least 85% identity with SEQ ID NO: 37. In some aspects, the disclosure provides an antibody that comprises a heavy chain variable region having a sequence set that shares at least 90% (e.g., at least 95%, at least 96%, at least 97%, at least 98%, or at least 99%) identity with SEQ ID NO: 15 and a light chain variable region that shares at least 90% (e.g., at least 95%, at least 96%, at least 97%, at least 98%, or at least 99%) identity with SEQ ID NO: 37.

In some aspects, the disclosure provides an antibody that comprises a heavy chain variable region having a sequence set that shares at least 85% identity with SEQ ID NO: 59 and a light chain variable region that shares at least 85% identity with SEQ ID NO: 81. In some aspects, the disclosure provides an antibody that comprises a heavy chain variable region having a sequence set that shares at least 90% (e.g., at least 95%, at least 96%, at least 97%, at least 98%, or at least 99%) identity with SEQ ID NO: 59 and a light chain variable region that shares at least 90% (e.g., at least 95%, at least 96%, at least 97%, at least 98%, or at least 99%) identity with SEQ ID NO: 81.

In some embodiments, an antibody, or antigen binding fragment described by the disclosure comprises a heavy chain constant domain having a sequence as set forth in SEQ ID NO: 15 or SEQ ID NO: 59.

In some embodiments, an antibody, or antigen binding fragment as described by the disclosure comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains.

In some embodiments, an antibody, or antigen binding fragment described by the disclosure is a monoclonal antibody, a humanized antibody, a diabody, a chimeric antibody, a Fab fragment, a F(ab')2 fragment, an affibody, or an Fv fragment.

In some embodiments, the disclosure relates to antibody-drug conjugates targeted against plectin-1. In some embodiments, an antibody described by the disclosure (e.g., an anti-plectin-1 antibody) is coupled to a targeted agent. In some embodiments, the targeted agent is a detectable moiety. In some embodiments, the detectable moiety is selected from the group consisting of a radioactive isotope, a magnetic compound, an x-ray absorber, a chemical compound, a biological tag, and a fluorescent molecule.

In some embodiments, the targeted agent is a therapeutic agent. In some embodiments, the therapeutic agent is a cytotoxic moiety or an immunomodulatory moiety.

In some embodiments, the antibody is coupled to the targeted agent via a linker. In some embodiments, the linker is a flexible amino acid sequence. In some embodiments, the linker is a photolinker.

In some embodiments, the targeted agent comprises a physiologically inert nanoparticle. In some embodiments, the nanoparticle is magnetic, fluorescent, or radioactive. In some embodiments, the targeted agent comprises a fluorochrome.

In some aspects, the disclosure provides an antibody, or antigen binding fragment, that competes or cross-competes for binding to an amino acid sequence set forth as: SEQ ID NO: 92 with an antibody, or antigen binding fragment as described by the disclosure (e.g., an anti-plectin-1 antibody). In some embodiments, the antibody or antigen binding fragment competes or cross-competes with an equilibrium dissociation constant, Kd, of less than $10^{-6}$ M between the antibody or antigen binding fragment, and its antigen.

In some aspects, the disclosure provides a composition comprising an antibody as described by the disclosure (e.g., an anti-plectin-1 antibody), optionally further comprising a pharmaceutically acceptable excipient.

In some aspects, the disclosure provides an isolated nucleic acid encoding a protein comprising three complementarity determining regions (CDRs): CDRH1, CDRH2, and CDRH3, wherein CDRH3 comprises a sequence as set forth in SEQ ID NO: 22. In some embodiments, CDRH1 comprises a sequence as set forth in SEQ ID NO: 18. In some embodiments, CDRH2 comprises a sequence as set forth in SEQ ID NO: 20.

In some aspects, the disclosure provides an isolated nucleic acid encoding a protein comprising three complementarity determining regions (CDRs): CDRL1, CDRL2, and CDRL3, wherein CDRL3 comprises a sequence as set forth in SEQ ID NO: 44. In some embodiments, CDRL1 comprises a sequence as set forth in SEQ ID NO: 40. In some embodiments, CDRL2 comprises a sequence as set forth in SEQ ID NO: 42.

In some aspects, the disclosure provides an isolated nucleic acid encoding a protein comprising three complementarity determining regions (CDRs): CDRH1, CDRH2, and CDRH3, wherein CDRH3 comprises a sequence as set forth in SEQ ID NO: 66. In some embodiments, CDRH1 comprises a sequence as set forth in SEQ ID NO: 62. In some embodiments, CDRH2 comprises a sequence as set forth in SEQ ID NO: 64.

In some aspects, the disclosure provides an isolated nucleic acid encoding a protein comprising three complementarity determining regions (CDRs): CDRL1, CDRL2, and CDRL3, wherein CDRL3 comprises a sequence as set forth in SEQ ID NO: 88. In some embodiments, CDRL1 comprises a sequence as set forth in SEQ ID NO: 84. In some embodiments, CDRL2 comprises a sequence as set forth in SEQ ID NO: 86.

In some aspects, the disclosure provides an isolated nucleic acid comprising a sequence as set forth in a sequence selected from the group consisting of SEQ ID NO: 15, 24, 37, 46, 59, 68, 81, or 90.

In some aspects, the disclosure provides an isolated cell (e.g., a host cell) comprising a nucleic acid as described by the disclosure. In some embodiments, the isolated cell is a bacterial cell, a yeast cell, a mammalian cell, or an insect cell. In some embodiments, the cell is a hybridoma cell.

In some aspects, the disclosure provides a method for targeting an agent to a cancer cell in a subject, the method comprising administering to the subject an antibody or composition as described by the disclosure (e.g., an anti-plectin-1 antibody or a composition comprising an anti-plectin-1 antibody), coupled to a targeted agent, wherein the antibody binds to plectin-1 on the surface of the cancer cell in the subject.

In some aspects, the disclosure provides a method for treating cancer, the method comprising administering to a subject having cancer an effective amount an antibody or composition as described by the disclosure (e.g., an anti-plectin-1 antibody or a composition comprising an anti-plectin-1 antibody).

In some aspects, the disclosure provides a method for detecting a cancer cell, the method comprising administering to a subject having cancer an effective amount of the method comprising administering to the subject an antibody or composition as described by the disclosure (e.g., an anti-plectin-1 antibody or a composition comprising an anti-plectin-1 antibody).

In some embodiments of methods described by the disclosure, the antibody or composition is administered at a dose in a range of 1 ng/kg and 100 mg/kg.

In some embodiments of methods described by the disclosure, the cancer cell is an ovarian cancer cell, esophageal cancer cell, head and neck squamous cell carcinoma cancer cell, or pancreatic cancer cell. In some embodiments, the cancer cell is a pancreatic ductal adenocarcinoma cell. In some embodiments of methods described by the disclosure, the subject is a mammal, optionally a human.

BRIEF DESCRIPTION OF DRAWINGS

FIGS. 4A-4B show representative confocal images of L3.6pl after staining of PAb1 (FIG. 4A) and IgG ctrl (FIG. 4B) merged with endosomal marker Lamp-1. Staining of Lamp-1 (FIG. 4C), PAb1 (FIG. 4D) and co-localization of LAMP-1 and PAb1 (FIG. 4E) are shown. A significant portion of PAb1 merged with Lamp-1 whereas IgG control did not.

FIG. 5A shows fluorescent minus one (FMO) flow cytometry data of L3.6pl cells. FIG. 5B shows L3.6pl AnnexinV positive cells after 72 h control IgG treatment. FIG. 5C shows L3.6pl AnnexinV positive cells after 72 h PAb1 treatment. FIG. 5D shows L3.6pl cancer cells experienced significantly more apoptosis after PAb1 treatment compared to control IgG (D).*, p<0.05.

FIG. 6A shows confocal microscopy images of YapC after tubulin staining without treatment. FIG. 6B shows confocal microscopy images of YapC after tubulin staining 10 min. post monomethyl auristatin E (MMAE) treatment. FIG. 6C shows confocal microscopy images of YapC after tubulin staining 24 h post PAb1 treatment. FIG. 6D shows a decrease of anisotropy in cells treated with PAb1 compared to non-treated controls.

FIG. 7A shows confocal microscopy images of YapC cells after tubulin staining. FIG. 7B shows confocal microscopy images of YapC cells after PAb1 staining. FIG. 7C shows co-localization (arrows) of tubulin staining and PAb1 staining.

FIG. 8A shows that after 11 days of treatment, tumor volume is significantly lower in mice administered 3 mg/kg PAb1 than control IgG mice. 1 mg/kg PAb1 treatment group elicited a significant reduction of tumor volume at day 14. The two higher doses of PAb1 showed a significantly lower tumor volume compared to 0.3 mg/kg group. *, p<0.05, IgG vs 3 mg/kg PAb1; #, p<0.05, IgG vs 1 mg/kg PAb1; °, p<0.05, 0.3 vs 3 mg/kg PAb1; •, p<0.05, 0.3 vs 1 mg/kg PAb1. FIGS. 8C, 8D, and 8E show a PAb1 3 mg/kg treatment group mouse at Day 0, Day 14, and Day 25. FIG. 8B shows the average body weight of the animal of each group. Note that the animal did not lose weight during the entire duration of the treatment.

DETAILED DESCRIPTION

Antibodies that Bind Plectin-1

Figure 1:
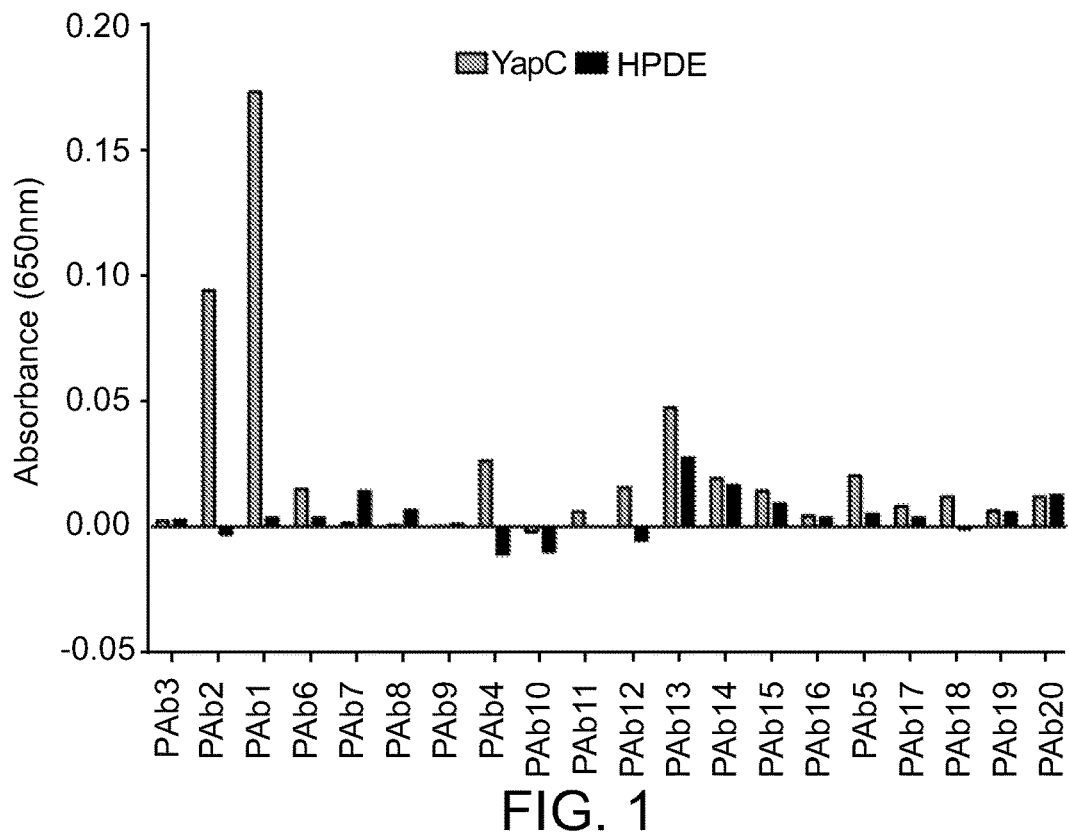
FIG. 1 shows the in vitro validation of different clones on YapC- or HPDE-coated plates.

The present disclosure provides antibodies and antigen binding fragments that bind to plectin-1 on the surface of cancer cells. The monoclonal antibodies of the disclosure may be murine, humanized or chimeric or in other forms. A detailed description of the antibodies of the disclosure as well as methods for the production and identification of the antibodies of the disclosure is provided herein.

Plectin-1 is a high molecular weight protein (500 kDa) that links intermediate filaments to microtubules and microfilaments, in addition to anchoring the cytoskeleton the plasma and nuclear membranes (reviewed in Sonnenberg, et al., Exp Cell Res 313:2189-2203 (2007)).

Generally, plectin-1 levels are low in normal pancreatic ductal cells but its expression is upregulated in cells having certain cancers (e.g., precursor pancreatic intraepithelial neoplasis (PanINs), pancreatic ductal adenocarcinoma cells (PDACs), ovarian cancer cells, etc.). Plectin-1 exhibits distinct cytoplasm and nuclear localization in normal fibroblasts, whereas an aberrant expression on the cell membrane is observed in cells having certain cancers (e.g., PDACs). Altered subcellular localization of plectin-1 has also been observed in an autoimmune condition, paraneoplastic pemphigus, and in the associated lymphoproliferative neoplasm, Castleman's disease (Aho et al., J Invest Dermatol 113:422-423 (1999)). Plectin-1 also has important roles in signal transduction. Thus, plectin-1 in cells having certain cancers (e.g., precursor pancreatic intraepithelial neoplasis (PanINs), pancreatic ductal adenocarcinoma cells (PDACs), ovarian cancer cells, etc.) may have an impact on signaling pathways that regulate cell migration, polarity and energy metabolism related to carcinogenesis. Accordingly, in some embodiments, the disclosure provides antibodies and antigen binding fragments that bind to plectin-1 on the surface of cancer cells.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H$1-3), and a hinge region. The $C_H$ domain most proximal to $V_H$ is designated as $C_H1$. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

In some embodiments, anti-plectin-1 antibodies of the present disclosure and the nucleic acid molecules of the present disclosure that encode the antibodies include the CDR amino acid and nucleic acid sequences shown in Table 1 below.

shown in Table 1. The disclosure also includes any nucleic acid sequence that encodes a CDRH1, CDRH2, CDRH3, CDRL1, CDRL2, or CDRL3 as provided for any one of the antibodies shown in Table 1. Antibody heavy and light chain CDR3 domains may play a particularly important role in the binding specificity/affinity of an antibody for an antigen. Accordingly, the anti-plectin-1 antibodies of the disclosure, or the nucleic acid molecules thereof, may include at least the heavy and/or light chain CDR3s of antibodies as shown in Table 1 or as set forth by SEQ ID NOs: 15, 22, 24, 37, 44, 46, 59, 66, 68, 81, 88 or 90.

The complete amino acid and nucleic acid sequences for the heavy chain variable region and light chain variable region of the antibodies listed in Table 2.

TABLE 2

| Antibody | Heavy Chain Variable Region | Light Chain Variable Region |
|---|---|---|
| PAb2 | | |
| Amino acid: | SEQ ID NO: 24 | SEQ ID NO: 46 |
| Nuc. Acid: | SEQ ID NO: 13 | SEQ ID NO: 35 |
| PAb1 | | |
| Amino acid: | SEQ ID NO: 68 | SEQ ID NO: 90 |
| Nuc. Acid: | SEQ ID NO: 57 | SEQ ID NO: 79 |

In some embodiments, anti-plectin antibodies of the disclosure include any antibody that includes a heavy chain variable domain or a light chain variable domain or both as shown in Table 1, or as described in the sequence listing of this disclosure (e.g., SEQ ID NOs: 15, 24, 37, 46, 59, 68, 81, or 90). The disclosure also includes any nucleic acid molecule encoding an antibody that includes a heavy chain variable domain or a light chain variable domain nucleic acid sequence, or both, as shown in Table 1 or as described in the sequence listing of this disclosure (e.g., SEQ ID NOs: 4, 13, 26, 35, 48, 57, 70, or 79).

Anti-plectin-1 antibodies of this disclosure may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibodies may include suitable constant

TABLE 1

| | Antibody | | | | | |
|---|---|---|---|---|---|---|
| | CDRH1 | CDRH2 | CDRH3 | CDRL1 | CDRL2 | CDRL3 |
| Pab2 | | | | | | |
| Amino acid: | (SEQ ID NO: 18) | (SEQ ID NO: 20) | (SEQ ID NO: 22) | (SEQ ID NO: 40) | (SEQ ID NO: 42) | (SEQ ID NO: 44) |
| Nuc. Acid: | (SEQ ID NO: 7) | (SEQ ID NO: 9) | (SEQ ID NO: 11) | (SEQ ID NO: 29) | (SEQ ID NO: 31) | (SEQ ID NO: 33) |
| Pab1 | | | | | | |
| Amino acid: | (SEQ ID NO: 62) | (SEQ ID NO: 64) | (SEQ ID NO: 66) | (SEQ ID NO: 84) | (SEQ ID NO: 86) | (SEQ ID NO: 88) |
| Nuc. Acid: | (SEQ ID NO: 51) | (SEQ ID NO: 53) | (SEQ ID NO: 55) | (SEQ ID NO: 73) | (SEQ ID NO: 75) | (SEQ ID NO: 77) |

In some embodiments, anti-plectin-1 binding agents (e.g., anti-plectin-1 antibodies) of the disclosure include any antibody or antigen binding fragment that includes a CDRH1, CDRH2, CDRH3, CDRL1, CDRL2, or CDRL3, or combinations thereof, as provided for any one of the antibodies shown in Table 1. In some embodiments, anti-plectin-1 binding agents include the CDRH1, CDRH2, CDRH3, CDRL1, CDRL2, and CDRL3 of any one of the antibodies regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with constant regions known in the art. In some embodiments, anti-plectin-1 antibodies of the disclosure comprise a heavy chain constant region comprising a sequence represented by SEQ ID NOs: 4, 14, 26, 36, 48, 58, 70, or 80.

In certain embodiments, the $V_H$ and/or $V_L$ domains may be reverted to germline sequence, e.g., the FR of these domains are mutated using conventional molecular biology techniques to match those produced by the germline cells. In other embodiments, the FR sequences remain diverged from the consensus germline sequences.

In some embodiments, anti-plectin-1 antibodies or antigen binding fragments may or may not include the framework region of the antibodies, for example as set forth in SEQ ID NOs: 6, 8, 10, 12, 17, 19, 21, 23, 28, 30, 32, 34, 39, 41, 43, 45, 50, 52, 54, 56, 61, 63, 65, 67, 72, 74, 76, 78, 83, or 85. In some embodiments, anti-plectin-1 antibodies are murine antibodies. In some embodiments, anti-plectin-1 antibodies are chimeric or humanized antibodies.

It should be appreciated that, in some embodiments, the disclosure contemplates variants (e.g., homologs) of amino acid and nucleic acid sequences for the heavy chain variable region and light chain variable region of the antibodies. "Homology" refers to the percent identity between two polynucleotides or two polypeptide moieties. The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. For example, in some embodiments, nucleic acid sequences sharing substantial homology are at least 90%, at least 91%, at least 92% at least 93%, at least 94%, at least 95%, at least 96% at least 97%, at least 98% at least 99% sequence identity. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. For example, in some embodiments, highly conserved proteins share at least 85%, at least 90%, at least 91%, at least 92% at least 93%, at least 94%, at least 95%, at least 96% at least 97%, at least 98% at least 99% identity. In some cases, highly conserved may refer to 100% identity. Identity is readily determined by one of skill in the art by, for example, the use of algorithms and computer programs known by those of skill in the art.

In some embodiments, an anti-plectin-1 antibodies of the disclosure can bind to plectin-1 with high affinity, e.g., with a Kd less than $10^{-7}$ M, $10^{-8}$ M, $10^{-9}$ M, $10^{-10}$ M, $10^{-11}$ M or lower. For example, anti-plectin-1 antibodies or antigen binding fragments thereof can bind to plectin-1 with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to plectin-1 and that have an affinity of 50 nM or lower (e.g., 20 nM or lower, 10 nM or lower, 500 pM or lower, 50 pM or lower, or 5 pM or lower). The affinity and binding kinetics of the anti-plectin-1antibody can be tested using any method known in the art including but not limited to biosensor technology (e.g., OCTET or BIACORE).

As used herein, the term "antibody" generally refers to an immunoglobulin. All derivatives thereof which maintain or possess specific binding ability are also provided herein. An antibody preparation may be monoclonal or polyclonal.

As used herein, the term "antibody fragment" or "antigen binding fragment" refers to any derivative of an antibody which is less than full-length. Generally, an antigen binding fragment retains at least a significant portion of the full-length antibody's specific binding ability. Examples of antigen binding fragments include, but are not limited to, Fab, Fab', F(ab')2, scFv, Fv, dsFv diabody, affibodies, and Fd fragments. Antigen binding fragments may be produced by any appropriate means. For instance, an antigen binding fragment may be enzymatically or chemically produced by fragmentation of an intact antibody or it may be recombinantly produced from a gene encoding the partial antibody sequence. Alternatively, an antigen binding fragment may be wholly or partially synthetically produced. An antigen binding fragment may optionally be a single chain antibody fragment. Alternatively, a fragment may comprise multiple chains which are linked together, for instance, by disulfide linkages. An antigen binding fragment may also optionally be a multimolecular complex. A functional antigen binding fragment will typically comprise at least about 50 amino acids and more typically will comprise at least about 200 amino acids.

Single-chain Fvs (scFvs) are recombinant antigen binding fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

Diabodies are dimeric scFvs. The components of diabodies typically have shorter peptide linkers than most scFvs, and they show a preference for associating as dimers.

A Fv fragment is an antigen binding fragment which consists of one VH and one VL domain held together by noncovalent interactions. The term dsFv is used herein to refer to an Fv with an engineered intermolecular disulfide bond to stabilize the VH-VL pair.

A F(ab')2 fragment is an antigen binding fragment essentially equivalent to that obtained from immunoglobulins (typically IgG) by digestion with an enzyme pepsin at pH 4.0-4.5. The fragment may be recombinantly produced.

A Fab fragment is an antigen binding fragment essentially equivalent to that obtained by reduction of the disulfide bridge or bridges joining the two heavy chain pieces in the F(ab')2 fragment. The Fab' fragment may be recombinantly produced.

A Fab fragment is an antigen binding fragment essentially equivalent to that obtained by digestion of immunoglobulins (typically IgG) with the enzyme papain. The Fab fragment may be recombinantly produced. The heavy chain segment of the Fab fragment is the Fd piece.

An affibody is a small protein comprising a three-helix bundle that functions as an antigen binding molecule (e.g., an antibody mimetic). Generally, affibodies are approximately 58 amino acids in length and have a molar mass of approximately 6 kDa. Affibody molecules with unique binding properties are acquired by randomization of 13 amino acids located in two alpha-helices involved in the binding activity of the parent protein domain. Specific affibody molecules binding a desired target protein can be isolated from pools (libraries) containing billions of different variants, using methods such as phage display.

Production of Antibodies that Bind Plectin-1

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228: 1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., plectin-1) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., made chimeric, using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

Antibodies can also be humanized by methods known in the art. For example, monoclonal antibodies with a desired binding specificity can be commercially humanized (Scotgene, Scotland; and Oxford Molecular, Palo Alto, Calif.). Fully humanized antibodies, such as those expressed in transgenic animals are within the scope of the invention (see, e.g., Green et al. (1994) Nature Genetics 7, 13; and U.S. Pat. Nos. 5,545,806 and 5,569,825).

For additional antibody production techniques, see Antibodies: A Laboratory Manual, Second Edition. Edited by Edward A. Greenfield, Dana-Farber Cancer Institute, ©2014. The present disclosure is not necessarily limited to any particular source, method of production, or other special characteristics of an antibody.

Some aspects of the present invention relate to isolated cells (e.g., host cells) transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured according to techniques known in the art to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As used herein, "hybridoma cell" refers to an immortalized cell derived from the fusion of B lymphoblasts with a myeloma fusion partner. For preparing monoclonal antibody-producing cells (e.g., hybridoma cells), an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Kochler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and are well known in the art. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Some aspects of the disclosure relate to antibody-drug conjugates targeted against plectin-1. As used herein, "antibody drug conjugate" refers to molecules comprising an antibody, or antigen binding fragment thereof, linked to a targeted molecule (e.g., a biologically active molecule, such as a therapeutic molecule, and/or a detectable label). Accordingly, in some embodiments, antibodies or antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of plectin-1. The detectable substance may be coupled or conjugated either directly to the polypeptides of the disclosure or indirectly, through an intermediate (such as, for example, a linker known in the art) using techniques known in the art. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the anti-plectin-1 antibodies of the disclosure or indirectly, through an intermediate (such as, for example, a linker known in the art) using techniques known in the art. Anti-plectin-1 antibodies conjugated to a detectable substance may be used for diagnostic assays as described herein.

In some embodiments, antibodies or antigen binding fragments of the disclosure may be modified with a therapeutic moiety (e.g., therapeutic agent). As used herein, the term "therapeutic agent" refers to chemicals or drugs or proteins that are able to inhibit cell function, inhibit cell replication or kill mammalian cells, preferably human cells. Examples of therapeutic agents include but are not limited to cytotoxic moieties, radioisotopes, molecules of plant, fungal, or bacterial origin (e.g., plant-derived toxins (e.g., secondary metabolites), glycosides, antimicrobial compounds (e.g., streptomycin, penicillin, etc.), biological proteins (e.g., protein toxins), particles (e.g., recombinant viral particles, e.g., via a viral coat protein), or mixtures thereof. The therapeutic agent can be an intracellularly active drug or other agent, such as short-range radiation emitters, including, for example, short-range, high-energy alpha-emitters (e.g., $^{131}$I).

In some embodiments, the therapeutic agent is an immunomodulatory moiety (e.g., immunomodulatory agent). As used herein, "immunomodulatory agent" refers to a compound or molecule that increases or decreases the immune response of a subject in response to the agent. For example, an immunomodulatory agent may enhance the immune response of a subject to a tumor, e.g., increase the level of inflammatory cytokines such as interleukin-1 (IL-1), and tumor necrosis factor-alpha (TNF-α). Examples of immunomodulatory agents that increase the immune response of a subject include granulocyte colony-stimulating factor (G-CSF), interferons, imiquimod, cellular membrane fractions from bacteria, certain interleukins and cytokines (e.g., IL-1β, IL-6, and TNF-α), and immune checkpoint inhibitors (e.g., PD-1 inhibitors, PD1-L inhibitors, etc.). In some embodiments, an immunomodulatory agent may decrease the immune response of a subject (e.g., mediate or achieve immunosuppression). Examples of immunosuppressive immunomodulators include but are not limited to immunosuppressive drugs (e.g., glucococorticoids, cytostatics, anti-inflammatory monoclonal antibodies (e.g., anti-IL-2 receptor antibodies), and drugs targeting immunophilins (e.g., ciclosporin, sirolimus, etc.). In some embodiments, the antibody is coupled to the targeted agent via a linker. As used herein, the term "linker" refers to a molecule or sequence, such as an amino acid sequence, that attaches, as in a bridge, one molecule or sequence to another molecule or sequence. "Linked," "conjugated," or "coupled" means attached or bound by covalent bonds, or non-covalent bonds, or other bonds, such as van der Waals forces. Antibodies described by the disclosure can be linked to the targeted agent (e.g., therapeutic moiety or detectable moiety) directly, e.g., as a fusion protein with protein or peptide detectable moieties (with or without an optional linking sequence, e.g., a flexible linker sequence) or via a chemical coupling moiety. A number of such coupling moieties are known in the art, e.g., a peptide linker or a chemical linker, e.g., as described in International Patent Application Publication No. WO 2009/036092. In some embodiments, the linker is a flexible amino acid sequence. Examples of flexible amino acid sequences include glycine and serine rich linkers, which comprise a stretch of two or more glycine residues, (e.g., GGGS; SEQ ID NO: 93). In some embodiments, the linker is a photolinker. Examples of photolinkers include ketyl-reactive benzophenone (BP), anthraquinone (AQ), nitrene-reactive nitrophenyl azide (NPA), and carbene-reactive phenyl-(trifluoromethyl)diazirine (PTD).

In some embodiments, the targeted agent comprises a physiologically inert nanoparticle. Examples of nanoparticles developed and used for imaging cancer cells, include magnetic nanoparticles and their magnetofluorescent analogues (see, e.g., Weissleder et al., Nat. Biotechnol., 19:316-317 (2001); McCarthy et al., Nanomedicine, 2:153-167 (2007); Hogemann et al., Bioconjug. Chem., 11:941-946 (2000), and Josephson et al., Bioconjug. Chem., 10:186-191 (1999)) which are contemplated for use with isolated peptide ligands and phage displayed peptides. Multimodal nanoparticles are known that incorporate both magnetic and fluorescent molecules within the same molecule and are used for fluorescent microscopy (which detects the fluorescent part of this very small particle) and MRI (which detects its magnetic portion). In some embodiments, the nanoparticle is magnetic, fluorescent, or radioactive. In some embodiments, the targeted agent comprises a fluorochrome.

Pharmaceutical Compositions

In some aspects, the disclosure relates to pharmaceutical compositions comprising anti-plectin-1 antibodies. In some embodiments, the composition comprises an anti-plectin-1 antibody and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., an anti-plectin-1 antibody or antibody drug conjugate comprising an anti-plectin-1 antibody and a targeted agent). In general, an "effective amount" of an active agent refers to an amount sufficient to elicit the desired biological response (e.g., killing of a cancerous cell or suppression of tumor growth). An effective amount of an agent may vary depending on such factors as the desired biological endpoint, the pharmacokinetics of the compound, the disease being treated (e.g., certain cancers characterized by surface expression of plectin-1), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, an anti-plectin-1 antibody or antibody drug conjugate comprising an anti-plectin-1 antibody and a targeted agent) is an amount sufficient to ameliorate at least one adverse effect associated with cancer (e.g., tumor growth, metastasis). The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

In some cases, compounds of the disclosure are prepared in a colloidal dispersion system. Colloidal dispersion systems include lipid-based systems including oil-in-water emulsions, micelles, mixed micelles, and liposomes. In some embodiments, a colloidal system of the disclosure is a liposome. Liposomes are artificial membrane vessels which are useful as a delivery vector in vivo or in vitro. It has been shown that large unilamellar vesicles (LUVs), which range in size from 0.2-4.0 µm can encapsulate large macromolecules.

Liposomes may be targeted to a particular tissue by coupling the liposome to a specific ligand such as a monoclonal antibody, sugar, glycolipid, or protein. Ligands which may be useful for targeting a liposome to, for example, an smooth muscle cell include, but are not limited to: intact or fragments of molecules which interact with smooth muscle cell specific receptors and molecules, such as antibodies, which interact with the cell surface markers of cancer cells. Such ligands may easily be identified by binding assays well known to those of skill in the art. In still other embodiments, the liposome may be targeted to a tissue by coupling it to an antibody known in the art.

Compounds described by the disclosure may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus* Calmette-Guérin, *Shigella, Lactobacillus*); live viral vectors (e.g., Vaccinia, adenovirus, Herpes simplex); microspheres; nucleic acid vaccines; polymers (e.g., carboxymethylcellulose, chitosan); polymer rings; proteosomes; sodium fluoride; transgenic plants; virosomes; and, virus-like particles.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to the formulations described herein, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Treatment Methods

Aspects of the disclosure relate to the discovery of antibodies that specifically bind to plectin-1 on the surface of certain cancer cells. In some embodiments, binding of an anti-plectin-1 antibody as described by the disclosure to certain cancer cells induces death (e.g., triggers apoptosis) of the cells. Without wishing to be bound by any particular theory, antibodies described by the disclosure are useful, in some embodiments, for treating cancer characterized by surface expression of plectin-1. As used herein, "treating cancer" refers to decreasing the number of cancer cells in a patient, slowing the growth of cancer cells in a patient, reducing the metastasis of cancer cells in a patient and includes any type of response for either relieving cancer symptoms or increasing the life-span of a patient.

Examples of cancers characterized by surface expression of plectin-1 include but are not limited to ovarian cancer cell, esophageal cancer cell, head and neck squamous cell carcinoma cancer cell, or pancreatic cancer cell (e.g., pancreatic ductal adenocarcinoma (PDAC)). However, it should be appreciated that other cancers (such as lung cancer, bladder cancer, breast cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, stomach cancer, prostate cancer, testicular cancer, cervical cancer, endometrial cancer, uterine cancer, colon cancer, colorectal, gastric cancer, kidney cancer, bladder cancer, lymphoma cancer, spleen cancer, thymus cancer, thyroid cancer, brain cancer, neuronal cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, white blood cell cancer (e.g., lymphoma, leukemia, etc.), hereditary non-polyposis cancer (HNPC), colitis-associated cancer, etc. Cancers are further exemplified by sarcomas (such as osteosarcoma and Kaposi's sarcoma) may be treated using anti-plectin-1 antibodies described by the disclosure.

In some aspects, the disclosure provides a method for treating cancer, the method comprising administering to a subject having cancer an effective amount an antibody or composition as described by the disclosure (e.g., an anti-plectin-1 antibody or a composition comprising an anti-plectin-1 antibody). In some embodiments, the subject is a mammal. In some embodiments, the subject is a human.

Generally, antibodies and pharmaceutical compositions of the disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

The pharmaceutical compositions containing an anti-plectin-1 antibody and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the anti-plectin-1 antibody and/or other therapeutic agent can be administered to a subject by any mode that delivers the agent to the desired surface, e.g., mucosal, systemic.

Administering the pharmaceutical composition of the present disclosure may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner. For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The anti-plectin-1 antibodies and compositions described by the disclosure can be administered to a subject (e.g., a subject having cancer) on multiple occasions. In some embodiments, the number of occasions in which an antibody or composition of the disclosure is delivered to a subject is in a range of 2 to 10 times (e.g., 2, 3, 4, 5, 6, 7, 8, 9, or 10 times). In some embodiments, a heterologous nucleic acid is delivered to a subject more than 10 times.

In some embodiments, a dose of an antibody or composition of the disclosure is administered to a subject no more than once per calendar day (e.g., a 24-hour period). In some embodiments, a dose of an antibody or composition of the disclosure is administered to a subject no more than once per 2, 3, 4, 5, 6, or 7 calendar days. In some embodiments, a dose of an antibody or composition of the disclosure is administered to a subject no more than once per calendar week (e.g., 7 calendar days). In some embodiments, a dose of an antibody or composition of the disclosure is administered to a subject no more than bi-weekly (e.g., once in a two calendar week period). In some embodiments, a dose of an antibody or composition of the disclosure is administered to a subject no more than once per calendar month (e.g., once in 30 calendar days). In some embodiments, a dose of an antibody or composition of the disclosure is administered to a subject no more than once per six calendar months. In some embodiments, a dose of an antibody or composition of the disclosure is administered to a subject no more than once per calendar year (e.g., 365 days or 366 days in a leap year).

Immunoassays

In some embodiments, the disclosure relates to a method for detecting a plectin-1 on the surface of cells, e.g., cancer cells, in situ or in vitro. In some embodiments, the disclosure relates to a method for detecting plectin-1 on the surface of cells in a sample obtained from a subject. The sample may be obtained from a subject, for example, by extracting a tumor or portion thereof from a subject. In some embodiments, cells may be isolated from the tumor. However, in some embodiments, cells may be examined in the context of an isolated tumor.

In some embodiments, a method for detecting a plectin-1 in situ involve delivering to a subject a plectin-1 antibody or antigen binding fragment conjugated to a label (e.g., a radioactive label) under conditions in which the antibody or antigen binding fragment is able to form binding complexes with an accessible epitope of plectin-1 on cells, e.g., cancer cells, in the subject; and detecting the label in the subject (e.g., using autoradiography or other nuclear medicines detection techniques, including single photon emission computed tomography (SPECT), positron emission tomography (PET) and scintigraphy).

In some embodiments, a method for detecting a plectin-1 in a tumor sample obtained from a subject involve (a) contacting the sample with the antibody or antigen binding fragment under conditions suitable for binding of the antibody or antigen binding fragment to the antigen, if the antigen is present in the sample, thereby forming binding complexes; and (b) determining the level of the antibody or antigen binding fragment bound to the antigen (e.g., determining the level of the binding complexes), e.g., at the surface of a cell of the tumor.

As used herein a binding complex refers to a biomolecular complex of antibody or antigen binding fragments bound to antigen (e.g., plectin-1 protein). Binding complexes may comprise antibodies or antigen binding fragments with a single specificity or two or more antibodies or antigen binding fragments with different specificities. In one embodiment, a binding complex comprises two or more antibodies recognizing different antigenic sites on the same antigen. In some instances, an antibody or antigen binding fragment may be bound to an antigen, having bound to it other biomolecules such as RNA, DNA, polysaccharides or proteins. In one embodiment, a binding complex comprises two or more antibodies recognizing different antigens. In some embodiments, an antibody or antigen binding fragment in a binding complex (e.g., an immobilized antibody or antigen binding fragment bound to antigen), may itself by bound, as an antigen, to an antibody or antigen binding fragment (e.g., a detectably labeled antibody or antigen binding fragment). Thus, binding complexes may, in some instances, comprise multiple antigens and multiple antibodies or antigen binding fragments. Antigens present in binding complexes may or may not be in their native in situ conformation. In some embodiments, a binding complex is formed between an antibody or antigen binding fragment and a purified protein antigen, or isolated proteins comprising antigen, in which the antigen is not in its native in situ conformation. In some embodiments, a binding complex is formed between an antibody or antigen binding fragment and a purified protein antigen, in which the antigen is not in its native in situ conformation and is immobilized on solid support (e.g., a PVDF membrane). In some embodiments, a binding complex is formed with an antibody or antigen binding fragment and, for example, a cell surface protein that is present in situ in a native confirmation (e.g., on the surface of a cell). Antibodies or antigen binding fragments in binding complexes may or may not be detectably labeled. In some embodiments, binding complexes comprise detectably labeled antibodies or antigen binding fragments and non-labeled antibodies or antigen binding fragments. In some embodiments, binding complexes comprise detectably labeled antigen. In some embodiments, antibodies or antigen binding fragments, in binding complexes, are immobilized to one or more solid supports. In some embodiments, antigens, in binding complexes, are immobilized to one or more solid supports. Exemplary solid supports are disclosed herein and will be apparent to one of ordinary skill in the art. The foregoing examples of binding complexes are not intended to be limiting. Other examples of binding complexes will be apparent to one or ordinary skill in the art.

In any of the detection, diagnosis, and monitoring methods, the antibody, or antigen binding fragments, or antigen may be conjugated to a solid support surface, either directly or indirectly. Methods for conjugation to solid supports are standard and can be accomplished via covalent and non-covalent interactions. Non-limiting examples of conjugation methods include: adsorption, cross-linking, protein A/G-antibody interactions, and streptavidin-biotin interactions. Other methods of conjugation will be readily apparent to one of ordinary skill in the art.

In some aspects, the foregoing detection, diagnosis, and monitoring methods include comparing the level of the antibody or antigen binding fragment bound to the antigen (e.g., binding complexes) to one or more reference standards. The reference standard may be, for example, the level of a corresponding plectin-1 in a subject that does or does not have preeclampsia. In one embodiment, the reference standard is the level of plectin-1 detected in a sample that does not contain plectin-1 (e.g., a background level). Alternatively, a background level can be determined from a sample that contains a particular plectin-1, by contacting the sample with non-specific antibodies (e.g., antibodies obtained from non-immune serum). Then again, the reference standard may be the level of plectin-1 detected in a sample that does contain plectin-1 (e.g., a positive control). In some cases, the reference standard may be a series of levels associated with varying concentrations of plectin-1 in a sample and useful for quantifying the concentration of plectin-1 in the test sample. The foregoing examples of reference standards are not limiting and other suitable reference standard will be readily apparent to one of ordinary skill in the art.

Another embodiment relates to a diagnostic composition comprising any one of the above described antibodies, antigen binding fragments, polynucleotides, vectors or cells and optionally suitable means for detection. The antibodies or antigen binding fragments are, for example, suited for use in immunoassays in which they can be utilized in liquid phase or bound to a solid phase carrier. Examples of immunoassays which can utilize the antibody or antigen binding fragments are competitive and non-competitive immunoassays in either a direct or indirect format. Examples of such immunoassays are the Enzyme Linked Immunoassay (ELISA), radioimmunoassay (RIA), the sandwich (immunometric assay), flow cytometry, the western blot assay, immunoprecipitation assays, immunohistochemistry, immuno-microscopy, lateral flow immuno-chromatographic assays, and proteomics arrays. The antigens and antibodies or antigen binding fragments can be bound to many different solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

By a further embodiment, antibodies and antigen binding fragments provided herein may also be used in a method for evaluating plectin-1 expression in a subject by obtaining a biological sample from the subject which may be a blood sample, any other appropriate body fluid sample (e.g., lymph fluid), or a tissue sample (e.g., pancreatic tissue, ovarian tissue, tissue from the head or neck of a subject, breast tissue, lung tissue, etc.). The procedure may comprise contacting the sample (e.g., pancreatic tissue), or protein sample isolated therefrom, with an antibody, or antigen binding fragment, under conditions enabling the formation of binding complexes between antibody or antigen binding fragment and antigen. The level of such binding complexes may then be determined by methods known in the art.

In some embodiments, the biological sample is contacted with the antibody or antigen binding fragment under conditions suitable for binding of the antibody or antigen binding fragment to a plectin-1 protein, if the antigen is present in the sample, and formation of binding complexes consisting of antibody, or antigen binding fragment, bound to the antigen. This contacting step is typically performed in a reaction chamber, such as a tube, plate well, membrane bath, cell culture dish, microscope slide, and the like. In some embodiments, the antibody or antigen binding fragment is immobilized on a solid support. In some embodiments, the antigen is immobilized on a solid support. In some embodiments, the solid support is the surface of a the reaction chamber. In some embodiments, the solid support is of a polymeric membrane (e.g., nitrocellulose strip, Polyvinylidene Difluoride (PVDF) membrane, etc.). Other appropriate solid supports may be used.

In some embodiments, the antibody and antigen binding fragment is immobilized on the solid support prior to contacting with the antigen. In other embodiments, immobilization of the antibody and antigen binding fragment is performed after formation of binding complexes. In still other embodiments, antigen is immobilized on a solid support prior to formation of binding complexes. In some embodiments, a detection reagent is added to the reaction chamber to detect immobilized binding complexes. In some embodiments, the detection reagent comprises a detectably labeled secondary antibody directed against the antigen. In some embodiments, the primary antibody or antigen binding fragment is itself detectable labeled, and is thereby the detection reagent.

In one aspect, detection methods comprise the steps of immobilizing antibodies or antigen binding fragments to a solid support; applying a sample (e.g., a biological sample or isolated protein sample) to the solid support under conditions that permit binding of antigen to the antibodies or antigen binding fragment, if present in the sample; removing the excess sample from the solid support; applying detectably labeled antibodies or antigen binding fragments under conditions that permit binding of the detectably labeled antibodies or antigen binding fragments to the antigen-bound immobilized antibodies or antigen binding fragments; washing the solid support and assaying for the presence of label on the solid support.

In some embodiments, the antigen is immobilized on the solid support, such as a PVDF membrane, prior to contacting with the antibody and antigen binding fragment in a reaction chamber (e.g., a membrane bath). A detection reagent is added to the reaction chamber to detect immobilized binding complexes. In some embodiments, the detection reagent comprises a detectably labeled secondary antibody directed against the antigen. In some embodiments, the detection reagent comprises a detectably labeled secondary antibody directed against the primary antibody or antigen binding fragment. As disclosed herein, the detectable label may be, for example, a radioisotope, a fluorophore, a luminescent molecule, an enzyme, a biotin-moiety, an epitope tag, or a dye molecule. In some embodiments, the primary antibody or antigen binding fragment is itself detectable labeled, and is thereby the detection reagent. Suitable detectable labels are described herein, and will be readily apparent to one of ordinary skill in the art.

Accordingly, diagnostic kits, suitable for home or clinical use (point of care service), are provided that comprise (a) detectably labeled and/or non-labeled antibodies or antigen binding fragments, as antigen binding reagents (e.g., plectin-1 binding reagents); (b) a detection reagent; and, optionally, (c) complete instructions for using the reagents to detect antigens in a sample. In some embodiments, the diagnostic kit includes the antibody, or antigen binding fragment, and/or plectin-1 immobilized on a solid support. Any of the solid supports described herein are suitable for incorporation in the diagnostic kits. In a preferred embodiment, the solid support is the surface of a reaction chamber of a plate well. Typically, the plate well is in a multi-well plate having a number of wells selected from: 6, 12, 24, 96, 384, and 1536, but it is not so limited. In other embodiments, the diagnostic kits provide a detectably labeled antibody or antigen binding fragment. Diagnostic kits are not limited to these embodiments and other variations in kit composition will be readily apparent to one of ordinary skill in the art.

The present disclosure is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Expression and Purification of Human Plectin-1 in *E. coli*

Expression-ready constructs, both His-tagged vectors (15 mg/L, SEQ ID NO: 2) and GST-tagged vectors (30 mg/L, SEQ ID NO: 3), were used to generate monoclonal antibodies. To evaluate expression, the plasmids were transformed in strain B of *E. coli*. The trials were conducted in 4 mL test tubes, and the following variables were examined: temperature, expression time, and concentration of isopropyl β-D-1-thiogalactopyranoside (IPTG).

Cells were harvested by centrifugation. Cell pellets were lysed by sonication and target protein was obtained with one-step purification using a nickel column. Fractions were pooled and dialyzed against the storage buffer. Different storage buffers were used to determine which yielded the most stable protein with a concentration greater than 0.4 mg/mL. Proteins were analyzed by SDS-PAGE and Western blot using standard protocols to obtain molecular weight and purity measurements. The concentration of the protein was determined with a Bradford protein assay, using bovine serum albumin (BSA) as a standard.

Monoclonal Development of Anti-human Plectin-1 Protein

A specific panel of anti-human plectin-1 protein monoclonal antibodies which recognize the target protein (underlined in SEQ ID NO: 1; set forth in SEQ ID NO: 92) was developed.

First, five BALB/c mice were immunized with GenScript's MonoExpress immunization protocol and observed for two weeks.

Electrofusion was used to perform two fusions. The average fusion efficiency using this process is around 1 hybridoma/5000 B cells. The anticipated yield of hybridoma clones was $2 \times 10^4$, and the fused cells were plated into 96-well plates. An ELISA was performed to screen the fusion proteins for positive clones. Supernatants from the positive clones were then further screened by ELISA against the target protein. 10*His-tagged protein was used as the counter screen. Selected clones were positive against the target protein and negative against the 10*His-tagged protein. The positive clones were expanded into 24-well plates coated with human recombinant Sec 8 (plectin-1 Section 8) and 2 mL of supernatant for each clone was collected before the cells were frozen for storage. Table 3 shows the $OD_{450nm}$ for cell lines grown on plates coated with human recombinant plectin-1 section 8.

TABLE 3

OD450 Results for Experimental Cell Lines

| Cell Line | OD 450 A | OD 450 B | Host Strain |
|---|---|---|---|
| PAb3 | 2.647 | 0.084 | |
| PAb2 | 2.428 | 0.082 | |
| PAb1 | 2.323 | 0.117 | |
| PAb6 | 2.484 | 0.093 | |
| PAb7 | 2.400 | 0.109 | |
| PAb8 | 2.257 | 0.085 | |
| PAb9 | 2.616 | 0.113 | MOUSE |
| PAb4 | 2.484 | 0.118 | |
| PAb10 | 2.326 | 0.132 | |
| PAb11 | 2.418 | 0.110 | |
| PC (antiserum 1:1k) | 2.254 | 0.215 | |
| PAb12 | 2.422 | 0.107 | |
| PAb13 | 2.223 | 0.093 | |
| PAb14 | 2.292 | 0.084 | |
| PAb15 | 2.498 | 0.086 | |
| PAb16 | 2.223 | 0.087 | |
| PAb5 | 2.453 | 0.097 | |
| PAb17 | 2.546 | 0.086 | |
| PAb18 | 2.589 | 0.098 | |
| PAb19 | 2.552 | 0.081 | |
| PAb20 | 2.558 | 0.073 | |
| NC (medium) | 0.068 | 0.073 | |

Positive primary clones from the two fusions were subcloned by limiting dilution to ensure the sub-clones were derived from a single parental cell. The clones were grown for three generations. The sub-clones were further screened by ELISA. Based on the results of the ELISA, two stable sub-clonal cell lines of each primary clone were cryopreserved.

Figure 2:
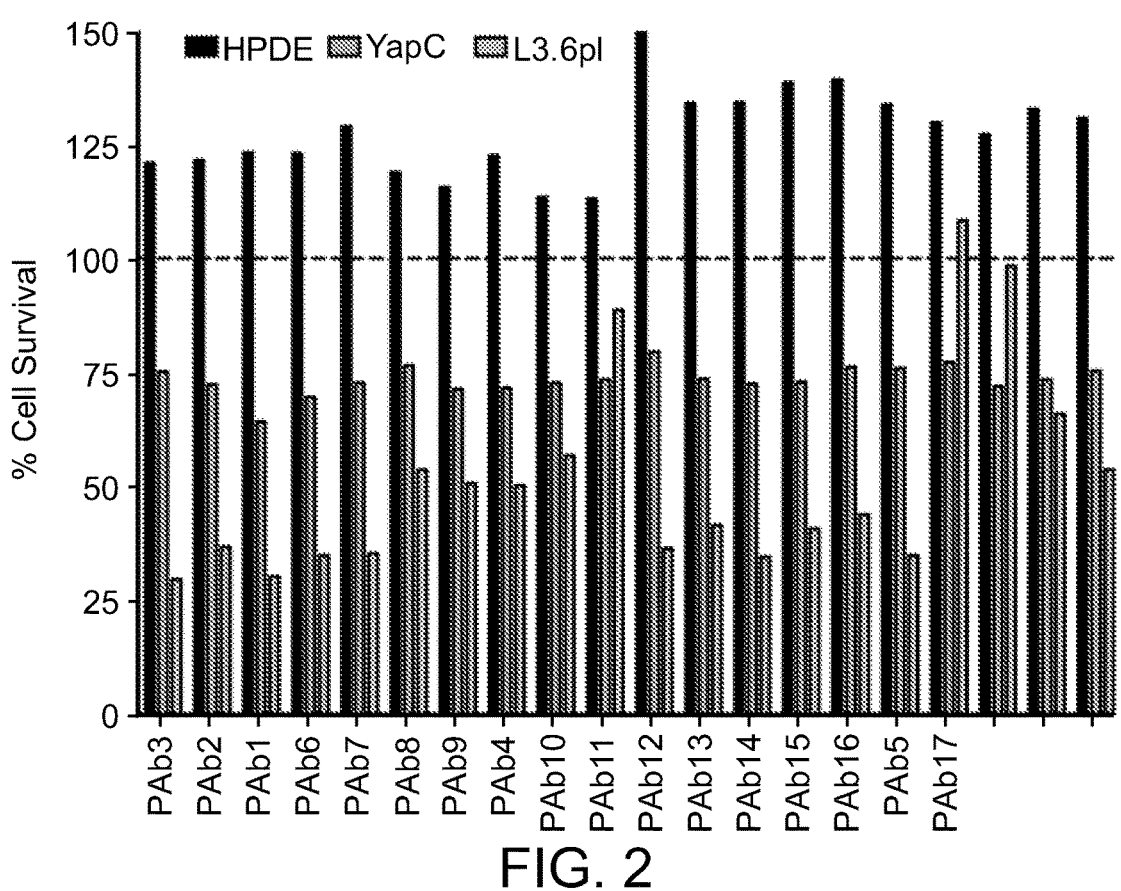
FIG. 2 shows further in vitro validation of the cell lines using a cell killing assay.

Clones PAb1 and PAb2, exhibited the highest specific plectin binding potential (FIG. 1). Clones PAb3, PAb4, and PAb5 also demonstrated ability to kill cancer cells (FIG. 2).

Roller bottles were used to produce the antibodies at a concentration of approximately 15 mg/L. The antibody proteins were further purified using protein A/G affinity column chromatography and dialyzed into PBS buffer for storage. For quality control, the antibodies underwent a purity test by SDS-PAGE, concentration determination by absorption at $OD_{280nm}$, and antigen reactivity by ELISA.

Selected antibodies were subjected to standard full length antibody sequencing. The antibodies underwent total RNA extraction, RT-PCR, and 5' RACE and 3' RACE PCR. The target PCR fragments of the variable and constant regions were gel-purified and cloned into sequencing vectors. At least five independent positive clones of each chain were sequenced in order to deduce the consensus sequence.

Monoclonal Antibody Sequencing of PAb1 and PAb2

PAb1 and PAb2 were sequenced using the following procedure. Total RNA was isolated from the hybridoma cells recovered by GenScript using TRIzol® reagent (Ambion, Cat. No.: 15596-026) and the procedure from the technical manual of TRIzol® reagent. The total RNA was then analyzed by agarose gel electrophoresis. Isotype-specific antisense primers or universal primers were used to reverse transcribe the total RNA into cDNA with the PrimeScript™ 1st Strand cDNA Synthesis Kit using the manufacturer's protocol. The antibody fragments of $V_H$, $V_L$, $C_H$, and $C_L$ were amplified. Amplified antibody fragments were then separately cloned into a standard cloning vector using standard molecular cloning procedures. Colony PCR was performed to identify clones with inserts of correct sizes. More than five single colonies with inserts of correct sizes were sequenced for each antibody fragment.

Ultimately, five single colonies with correct $V_H$, $V_L$, $C_H$, $C_L$ insert sizes were sent for sequencing. The $V_H$, $V_L$, $C_H$, $C_L$ genes of five different clones were found to be nearly identical. The PAb1 and PAb2 consensus sequences, listed in the Sequences section below, represent the sequences of the PAb1 and PAb2 antibodies.

In Vitro Assays Using PAb1

Figure 3A:
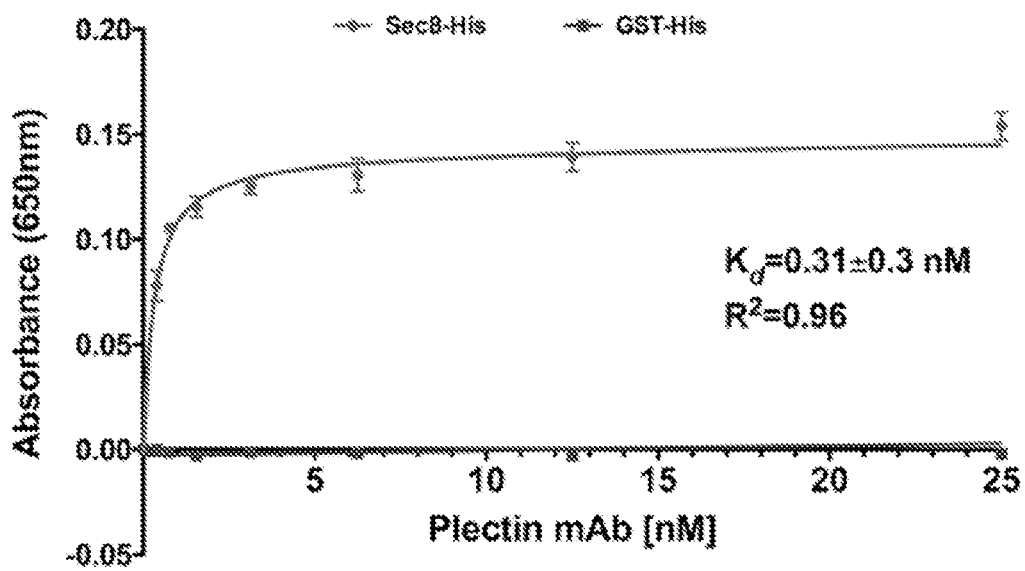
FIGS. 3A-3B show PAb1 binding specificity on recombinant human C-terminal portion of Plectin-1 protein (FIG. 3A, Sec8-His) and plectin-1-positive L3.6pl cancer cells (FIG. 3B).
Figure 3B:
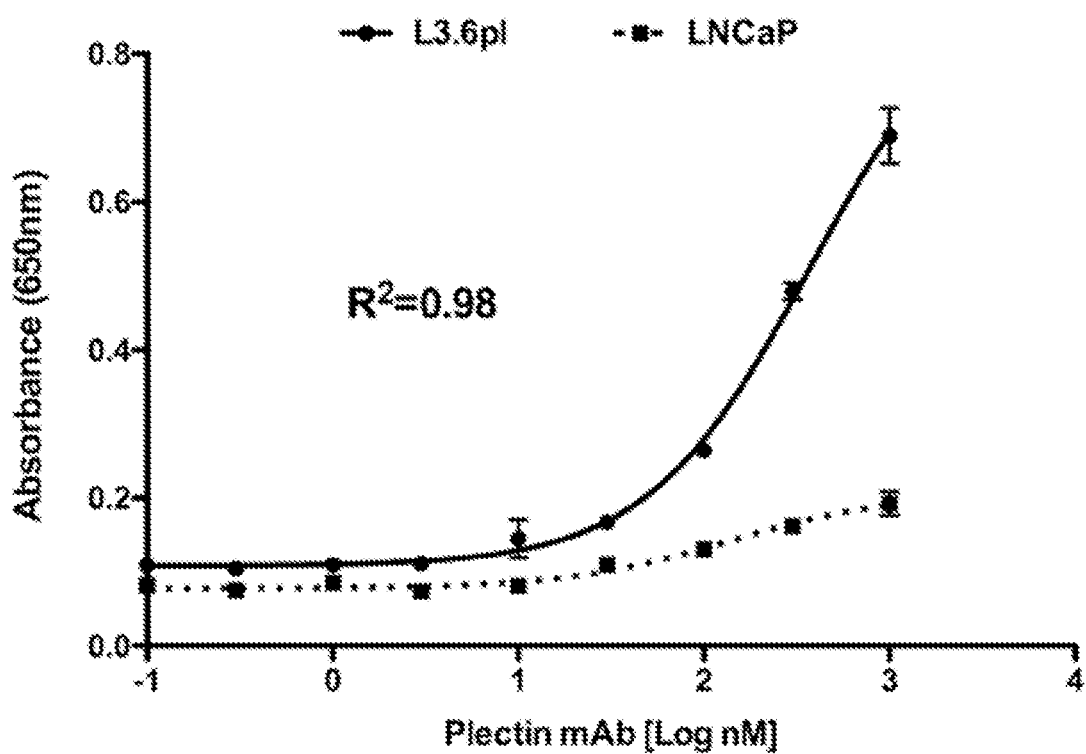

In vitro binding assays were performed. FIG. 3A shows PAb1 binds specifically to a recombinant human C-terminal portion of plectin-1 protein. Data indicate that PAb1 binds selectively to recombinant human Sec8-His protein with high affinity (e.g., a $K_d < 1$ nM). FIG. 3B shows PAb1 binding specificity on plectin-1 positive L3.6pl cancer cells; PAb1 did not bind to plectin-1 negative LNCaP cells.

Figure 4A:
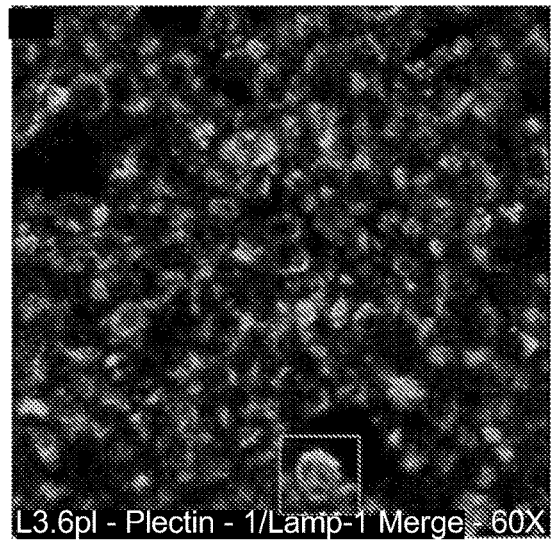
FIGS. 4A-4E show internalization of PAb1 in L3.6pl plectin-1-positive cancer cells.
Figure 4B:
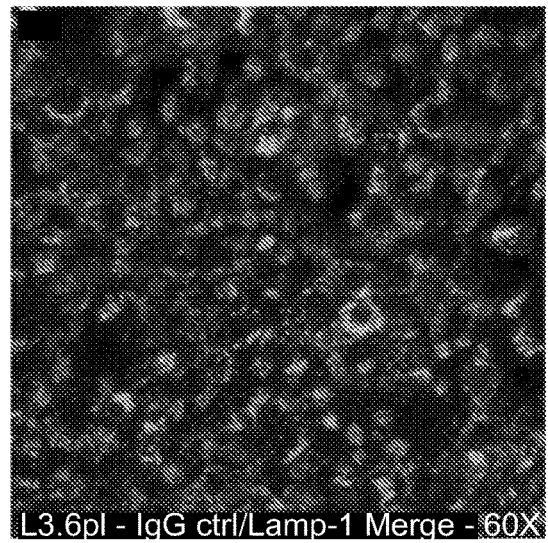
Figures 4C, 4D, 4E:
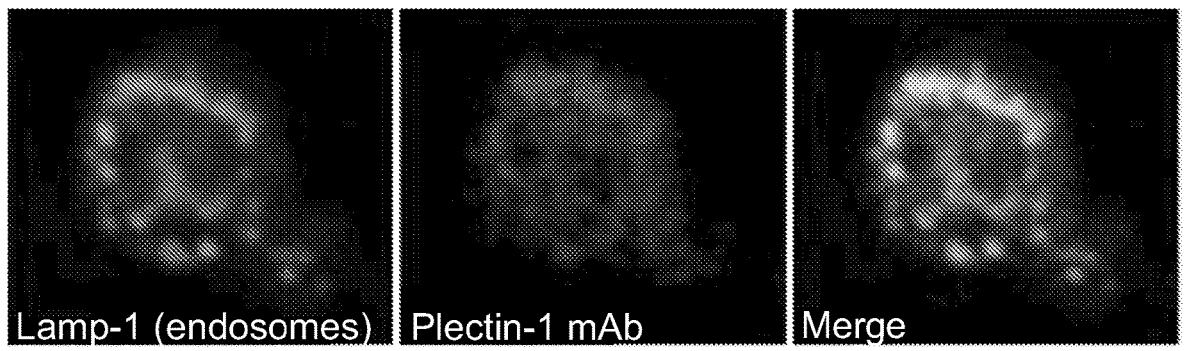

FIGS. 4A-4E show internalization of PAb1 in L3.6pl plectin-1 positive cancer cells. Representative confocal microscopy images demonstrating staining of L3.6pl cells with PAb1 (FIG. 4A) or IgG control (FIG. 4B), merged with endosomal marker LAMP-1, are shown. Co-localization of PAb1 and LAMP-1 was observed (FIGS. 4C-4E). Quantification assays indicated that a significant portion of PAb1 merged with LAMP-1, whereas IgG control did not. Measurement of internalized $^{125}$I-PAb1 radioactivity after incubation at 37° C., 4° C., or in combination with cold PAb1 in L3.6pl cells, indicated a decrease in radioactivity in both cell lines at 4° C. vs. 37 4° C., while internalization activity decreased only in the L3.6pl cells during competition with cold PAb1 (Comp.).

Figure 5A:
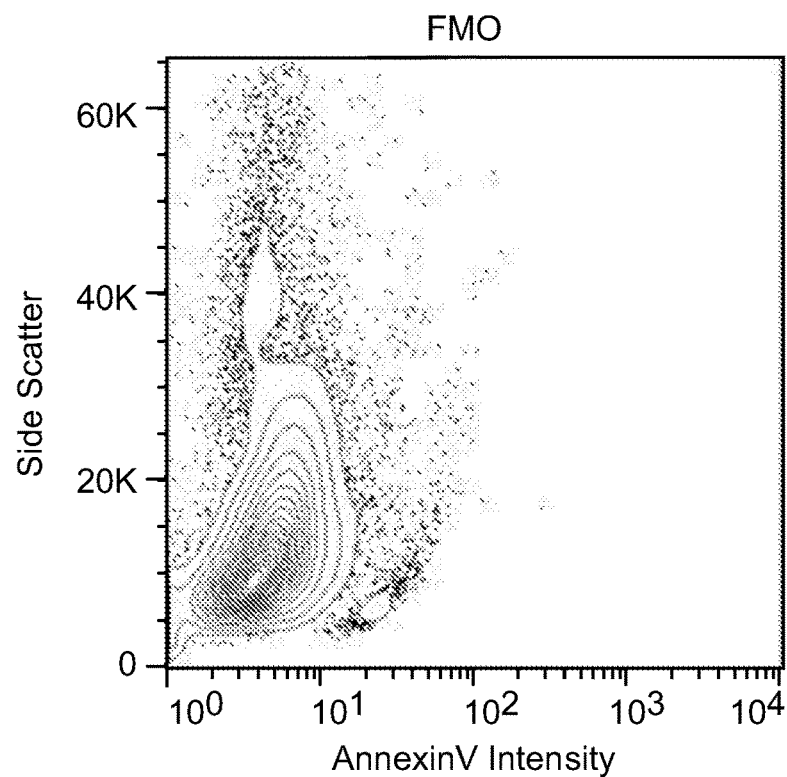
FIGS. 5A-5D show induction of cancer cell death by apoptosis after treatment with PAb1.
Figure 5B:
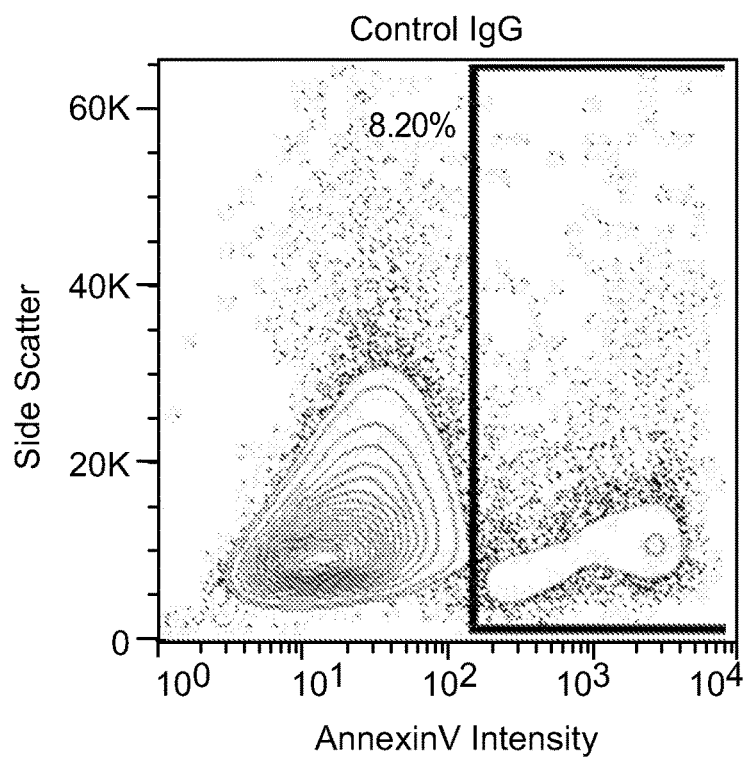
Figure 5C:
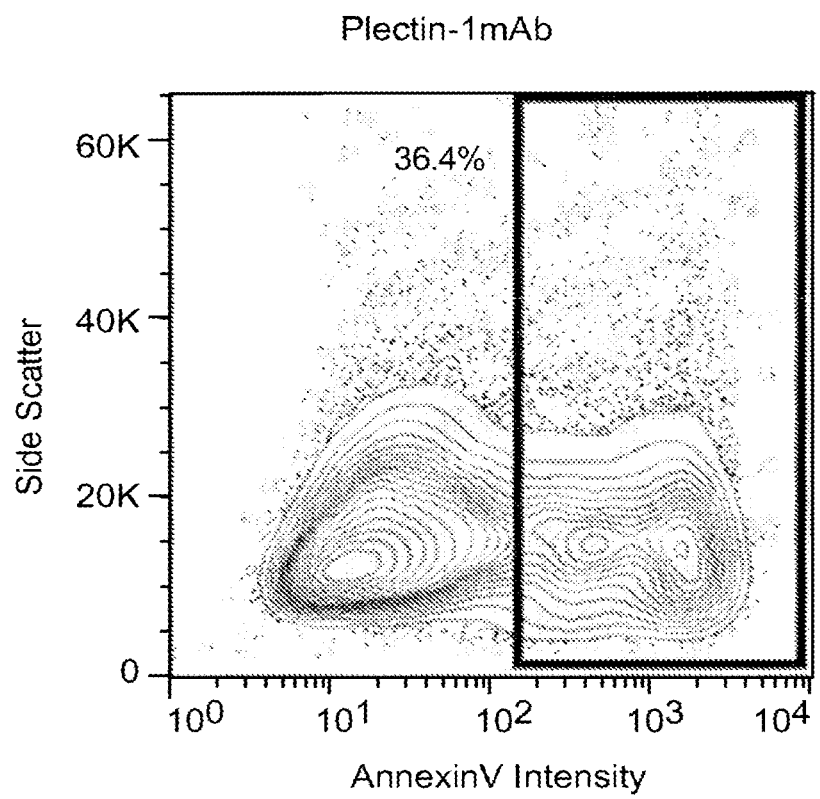
Figure 5D:
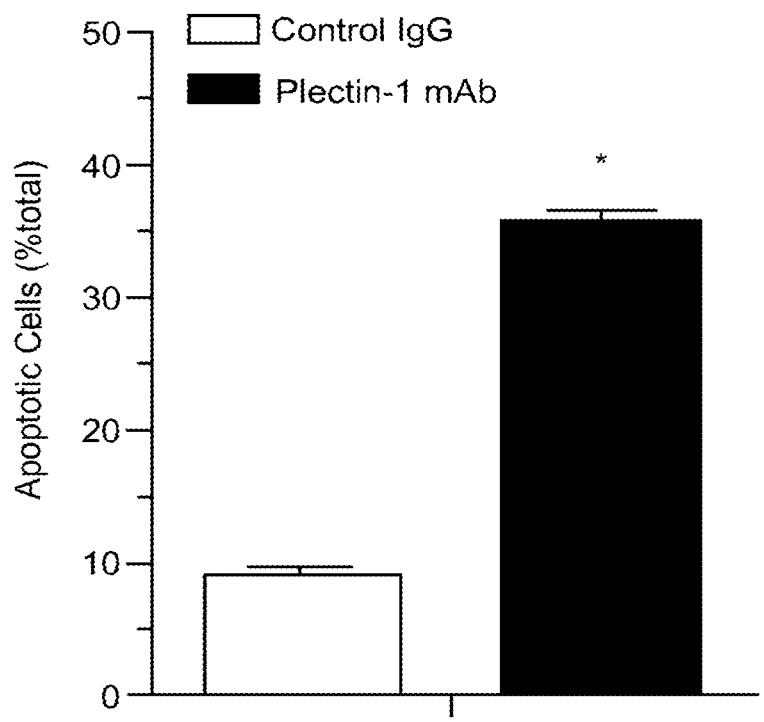

FIGS. 5A-5D show data relating to induction of cancer cell death by apoptosis after treatment with PAb1. FIG. 5A shows a fluorescence minus one control experiment of L3.6pl cells by flow cytometry. FIG. 5B shows L3.6pl Annexin V-positive cells 72 hours after treatment with IgG control. FIG. 5C shows L3.6pl Annexin V-positive cells 72 hours after treatment with PAb1. Data indicate PAb1-treated L3.6pl cells experienced significantly more apoptosis (as assessed by Annexin V) compared to control IgG-treated cells (FIG. 5D).

Survival of cancer cell types and healthy cell types was measured 72 hours after treatment with either PAb1 or IgG control. EC50s were calculated by logistical nonlinear regression and reported as the concentration of mAb (nM) that reduced cell viability by 50%. Data are shown in Table 4 (below).

TABLE 4

| Cell name | Origin | Phenotype | Tissue type | Plectin-1mAb EC50 (nM) | Plectin-1 mAb Cell survival min. (%) | IgG EC50 (nM) | IgG Cell survival min. (%) |
|---|---|---|---|---|---|---|---|
| Keratinocyte | Human | Normal | Skin | 500 | 80 | no fit | 90 |
| HPDE | Human | Normal | Pancreas | 300 | 80 | 330 | 64 |
| RL14 | Human | Normal | Heart | 4020 | 55 | 345 | 82 |
| HEK293T | Human | Normal | Kidney | 324 | 32 | 65 | 95 |
| L3.6pl | Human | Cancer | Pancreas | 34 | 23 | 5049 | 9 |
| YapC | Human | Cancer | Pancreas | 43 | 19 | 225 | 38 |
| OVCAR8 | Human | Cancer | Ovary | 63 | 16 | no fit | 100 |
| SKOV3 | Human | Cancer | Ovary | 53 | 6 | no fit | 83 |

Figure 6A:
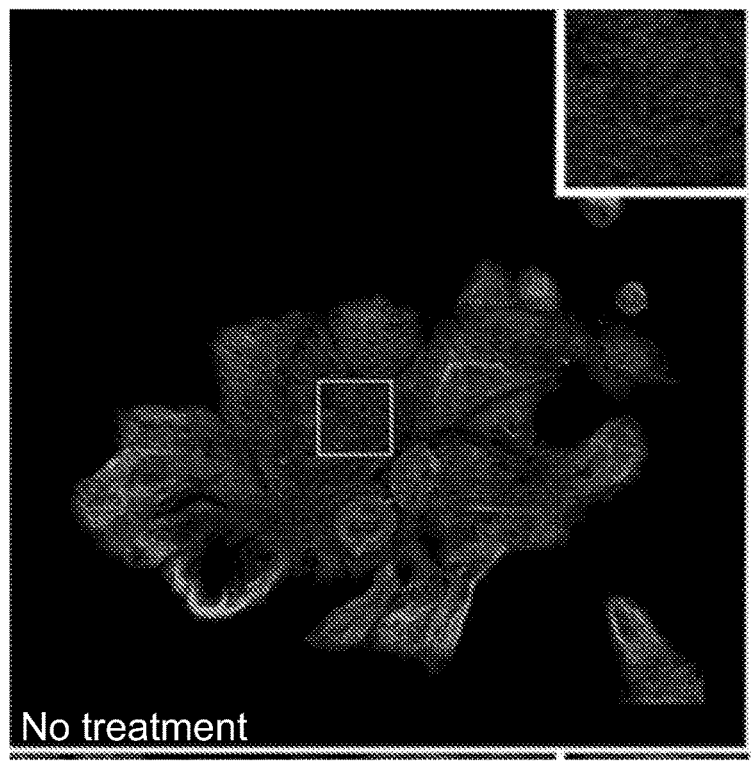
FIGS. 6A-6D show effects of PAb1 treatment on tubulin anisotropy of YapC cancer cells.
Figure 6B:
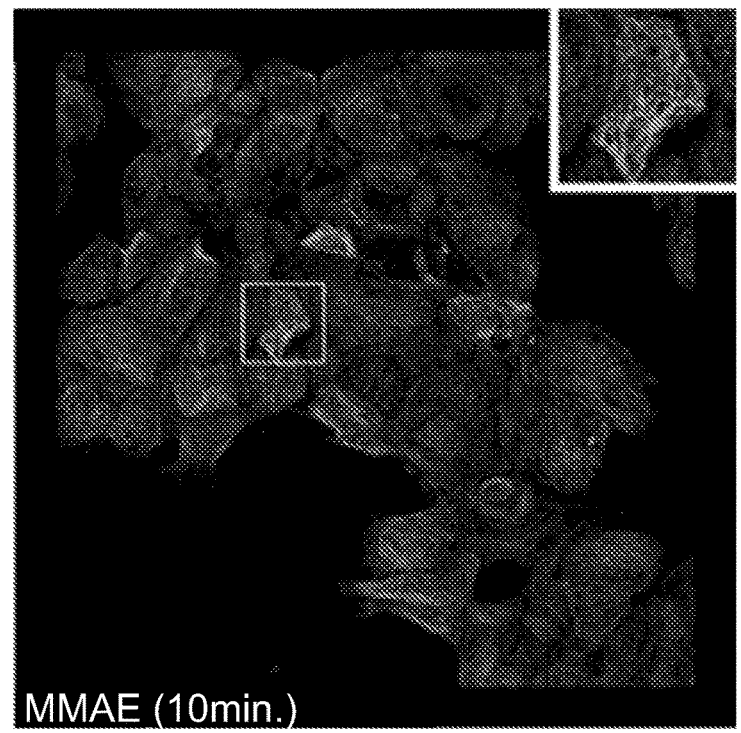
Figure 6C:
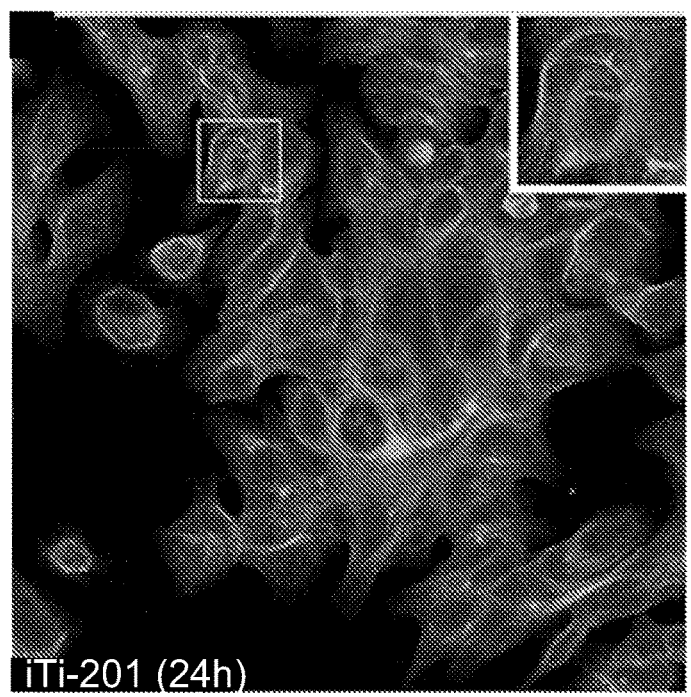
Figure 6D:
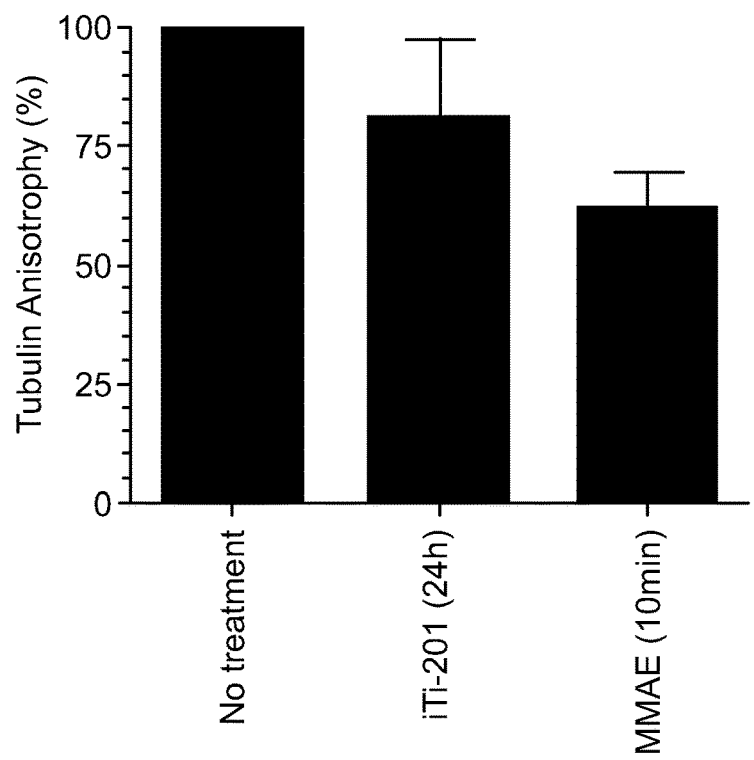

The effect of PAb1 treatment on tubulin anisotropy of YapC cancer cells was examined by confocal microscopy. FIG. 6A shows tubulin staining in YapC cells that were not treated with PAb1. FIG. 6B shows tubulin staining 10 minutes post monomethyl auristatin E (MMAE) treatment; MMAE blocks tubulin polymerization. FIG. 6C shows tubulin staining 24 hours post PAb1 treatment. Data indicate a decrease in anisotropy in cells treated with PAb1 compared to untreated control cells (FIG. 6D).

Figure 7A:
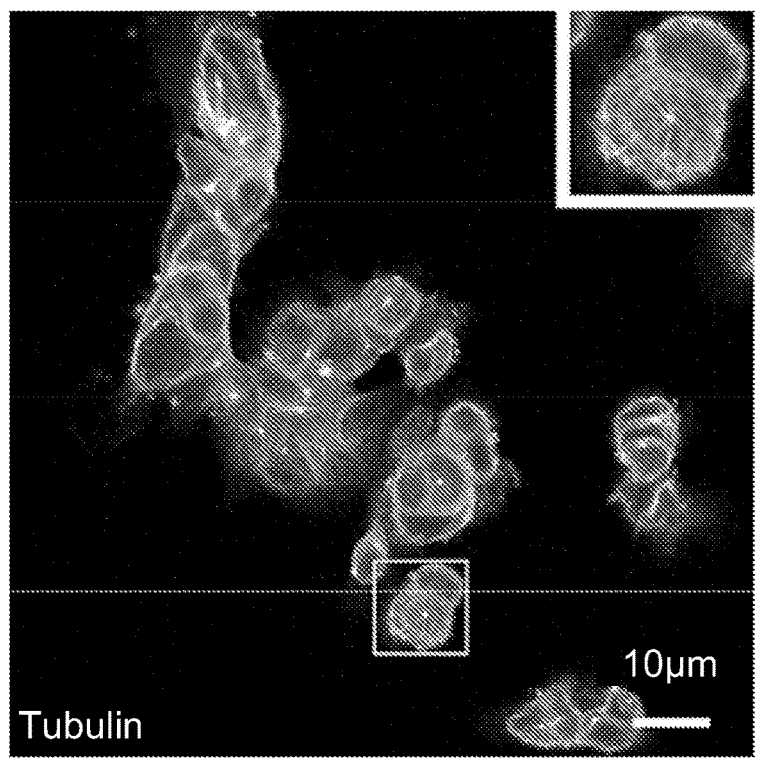
FIGS. 7A-7C show co-localization of PAb1 with tubulin in YapC cancer cells.
Figure 7B:
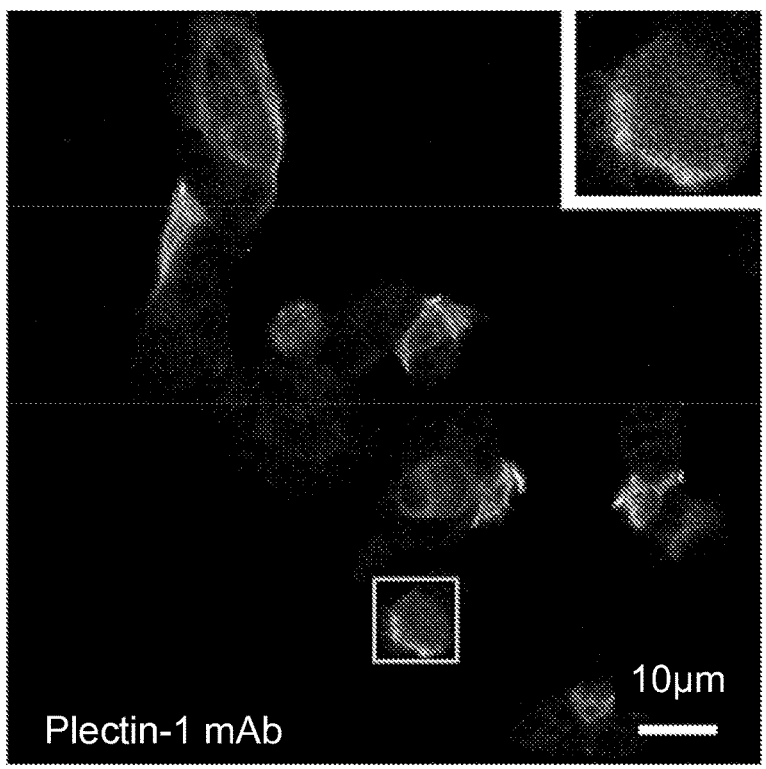
Figure 7C:
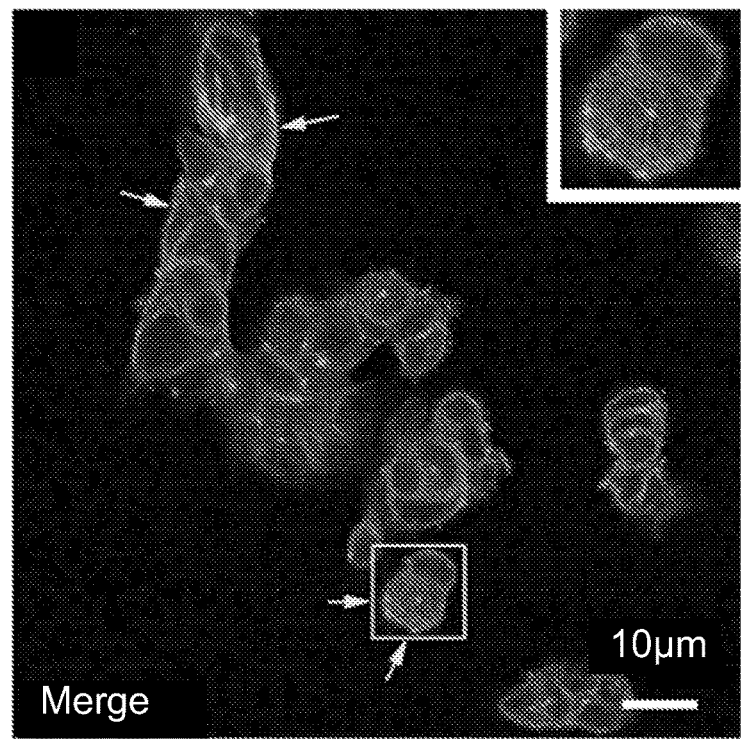

Co-localization of PAb1 with tubulin in YapC cancer cells was also investigated. Representative confocal microscopy images of YapC after tubulin staining (FIG. 7A) and PAb1 staining (FIG. 7B) are shown. Data indicate that tubulin and PAb1 co-localize (FIG. 7C; arrows) on the surface of dying cells. Increased PAb1 staining was also observed on couple cells.

In Vitro Assays Using PAb1

Figure 8A:
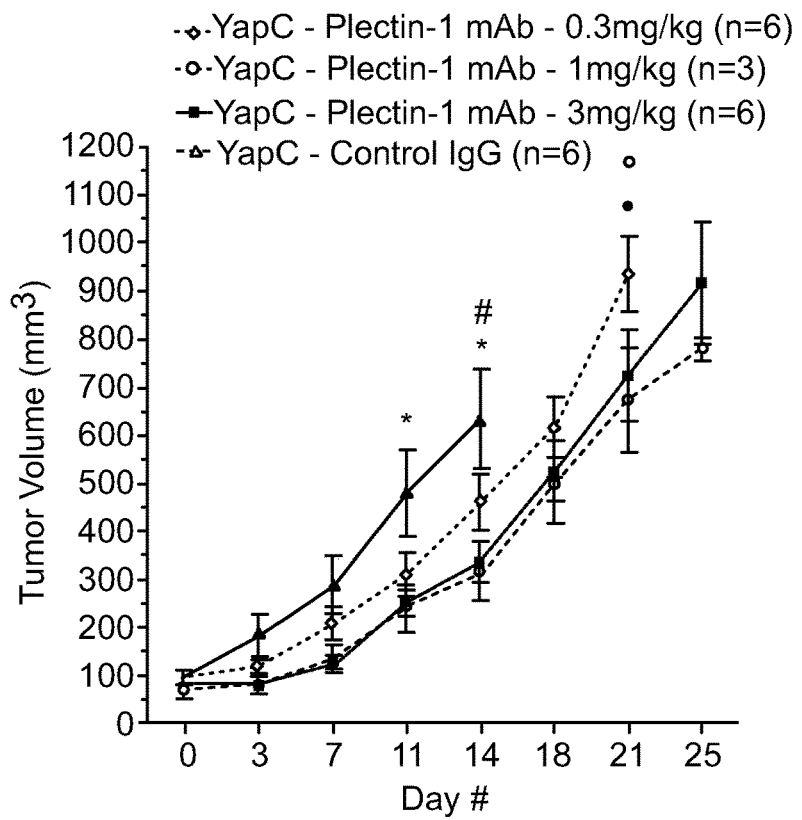
FIGS. 8A-8E show in vivo PAb1 dose-escalating treatment of immunocompromised mice bearing a subcutaneous YapC tumor.
Figure 8B:
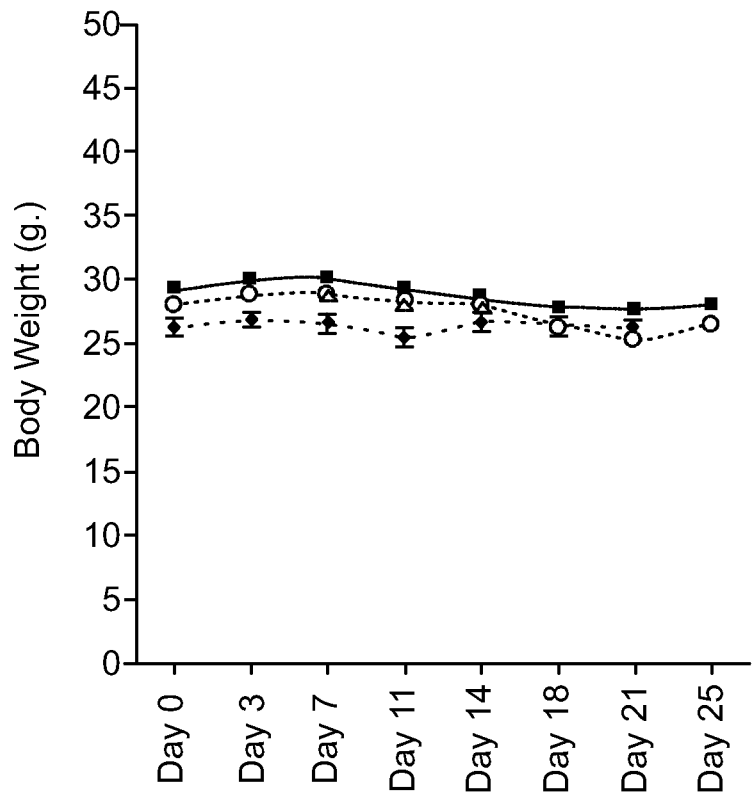
Figures 8C, 8D, 8E:
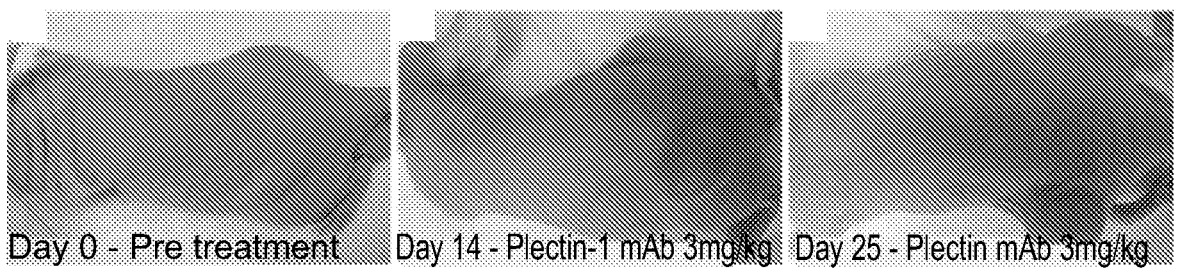

Immunocompromised mice bearing a subcutaneous YapC tumor were administered either PAb1 or IgG control. Data indicated that after 11 days, the mice treated with 3 mg/kg PAb1 had a significantly smaller tumor volume than mice treated with the IgG control (FIG. 8A). Data also indicated that 1 mg/kg PAb1 of mice elicited a significant reduction of tumor volume at day 14. Two higher doses (1 mg/kg and 3 mg/kg) of PAb1 resulted in a significantly lower tumor volume compared to the mice treated with 0.3 mg/kg PAb1 (FIG. 8A), indicating a dose-dependent effect. Data also indicated that animals treated with PAb1 did not lose weight during the entire duration of treatment (FIG. 8B). Photos of mice treated with 3 mg/kg PAb1 at Day 0, Day 14 and Day 25 are also shown (FIGS. 8C-8E).

SEQUENCES

```
-Plectin (hemidesmosomal protein 1), Homo sapiens;
target protein underlined
                                                         >SEQ ID NO: 1
MVAGMLMPRDQLRAIYEVLFREGVMVAKKDRRPRSLHPHVPGVTNLQVMRAMASLRARG

LVRETFAWCHFYWYLTNEGIAHLRQYLHLPPEIVPASLQRVRRPVAMVMPARRTPHVQAVQ

GPLGSPPKRGPLPTEEQRVYRRKELEEVSPETPVVPATTQRTLARPGPEPAPATDERDRVQKK

TFTKWVNKHLIKAQRHISDLYEDLRDGHNLISLLEVLSGDSLPREKGRMRFHKLQNVQIALD

YLRHRQVKLVNIRNDDIADGNPKLTLGLIWTIILHFQISDIQVSGQSEDMTAKEKLLLWSQRM

VEGYQGLRCDNFTSSWRDGRLFNAIIHRHKPLLIDMNKVYRQTNLENLDQAFSVAERDLGVT

RLLDPEDVDVPQPDEKSIITYVSSLYDAMPRVPDVQDGVRANELQLRWQEYRELVLLLLQW

MRHHTAAFEERRFPSSFEEIEILWSQFLKFKEMELPAKEADKNRSKGIYQSLEGAVQAGQLKV

PPGYHPLDVEKEWGKLHVAILEREKQLRSEFERLECLQRIVTKLQMEAGLCEEQLNQADALL

QSDVRLLAAGKVPQRAGEVERDLDKADSMIRLLFNDVQTLKDGRHPQGEQMYRRVYRLHE

RLVAIRTEYNLRLKAGVAAPATQVAQVTLQSVQRRPELEDSTLRYLQDLLAWVEENQHRVD

GAEWGVDLPSVEAQLGSHRGLHQSIEEFRAKIERARSDEGQLSPATRGAYRDCLGRLDLQYA

KLLNSSKARLRSLESLHSFVAAATKELMWLNEKEEEEVGFDWSDRNTNMTAKKESYSALMR

ELELKEKKIKELQNAGDRLLREDHPARPTVESFQAALQTQWSWMLQLCCCIEAHLKENAAY

FQFFSDVREAEGQLQKLQEALRRKYSCDRSATVTRLEDLLQDAQDEKEQLNEYKGHLSGLA

KRAKAVVQLKPRHPAHPMRGRLPLLAVCDYKQVEVTVHKGDECQLVGPAQPSHWKVLSSS

GSEAAVPSVCFLVPPPNQEAQEAVTRLEAQHQALVTLWHQLHVDMKSLLAWQSLRRDVQLI

RSWSLATFRTLKPEEQRQALHSLELHYQAFLRDSQDAGGFGPEDRLMAEREYGSCSHHYQQ

LLQSLEQGAQEESRCQRCISELKDIRLQLEACETRTVHRLRLPLDKEPARECAQRIAEQQKAQ

AEVEGLGKGVARLSAEAEKVLALPEPSPAAPTLRSELELTLGKLEQVRSLSAIYLEKLKTISLV
```

```
IRGTQGAEEVLRAHEEQLKEAQAVPATLPELEATKASLKKLRAQAEAQQPTFDALRDELRGA

QEVGERLQQRHGERDVEVERWRERVAQLLERWQAVLAQTDVRQRELEQLGRQLRYYRESA

DPLGAWLQDARRRQEQIQAMPLADSQAVREQLRQEQALLEEIERHGEKVEECQRFAKQYIN

AIKDYELQLVTYKAQLEPVASPAKKPKVQSGSESVIQEYVDLRTHYSELTTLTSQYIKFISETL

RRMEEEERLAEQQRAEERERLAEVEAALEKQRQLAEAHAQAKAQAEREAKELQQRMQEEV

VRREEAAVDAQQQKRSIQEELQQLRQSSEAEIQAKARQAEAAERSRLRIEEEIRVVRLQLEAT

ERQRGGAEGELQALRARAEEAEAQKRQAQEEAERLRRQVQDESQRKRQAEVELASRVKAE

AEAAREKQRALQALEELRLQAEEAERRLRQAEVERARQVQVALETAQRSAEAELQSKRASF

AEKTAQLERSLQEEHVAVAQLREEAERRAQQQAEAERAREEAERELERWQLKANEALRLRL

QAEEVAQQKSLAQAEAEKQKEEAEREARRRGKAEEQAVRQRELAEQELEKQRQLAEGTAQ

QRLAAEQELIRLRAETEQGEQQRQLLEEELARLQREAAAATQKRQELEAELAKVRAEMEVL

LASKARAEEESRSTSEKSKQRLEAEAGRFRELAEEAARLRALAEEEAKRQRQLAEEDAARQRA

EAERVLAEKLAAIGEATRLKTEAEIALKEKEAENERLRRLAEDEAFQRRRLEEQAAQHKADI

EERLAQLRKASDSELERQKGLVEDTLRQRRQVEEEILALKASFEKAAAGKAELELELGRIRSN

AEDTLRSKEQAELEAARQRQLAAEEEERRRREAEERVQKSLAAEEEAARQRKAALEEVERLK

AKVEEARRLRERAEQESARQLQLAQEEAAQKRLQAEEKAHAFAVQQKEQELQQTLQQEQSV

LDQLRGEAEAARRAAEEAEEARVQAEREAAQSRRQVEEAERLKQSAEEQAQARAQAQAAA

EKLRKEAEQEAARRAQAEQAALRQKQAADAEMEKHKKFAEQTLRQKAQVEQELTTLRLQL

EETDHQKNLLDEELQRLKAEATEAARQRSQVEEELFSVRVQMEELSKLKARIEAENRALILR

DKDNTQRFLQEEAEKMKQVAEEAARLSVAAQEAARLRQLAEEDLAQQRALAEKMLKEKM

QAVQEATRLKAEAELLQQQKELAQEQARRLQEDKEQMAQQLAEETQGFQRTLEAERQRQL

EMSAEAERLKLRVAEMSRAQARAEEDAQRFRKQAEEIGEKLHRTELATQEKVTLVQTLEIQR

QQSDHDAERLREAIAELEREKEKLQQEAKLLQLKSEEMQTVQQEQLLQETQALQQSFLSEKD

SLLQRERFIEQEKAKLEQLFQDEVAKAQQLREEQQRQQQQMEQERQRLVASMEEARRQHE

AEEGVRRKQEELQQLEQQRRQQEELLAEENQRLREQLQLLEEQHRAALAHSEEVTASQVAA

TKTLPNGRDALDGPAAEAEPEHSFDGLRRKVSAQRLQEAGILSAEELQRLAQGHTTVDELAR

REDVRHYLQGRSSIAGLLLKATNEKLSVYAALQRQLLSPGTALILLEAQAASGFLLDPVRNRR

LTVNEAVKEGVVGPELHHKLLSAERAVTGYKDPYTGQQISLFQAMQKGLIVREHGIRLLEAQ

IATGGVIDPVHSHRVPVDVAYRRGYFDEEMNRVLADPSDDTKGFFDPNTHENLTYLQLLERC

VEDPETGLCLLPLTDKAAKGGELVYTDSEARDVFEKATVSAPFGKFQGKTVTIWEIINSEYFT

AEQRRDLLRQFRTGRITVEKIIKIIITVVEEQEQKGRLCFEGLRSLVPAAELLESRVIDRELYQQ

LQRGERSVRDVAEVDTVRRALRGANVIAGVWLEEAGQKLSIYNALKKDLLPSDMAVALLEA

QAGTGHIIDPATSARLTVDEAVRAGLVGPEFHEKLLSAEKAVTGYRDPYTGQSVSLFQALKK

GLIPREQGLRLLDAQLSTGGIVDPSKSHRVPLDVACARGCLDEETSRALSAPRADAKAYSDPS

TGEPATYGELQQRCRPDQLTGLSLLPLSEKAARARQEELYSELQARETFEKTPVEVPVGGFK

GRTVTVWELISSEYFTAEQRQELLRQFRTGKVTVEKVIKILITIVEEVETLRQERLSFSGLRAPV

PASELLASGVLSRAQFEQLKDGKTTVKDLSELGSVRTLLQGSGCLAGIYLEDTKEKVSIYEAM

RRGLLRATTAALLLEAQAATGFLVDPVRNQRLYVHEAVKAGVVGPELHEQLLSAEKAVTGY

RDPYSGSTISLFQAMQKGLVLRQHGIRLLEAQIATGGIIDPVHSHRVPVDVAYQRGYFSEEMN

RVLADPSDDTKGFFDPNTHENLTYRQLLERCVEDPETGLRLLPLKGAEKAEVVETTQVYTEE
```

-continued

ETRRAFEETQIDIPGGGSHGGSTMSLWEVMQSDLIPEEQRAQLMADFQAGRVTKERMIIIIIEII

EKTEIIRQQGLASYDYVRRRLTAEDLFEARIISLETYNLLREGTRSLREALEAESAWCYLYGTG

SVAGVYLPGSRQTLSIYQALKKGLLSAEVARLLLEAQAATGFLLDPVKGERLTVDEAVRKGL

VGPELHDRLLSAERAVTGYRDPYTEQTISLFQAMKKELIPTEEALRLLDAQLATGGIVDPRLG

FHLPLEVAYQRGYLNKDTHDQLSEPSEVRSYVDPSTDERLSYTQLLRRCRRDDGTGQLLLPL

SDARKLTFRGLRKQITMEELVRSQVMDEATALQLREGLTSIEEVTKNLQKFLEGTSCIAGVFV

DATKERLSVYQAMKKGIIRPGTAFELLEAQAATGYVIDPIKGLKLTVEEAVRMGIVGPEFKD

KLLSAERAVTGYKDPYSGKLISLFQAMKKGLILKDHGIRLLEAQIATGGIIDPEESHRLPVEVA

YKRGLFDEEMNEILTDPSDDTKGFFDPNTEENLTYLQLMERCITDPQTGLCLLPLKEKKRERK

TSSKSSVRKRRVVIVDPETGKEMSVYEAYRKGLIDHQTYLELSEQECEWEEITI<u>SSSDGVVKS</u>

<u>MIIDRRSGRQYDIDDAIAKNLIDRSALDQYRAGTLSITEFADMLSGNAGGFRSRSSSVGSSSSY</u>

<u>PISPAVSRTQLASWSDPTEETGPVAGILDTETLEKVSITEAMHRNLVDNITGQRLLEAQACTG</u>

<u>GIIDPSTGERFPVTDAVNKGLVDKIMVDRINLAQKAFCGFEDPRTKTKMSAAQALKKGWLY</u>

<u>YEAGQRFLEVQYLTGGLIEPDTPGRVPLDEALQRGTVDARTAQKLRDVGAYSKYLTCPKTK</u>

<u>LKISYKDALDRSMVEEGTGLRLLEAAAQSTKGYYSPYSVSGSGSTAGSRTGSRTGSRAGSRR</u>

<u>GSFDATGSGFSMTFSSSSYSSSGYGRRYASGSSASLGGPESAVA</u>

-pET-10NC-Plec C term: His tag-EK cleavage site-Human
plectin 1 (section 8)-stop codon (344 amino acids;
MW = 36959.2; predicted pI = 8.80)
>SEQ ID NO: 2

MRS*HHHHHHHHHH*RSGTGDDDDKAMADIGSEFELRRQACGFRSRSSSVGSSSSYPIS

PAVSRTQLASWSDPTEETGPVAGILDTETLEKVSITEAMHRNLVDNITGQRLLEAQAC

TGGIIDPSTGERFPVTDAVNKGLVDKIMVDRINLAQKAFCGFEDPRTKTKMSAAQAL

KKGWLYYEAGQRFLEVQYLTGGLIEPDTPGRVPLDEALQRGTVDARTAQKLRDVG

AYSKYLTCPKTKLKISYKDALDRSMVEEGTGLRLLEAAAQSTKGYYSPYSVSGSGST

AGSRTGSRTGSRAGSRRGSFDATGSGFSMTFSSSSYSSSGYGRRYASGSSSLGGPESA

VA.

-pGEX2t-Section 8: GST tag-Thrombin cleavage site-Human
plectin 1 (section 8)-stop codon (540 amino acids;
MW = 59809.3; predicted pI = 8.15)
>SEQ ID NO: 3

*MSPILGYWKIKGLVQPTRLLLEYLEEKYEEHLYERDEGDKWRNKKFELGLEFPNLPYYIDGDVKLT*

*QSMAIIRYIADKHNMLGGCPKERAEISMLEGAVLDIRYGVSRIAYSKDFETLKVDFLSKLPEMLKMF*

*EDRLCHKTYLNGDHVTHPDFMLYDALDVVLYMDPMCLDAFPKLVCFKKRIEAIPQIDKYLKSSKYI*

*AWPLQGWQATFGGGDHPPK*SDLVPRGSEFELRRQACGFRSRSSSVGSSSSYPISPAVSRTQLA

SWSDPTEETGPVAGILDTETLEKVSITEAMHRNLVDNITGQRLLEAQACTGGIIDPSTGERFPV

TDAVNKGLVDKIMVDRINLAQKAFCGFEDPRTKTKMSAAQALKKGWLYYEAGQRFLEVQY

LTGGLIEPDTPGRVPLDEALQRGTVDARTAQKLRDVGAYSKYLTCPKTKLKISYKDALDRSM

VEEGTGLRLLEAAAQSTKGYYSPYSVSGSGSTAGSRTGSRTGSRAGSRRGSFDATGSGFSMT

FSSSSYSSSGYGRRYASGSSSLGGPESAVA.

Pab2 Sequences

| Name | Sequence | SEQ ID NO: |
|---|---|---|
| Pab2 Heavy Chain | ATGAACTTCGGGCTCAGCTTGATTTTCCTTGCCCTCATTTTA AAAGGTGTCCAGTGTGAGGTGCAGCTGGTGGAGTCTGGGG AGACTTGGTGAAGCCTGGAGGGTCCCTGAAACTCTCCTGT GCAGCCTCTGGATTCACTTTCAGTAGGTATGGCATGTCTTG GGTTCGCCAGACTCCAGACAAGAGGCTGGAGTGGGTCGCA ACCATTAGTATTGGTGGTACTTACACCTACTATCCAGACAG TATGAAGGGGCGATTCACCATCTCCAGAGACAATGCCAAG AACACCCTGTACCTGCAAATGAGCAGTCTGAAGTCTGAGG ACACAGCCATGTATTACTGTGCAAGACGGGGGTATGGTAA CTACTCTTACTATGGTATGGACTACTGGGGTCAAGGAACCT CAGTCACCGTCTCCTCAGCCAAAACGACACCCCCATCTGTC TATCCACTGGCCCCTGGATCTGCTGCCCAAACTAACTCCAT GGTGACCCTGGGATGCCTGGTCAAGGGCTATTTCCCTGAGC CAGTGACAGTGACCTGGAACTCTGGATCCCTGTCCAGCGGT GTGCACACCTTCCCAGCTGTCCTGCAGTCTGACCTCTACAC TCTGAGCAGCTCAGTGACTGTCCCCTCCAGCACCTGGCCCA GCGAGACCGTCACCTGCAACGTTGCCCACCCGGCCAGCAG CACCAAGGTGGACAAGAAAATTGTGCCCAGGGATTGTGGT TGTAAGCCTTGCATATGTACAGTCCCAGAAGTATCATCTGT CTTCATCTTCCCCCCAAAGCCCAAGGATGTGCTCACCATTA CTCTGACTCCTAAGGTCACGTGTGTTGTGGTAGACATCAGC AAGGATGATCCCGAGGTCCAGTTCAGCTGGTTTGTAGATGA TGTGGAGGTGCACACAGCTCAGACGCAACCCCGGGAGGAG CAGTTCAACAGCACTTTCCGCTCAGTCAGTGAACTTCCCAT CATGCACCAGGACTGGCTCAATGGCAAGGAGTTCAAATGC AGGGTCAACAGTGCAGCTTTCCCTGCCCCCATCGAGAAAA CCATCTCCAAAACCAAAGGCAGACCGAAGGCTCCACAGGT GTACACCATTCCACCTCCCAAGGAGCAGATGGCCAAGGAT AAAGTCAGTCTGACCTGCATGATAACAGACTTCTTCCCTGA AGACATTACTGTGGAGTGGCAGTGGAATGGGCAGCCAGCG GAGAACTACAAGAACACTCAGCCCATCATGGACACAGATG GCTCTTACTTCGTCTACAGCAAGCTCAATGTGCAGAAGAGC AACTGGGAGGCAGGAAATACTTTCACCTGCTCTGTGTTACA TGAGGGCCTGCACAACCACCATACTGAGAAGAGCCTCTCC CACTCTCCTGGTAAATGA | 4 |
| Pab2 Heavy Chain Leader | ATGAACTTCGGGCTCAGCTTGATTTTCCTTGCCCTCATTTTA AAAGGTGTCCAGTGT | 5 |
| Pab2 Heavy Chain FR1 | GAGGTGCAGCTGGTGGAGTCTGGGGAGACTTGGTGAAGC CTGGAGGGTCCCTGAAACTCTCCTGTGCAGCCTCTGGATTC ACTTTCAGT | 6 |
| Pab2 Heavy Chain CDR1 | AGGTATGGCATGTCT | 7 |
| Pab2 Heavy Chain FR2 | TGGGTTCGCCAGACTCCAGACAAGAGGCTGGAGTGGGTCG CA | 8 |
| Pab2 Heavy Chain CDR2 | ACCATTAGTATTGGTGGTACTTACACCTACTATCCAGACAG TATGAAGGGG | 9 |
| Pab2 Heavy Chain FR3 | CGATTCACCATCTCCAGAGACAATGCCAAGAACACCCTGT ACCTGCAAATGAGCAGTCTGAAGTCTGAGGACACAGCCAT GTATTACTGTGCAAGA | 10 |
| Pab2 Heavy Chain CDR3 | CGGGGGTATGGTAACTACTCTTACTATGGTATGGACTAC | 11 |
| Pab2 Heavy Chain FR4 | TGGGGTCAAGGAACCTCAGTCACCGTCTCCTCA | 12 |
| Pab2 Heavy Chain Variable Region | GAGGTGCAGCTGGTGGAGTCTGGGGAGACTTGGTGAAGC CTGGAGGGTCCCTGAAACTCTCCTGTGCAGCCTCTGGATTC ACTTTCAGTAGGTATGGCATGTCTTGGGTTCGCCAGACTCC AGACAAGAGGCTGGAGTGGGTCGCAACCATTAGTATTGGT GGTACTTACACCTACTATCCAGACAGTATGAAGGGGCGATT CACCATCTCCAGAGACAATGCCAAGAACACCCTGTACCTG CAAATGAGCAGTCTGAAGTCTGAGGACACAGCCATGTATT ACTGTGCAAGACGGGGGTATGGTAACTACTCTTACTATGGT ATGGACTACTGGGGTCAAGGAACCTCAGTCACCGTCTCCTC A | 13 |

| Name | Sequence | SEQ ID NO: |
|---|---|---|
| Pab2 Heavy Chain Constant Region | GCCAAAACGACACCCCCATCTGTCTATCCACTGGCCCCTGG ATCTGCTGCCCAAACTAACTCCATGGTGACCCTGGGATGCC TGGTCAAGGGCTATTTCCCTGAGCCAGTGACAGTGACCTGG AACTCTGGATCCCTGTCCAGCGGTGTGCACACCTTCCCAGC TGTCCTGCAGTCTGACCTCTACACTCTGAGCAGCTCAGTGA CTGTCCCCTCCAGCACCTGGCCCAGCGAGACCGTCACCTGC AACGTTGCCCACCCGGCCAGCAGCACCAAGGTGGACAAGA AAATTGTGCCCAGGGATTGTGGTTGTAAGCCTTGCATATGT ACAGTCCCAGAAGTATCATCTGTCTTCATCTTCCCCCCAAA GCCCAAGGATGTGCTCACCATTACTCTGACTCCTAAGGTCA CGTGTGTTGTGGTAGACATCAGCAAGGATGATCCCGAGGT CCAGTTCAGCTGGTTTGTAGATGATGTGGAGGTGCACACAG CTCAGACGCAACCCCGGGAGGAGCAGTTCAACAGCACTTT CCGCTCAGTCAGTGAACTTCCCATCATGCACCAGGACTGGC TCAATGGCAAGGAGTTCAAATGCAGGGTCAACAGTGCAGC TTTCCCTGCCCCCATCGAGAAAACCATCTCCAAAACCAAAG GCAGACCGAAGGCTCCACAGGTGTACACCATTCCACCTCCC AAGGAGCAGATGGCCAAGGATAAAGTCAGTCTGACCTGCA TGATAACAGACTTCTTCCCTGAAGACATTACTGTGGAGTGG CAGTGGAATGGGCAGCCAGCGGAGAACTACAAGAACACTC AGCCCATCATGGACACAGATGGCTCTTACTTCGTCTACAGC AAGCTCAATGTGCAGAAGAGCAACTGGGAGGCAGGAAATA CTTTCACCTGCTCTGTGTTACATGAGGGCCTGCACAACCAC CATACTGAGAAGAGCCTCTCCCACTCTCCTGGTAAA | 14 |
| Pab2 Heavy Chain | MNFGLSLIFLALILKGVQCEVQLVESGGDLVKPGGSLKLSCAA SGFTFSRYGMSWVRQTPDKRLEWVATISIGGTYTYYPDSMKG RFTISRDNAKNTLYLQMSSLKSEDTAMYYCARRGYGNYSYY GMDYWGQGTSVTVSSAKTTPPSVYPLAPGSAAQTNSMVTLG CLVKGYFPEPVTVTWNSGSLSSGVHTFPAVLQSD | 15 |
| Pab2 Heavy Chain Leader | MNFGLSLIFLALILKGVQC | 16 |
| Pab2 Heavy Chain FR1 | EVQLVESGGDLVKPGGSLKLSCAASGFTFS | 17 |
| Pab2 Heavy Chain CDR1 | RYGMS | 18 |
| Pab2 Heavy Chain FR2 | WVRQTPDKRLEWVA | 19 |
| Pab2 Heavy Chain CDR2 | TISIGGTYTYYPDSMKG | 20 |
| Pab2 Heavy Chain FR3 | RFTISRDNAKNTLYLQMSSLKSEDTAMYYCAR | 21 |
| Pab2 Heavy Chain CDR3 | RGYGNYSYYGMDY | 22 |
| Pab2 Heavy Chain FR4 | WGQGTSVTVSS | 23 |
| Pab2 Heavy Chain Variable Region | EVQLVESGGDLVKPGGSLKLSCAASGFTFSRYGMSWVRQTPD KRLEWVATISIGGTYTYYPDSMKGRFTISRDNAKNTLYLQMS SLKSEDTAMYYCARRGYGNYSYYGMDYWGQGTSVTVSS | 24 |
| Pab2 Heavy Chain Constant Region | AKTTPPSVYPLAPGSAAQTNSMVTLGCLVKGYFPEPVTVTWN SGSLSSGVHTFPAVLQSDLYTLSSSVTVPSSTWPSETVTCNVA HPASSTKVDKKIVPRDCGCKPCICTVPEVSSVFIFPPKPKDVLTI TLTPKVTCVVVDISKDDPEVQFSWFVDDVEVHTAQTQPREEQ FNSTFRSVSELPIMHQDWLNGKEFKCRVNSAAPPAPIEKTISKT KGRPKAPQVYTIPPPKEQMAKDKVSLTCMITDFFPEDITVEWQ WNGQPAENYKNTQPIMDTDGSYFVYSKLNVQKSNWEAGNTF TCSVLHEGLHNHHTEKSLSHSPGK | 25 |
| Pab2 Light Chain | ATGAGGTTCTCTGCTCAGCTTCTGGGGCTGCTTGTGCTCTG GATCCCTGGATCCACTGCAGATATTGTGATGACGCAGGCTG CATTCTCCAATCCAGTCACTCTTGGAACATCAGCTTCCATC TCCTGCAGGTCTAGTAAGAGTCTCCTACATAGTAATGGCAT CACTTATTTGTATTGGTATCTGCAGAAGCCAGGCCAGTCTC CTCAGCTCCTGATTTATCAGATGTCCAACCTTGCCTCAGGA GTCCCAGACAGGTTCAGTAGCAGTGGGTCAGGAACTGATT | 26 |

| Name | Sequence | SEQ ID NO: |
|---|---|---|
| | TCACACTGAGAATCAGCAGAGTGGAGGCTGAGGATGTGGG<br>TGTTTATTACTGTGCTCAAAATCTAGAACTTCCGCTCACGTT<br>CGGTGCTGGGACCAAGCTGGAGCTGAAACGGGCTGATGCT<br>GCACCAACTGTATCCATCTTCCCACCATCCAGTGAGCAGTT<br>AACATCTGGAGGTGCCTCAGTCGTGTGCTTCTTGAACAACT<br>TCTACCCCAAAGACATCAATGTCAAGTGGAAGATTGATGG<br>CAGTGAACGACAAAATGGCGTCCTGAACAGTTGGACTGAT<br>CAGGACAGCAAAGACAGCACCTACAGCATGAGCAGCACCC<br>TCACGTTGACCAAGGACGAGTATGAACGACATAACAGCTA<br>TACCTGTGAGGCCACTCACAAGACATCAACTTCACCCATTG<br>TCAAGAGCTTCAACAGGAATGAGTGTTAG | |
| Pab2 Light Chain Leader | ATGAGGTTCTCTGCTCAGCTTCTGGGGCTGCTTGTGCTCTG<br>GATCCCTGGATCCACTGCA | 27 |
| Pab2 Light Chain FR1 | GATATTGTGATGACGCAGGCTGCATTCTCCAATCCAGTCAC<br>TCTTGGAACATCAGCTTCCATCTCCTGC | 28 |
| Pab2 Light Chain CDR1 | AGGTCTAGTAAGAGTCTCCTACATAGTAATGGCATCACTTA<br>TTTGTAT | 29 |
| Pab2 Light Chain FR2 | TGGTATCTGCAGAAGCCAGGCCAGTCTCCTCAGCTCCTGAT<br>TTAT | 30 |
| Pab2 Light Chain CDR2 | CAGATGTCCAACCTTGCCTCA | 31 |
| Pab2 Light Chain FR3 | GGAGTCCCAGACAGGTTCAGTAGCAGTGGGTCAGGAACTG<br>ATTTCACACTGAGAATCAGCAGAGTGGAGGCTGAGGATGT<br>GGGTGTTTATTACTGT | 32 |
| Pab2 Light Chain CDR3 | GCTCAAAATCTAGAACTTCCGCTCACG | 33 |
| Pab2 Light Chain FR4 | TTCGGTGCTGGGACCAAGCTGGAGCTGAAA | 34 |
| Pab2 Light Chain Variable Region | GATATTGTGATGACGCAGGCTGCATTCTCCAATCCAGTCAC<br>TCTTGGAACATCAGCTTCCATCTCCTGCAGGTC<br>TAGTAAGAGTCTCCTACATAGTAATGGCATCACTTATTTGT<br>ATTGGTATCTGCAGAAGCCAGGCCAGTCTCCTCAGCTCCTG<br>ATTTATCAGATGTCCAACCTTGCCTCAGGAGTCCCAGACAG<br>GTTCAGTAGCAGTGGGTCAGGAACTGATTTCACACTGAGA<br>ATCAGCAGAGTGGAGGCTGAGGATGTGGGTGTTTATTACT<br>GTGCTCAAAATCTAGAACTTCCGCTCACGTTCGGTGCTGGG<br>ACCAAGCTGGAGCTGAAA | 35 |
| Pab2 Light Chain Constant Region | CTGTGCTCAAAATCTAGAACTTCCGCTCACGTTCGGTGCTG<br>GGACCAAGCTGGAGCTGAAACGGGCTGATGCTGCACCAAC<br>TGTATCCATCTTCCCACCATCCAGTGAGCAGTTAACATCTG<br>GAGGTGCCTCAGTCGTGTGCTTCTTGAACAACTTCTACCCC<br>AAAGACATCAATGTCAAGTGGAAGATTGATGGCAGTGAAC<br>GACAAAATGGCGTCCTGAACAGTTGGACTGATCAGGACAG<br>CAAAGACAGCACCTACAGCATGAGCAGCACCCTCACGTTG<br>ACCAAGGACGAGTATGAACGACATAACAGCTATACCTGTG<br>AGGCCACTCACA<br>AGACATCAACTTCACCCATTGTCAAGAGCTTCAACAGGAAT<br>GAGTGT | 36 |
| Pab2 Light Chain | MRFSAQLLGLLVLWIPSTADIVMTQAAFSNPVTLGTSASISC<br>RSSKSLLHSNGITYLYWYLQKPGQSPQLLIYQMSNLASGVPDR<br>FSSSGSGTDFTLRISRVEAEDVGVYYCAQNLELPLTFGAGTKL<br>ELKRADAAPTVSIFPPSSEQLTSGGASVVCFLNNFYPKDINVK<br>WKIDGSERQNGVLNSWTDQDSKDSTYSMSSTLTLTKDEYER<br>HNSYTCEATHKTSTSPIVKSFNRNEC | 37 |
| Pab2 Light Chain Leader | MRFSAQLLGLLVLWIPSTA | 38 |
| Pab2 Light Chain FR1 | DIVMTQAAFSNPVTLGTSASISC | 39 |
| Pab2 Light Chain CDR1 | RSSKSLLHSNGITYLY | 40 |

| Name | Sequence | SEQ ID NO: |
|---|---|---|
| Pab2 Light Chain FR2 | WYLQKPGQSPQLLIY | 41 |
| Pab2 Light Chain CDR2 | QMSNLAS | 42 |
| Pab2 Light Chain FR3 | GVPDRFSSSGSGTDFTLRISRVEAEDVGVYYC | 43 |
| Pab2 Light Chain CDR3 | AQNLELPLT | 44 |
| Pab2 Light Chain FR4 | FGAGTKLELK | 45 |
| Pab2 Light Chain Variable Region | DIVMTQAAFSNPVTLGTSASISCRSSKSLLHSNGITYLYWYLQKPGQSPQLLIYQMSNLASGVPDRFSSSGSGTDFTLRISRVEAEDVGVYYCAQNLELPLTFGAGTKLELK | 46 |
| Pab2 Light Chain Constant Region | RADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC | 47 |

Pab1 Sequences

| Name | Sequence | SEQ ID NO: |
|---|---|---|
| Pab1 Heavy Chain | ATGGCTTGGGTGTGGACCTTGCTATTCCTGATGGCAGCTGCCCAAAGTATCCAAGCACAGATCCAGTTGGTGCAGTCTGGACCTGAGCTGAAGAAGCCTGGAGAGACAGTCAAGATCTCCTGCAAGGCTTCTGGTTATACCTTCACAGACTATTCAATGCACTGGGTGAAGCAGGCTCCAGGAAAGGGTTTAAAGTGGATGGGCTGGATAAACACTGAGACTGGTGAGCCAACATATGCAGATGACTTCAAGGGACGGTTTGCCTTCTCTTTGGAAACCTCTGCCAGCACTGCCTATTTGCAGATCAACAACCTCAAAAATGAGGACACGGCTACATATTTCTGTGCCCCGGAGGGTTTGCTTACTGGGGCAAGGGACTCTGGTCACTGTCTCTGCAGCCAAAACAACACCCCCATCAGTCTATCCACTGGCCCCTGGGTGTGGAGATACAACTGGTTCCTCCGTGACTCTGGGATGCCTGGTCAAGGGCTACTTCCCTGAGTCAGTGACTGTGACTTGGAACTCTGGATCCCTGTCCAGCAGTGTGCACACCTTCCCAGCTCTCCTGCAGTCTGGACTCTACACTATGAGCAGCTCAGTGACTGTCCCCTCCAGCACCTGGCCAAGTCAGACCGTCACCTGCAGCGTTGCTCACCCAGCCAGCAGCACCACGGTGGACAAAAAACTTGAGCCCAGCGGGCCCATTTCAACAATCAACCCCTGTCCTCCATGCAAGGAGTGTCACAAATGCCCAGCTCCTAACCTCGAGGGTGGACCATCCGTCTTCATCTTCCCTCCAAATATCAAGGATGTACTCATGATCTCCCTGACACCCAAGGTCACGTGTGTGGTGGTGGATGTGAGCGAGGATGACCCAGACGTCCAGATCAGCTGGTTTGTGAACAACGTGGAAGTACACACAGCTCAGACACAAACCCATAGAGAGGATTACAACAGTACTATCCGGGTGGTCAGCACCCTCCCCATCCAGCACCAGGACTGGATGAGTGGCAAGGAGTTCAAATGCAAGGTCAACAACAAAGACCTCCCATCACCCATCGAGAGAACCATCTCAAAAATTAAAGGGCTAGTCAGAGCTCCACAAGTATACATCTTGCCGCCACCAGCAGAGCAGTTGTCCAGGAAAGATGTCAGTCTCACTTGCCTGGTCGTGGGCTTCAACCCTGGAGACATCAGTGTGGAGTGGACCAGCAATGGGCATACAGAGGAGAACTACAAGGACACCGCACCAGTCCTGGACTCTGACGGTTCTTACTTCATATATAGCAAGCTCAATATGAAAACAAGCAAGTGGGAGAAAACAGATTCCTTCTCATGCAACGTGAGAACGAGGGTCTGAAAAATTACTACCTGAAGAAGACCATCTCCCGGTCTCCGGGTAAATGA | 48 |
| Pab1 Heavy Chain Leader | ATGGCTTGGGTGTGGACCTTGCTATTCCTGATGGCAGCTGCCCAAAGTATCCAAGCA | 49 |
| Pab1 Heavy Chain FR1 | CAGATCCAGTTGGTGCAGTCTGGACCTGAGCTGAAGAAGCCTGGAGAGACAGTCAAGATCTCCTGCAAGGCTTCTGGTTATACCTTCACA | 50 |

| Name | Sequence | SEQ ID NO: |
|---|---|---|
| Pab1 Heavy Chain CDR1 | GACTATTCAATGCAC | 51 |
| Pab1 Heavy Chain FR2 | TGGGTGAAGCAGGCTCCAGGAAAGGGTTTAAAGTGGATGGGC | 52 |
| Pab1 Heavy Chain CDR2 | TGGATAAACACTGAGACTGGTGAGCCAACATATGCAGATGACTTCAAGGGA | 53 |
| Pab1 Heavy Chain FR3 | CGGTTTGCCTTCTCTTTGGAAACCTCTGCCAGCACTGCCTATTTGCAGATCAACAACCTCAAAAATGAGGACACGGCTACATATTTCTGTGCCCCC | 54 |
| Pab1 Heavy Chain CDR3 | GGAGGGTTTGCTTAC | 55 |
| Pab2 Heavy Chain FR4 | TGGGGCCAAGGGACTCTGGTCACTGTCTCTGCA | 56 |
| Pab1 Heavy Chain Variable Region | CAGATCCAGTTGGTGCAGTCTGGACCTGAGCTGAAGAAGCCTGGAGAGACAGTCAAGATCTCCTGCAAGGCTTCTGGTTATACCTTCACAGACTATTCAATGCACTGGGTGAAGCAGGCTCCAGGAAAGGGTTTAAAGTGGATGGGCTGGATAAACACTGAGACTGGTGAGCCAACATATGCAGATGACTTCAAGGGACGGTTTGCCTTCTCTTTGGAAACCTCTGCCAGCACTGCCTATTTGCAGATCAACAACCTCAAAAATGAGGACACGGCTACATATTTCTGTGCCCCCGGAGGGTTTGCTTACTGGGGCCAAGGGACTCTGGTCACTGTCTCTGCA | 57 |
| Pab1 Heavy Chain Constant Region | GCCAAAACAACACCCCCATCAGTCTATCCACTGGCCCCTGGGTGTGGAGATACAACTGGTTCCTCCGTGACTCTGGGATGCCTGGTCAAGGGCTACTTCCCTGAGTCAGTGACTGTGACTTGGAACTCTGGATCCCTGTCCAGCAGTGTGCACACCTTCCCAGCTCTCCTGCAGTCTGGACTCTACACTATGAGCAGCTCAGTGACTGTCCCCTCCAGCACCTGGCCAAGTCAGACCGTCACCTGCAGCGTTGCTCACCCAGCCAGCAGCACCACGGTGGACAAAAAACTTGAGCCCAGCGGGCCCATTTCAACAATCAACCCCTGTCCTCCATGCAAGGAGTGTCACAAATGCCCAGCTCCTAACCTCGAGGGTGGACCATCCGTCTTCATCTTCCCTCCAAATATCAAGGATGTACTCATGATCTCCCTGACACCCAAGGTCACGTGTGTGGTGGTGGATGTGAGCGAGGATGACCCAGACGTCCAGATCAGCTGGTTTGTGAACAACGTGGAAGTACACACAGCTCAGACACAAACCCATAGAGAGGATTACAACAGTACTATCCGGGTGGTCAGCACCCTCCCCATCCAGCACCAGGACTGGATGAGTGGCAAGGAGTTCAAATGCAAGGTCAACAACAAAGACCTCCCATCACCCATCGAGAGAACCATCTCTAAAAATTAAAGGGCTAGTCAGAGCTCCACAAGTATACATCTTGCCGCCACCAGCAGAGCAGTTGTCCAGGAAAGATGTCAGTCTCACTTGCCTGGTCGTGGGCTTCAACCCTGGAGACATCAGTGTGGAGTGGACCAGCAATGGGCATACAGAGGAGAACTACAAGGACACCGCACCAGTCCTGGACTCTGACGGTTCTTACTTCATATATAGCAAGCTCAATATGAAAACAAGCAAGTGGGAGAAAACAGATTCCTTCTCATGCAACGTGAGACACGAGGGTCTGAAAAATTACTACCTGAAGAAGACCATCTCCCGGTCTCCGGGTAAA | 58 |
| Pab1 Heavy Chain | MAWVWTLLFLMAAAQSIQAQIQLVQSGPELKKPGETVKISCKASGYTFTDYSMHWVKQAPGKGLKWMGWINTETGEPTYADDFKGRFAFSLETSASTAYLQINNLKNEDTATYFCAPGGFAYWGQGTLVTVSAAKTTPPSVYPLAPGCGDTTGSSVTLGCLVKGYFPESVTVTWNSGSLSSSVHTFPALLQSGLYTMSSSVTVPSSTWPSQTVTCSVAHPASSTTVDKKLEPSGPISTINPCPPCKECHKCPAPNLEGGPSVFIFPPNIKDVLMISLTPKVTCVVVDVSEDDPDVQISWFVNNVEVHTAQTQTHREDYNSTIRVVSTLPIQHQDWMSGKEFKCKVNNKDLPSPIERTISKIKGLVRAPQVYILPPPAEQLSRKDVSLTCLVVGFNPGDISVEWTSNGHTEENYKDTAPVLDSDGSYFIYSKLNMKTSKWEKTDSFSCNVRHEGLKNYYLKKTISRSPGK | 59 |
| Pab1 Heavy Chain Leader | MAWVWTLLFLMAAAQSIQA | 60 |

| Name | Sequence | SEQ ID NO: |
|---|---|---|
| Pab1 Heavy Chain FR1 | QIQLVQSGPELKKPGETVKISCKASGYTFT | 61 |
| Pab1 Heavy Chain CDR1 | DYSMH | 62 |
| Pab1 Heavy Chain FR2 | WVKQAPGKGLKWMG | 63 |
| Pab1 Heavy Chain CDR2 | WINTETGEPTYADDFKG | 64 |
| Pab1 Heavy Chain FR3 | RFAFSLETSASTAYLQINNLKNEDTATYFCAP | 65 |
| PAb1 Heavy Chain CDR3 | GGFAY | 66 |
| PAb1 Heavy Chain FR4 | WGQGTLVTVSA | 67 |
| PAb1 Heavy Chain Variable Region | QIQLVQSGPELKKPGETVKISCKASGYTFTDYSMHWVKQAPGKGLKWMGWINTETGEPTYADDFKGRFAFSLETSASTAYLQINNLKNEDTATYFCAPGGFAYWGQGTLVTVSA | 68 |
| PAb1 Heavy Chain Constant Region | AKTTPPSVYPLAPGCGDTTGSSVTLGCLVKGYFPESVTVTWNSGSLSSSVHTFPALLQSGLYTMSSSVTVPSSTWPSQTVTCSVAHPASSTTVDKKLEPSGPISTINPCPPCKECHKCPAPNLEGGPSVFIFPPNIKDVLMISLTPKVTCVVVDVSEDDPDVQISWFVNNVEVHTAQTQTHREDYNSTIRVVSTLPIQHQDWMSGKEFKCKVNNKDLPSPIERTISKIKGLVRAPQVYILPPPAEQLSRKDVSLTCLVVGFNPGDISVEWTSNGHTEENYKDTAPVLDSDGSYFIYSKLNMKTSKWEKTDSFSCNVRHEGLKNYYLKKTISRSPGK | 69 |
| PAb1 Light Chain | ATGAGGTGCCTAGCTGAGTTCCTGGGGCTGCTTGTGCTCTGGATCCCTGGAGCCATTGGGATATTGTGATGACTCAGGCTGCACCCTCTGTACCTGTCACTCCTGGAGAGTCAGTATCCATCTCCTGCAGGTCTAGTAAGAGTCTCCTGCATAGTAATGGCAACACTTACTTGTATTGGTTCCTGCAGAGGCCAGGCCAGTCTCCTCAGCTCCTGATATATCGGATGTCCAACCTTGCCTCAGGAGTCCCAGACAGGTTCAGTGGCAGTGGGTCAGGAACTGCTTTCACACTGAGAATCAGTAGAGTGGAGGCTGAGGATGTGGGTGTTTATTACTGTATGCAACATCTAGAATATCCGCTCACGTTCGGTGCTGGGACCAAGCTGGAGCTGAAACGGGCTGATGCTGCACCAACTGTATCCATCTTCCCACCATCCAGTGAGCAGTTAACATCTGGAGGTGCCTCAGTCGTGTGCTTCTTGAACAACTTCTACCCCAAAGACATCAATGTCAAGTGGAAGATTGATGGCAGTGAACGACAAAATGGCGTCCTGAACAGTTGGACTGATCAGGACAGCAAAGACAGCACCTACAGCATGAGCAGCACCCTCACGTTGACCAAGGACGAGTATGAACGACATAACAGCTATACCTGTGAGGCCACTCACAAGACATCAACTTCACCCATTGTCAAGAGCTTCAACAGGAATGAGTGTTAG | 70 |
| PAb1 Light Chain Leader | ATGAGGTGCCTAGCTGAGTTCCTGGGGCTGCTTGTGCTCTGGATCCCTGGAGCCATTGGG | 71 |
| PAb1 Light Chain FR1 | GATATTGTGATGACTCAGGCTGCACCCTCTGTACCTGTCACTCCTGGAGAGTCAGTATCCATCTCCTGC | 72 |
| PAb1 Light Chain CDR1 | AGGTCTAGTAAGAGTCTCCTGCATAGTAATGGCAACACTTACTTGTAT | 73 |
| PAb1 Light Chain FR2 | TGGTTCCTGCAGAGGCCAGGCCAGTCTCCTCAGCTCCTGATATAT | 74 |
| PAb1 Light Chain CDR2 | CGGATGTCCAACCTTGCCTCA | 75 |
| PAb1 Light Chain FR3 | GGAGTCCCAGACAGGTTCAGTGGCAGTGGGTCAGGAACTGCTTTCACACTGAGAATCAGTAGAGTGGAGGCTGAGGATGTGGGTGTTTATTACTGT | 76 |
| PAb1 Light Chain CDR3 | ATGCAACATCTAGAATATCCGCTCACG | 77 |

| Name | Sequence | SEQ ID NO: |
|---|---|---|
| PAb1 Light Chain FR4 | TTCGGTGCTGGGACCAAGCTGGAGCTGAAA | 78 |
| PAb1 Light Chain Variable Region | GATATTGTGATGACTCAGGCTGCACCCTCTGTACCTGTCAC TCCTGGAGAGTCAGTATCCATCTCCTGCAGGTCTAGTAAGA GTCTCCTGCATAGTAATGGCAACACTTACTTGTATTGGTTC CTGCAGAGGCCAGGCCAGTCTCCTCAGCTCCTGATATATCG GATGTCCAACCTTGCCTCAGGAGTCCCAGACAGGTTCAGTG GCAGTGGGTCAGGAACTGCTTTCACACTGAGAATCAGTAG AGTGGAGGCTGAGGATGTGGGTGTTTATTACTGTATGCAAC ATCTAGAATATCCGCTCACGTTCGGTGCTGGGACCAAGCTG GAGCTGAAA | 79 |
| PAb1 Light Chain Constant Region | CGGGCTGATGCTGCACCAACTGTATCCATCTTCCCACCATC CAGTGAGCAGTTAACATCTGGAGGTGCCTCAGTCGTGTGCT TCTTGAACAACTTCTACCCCAAAGACATCAATGTCAAGTGG AAGATTGATGGCAGTGAACGACAAAATGGCGTCCTGAACA GTTGGACTGATCAGGACAGCAAAGACAGCACCTACAGCAT GAGCAGCACCCTCACGTTGACCAAGGACGAGTATGAACGA CATAACAGCTATACCTGTGAGGCCACTCACAAGACATCAA CTTCACCCATTGTCAAGAGCTTCAACAGGAATGAGTGT | 80 |
| PAb1 Light Chain | MRCLAEFLGLLVLWIPGAIGDIVMTQAAPSVPVTPGESVSISC RSSKSLLHSNGNTYLYWFLQRPGQSPQLLIYRMSNLASGVPD RFSGSGSGTAFTLRISRVEAEDVGVYYCMQHLEYPLTFGAGT KLELKRADAAPTVSIFPPSSEQLTSGGASVVCFLNNFYPKDINV KWKIDGSERQNGVLNSWTDQDSKDSTYSMSSTLTLTKDEYE RHNSYTCEATHKTSTSPIVKSFNRNEC | 81 |
| PAb1 Light Chain Leader | MRCLAEFLGLLVLWIPGAIG | 82 |
| PAb1 Light Chain FR1 | DIVMTQAAPSVPVTPGESVSISC | 83 |
| PAb1 Light Chain CDR1 | RSSKSLLHSNGNTYLY | 84 |
| PAb1 Light Chain FR2 | WFLQRPGQSPQLLIY | 85 |
| PAb1 Light Chain CDR2 | RMSNLAS | 86 |
| PAb1 Light Chain FR3 | GVPDRFSGSGSGTAFTLRISRVEAEDVGVYYC | 87 |
| PAb1 Light Chain CDR3 | MQHLEYPLT | 88 |
| PAb1 Light Chain FR4 | FGAGTKLELKR | 89 |
| PAb1 Light Chain Variable Region | DIVMTQAAPSVPVTPGESVSISCRSSKSLLHSNGNTYLYWFLQ RPGQSPQLLIYRMSNLASGVPDRFSGSGSGTAFTLRISRVEAED VGVYYCMQHLEYPLTFGAGTKLELKR | 90 |
| PAb1 Light Chain Constant Region | ADAAPTVSIFPPSSEQLTSGGASVVCFLNNFYPKDINVKWKID GSERQNGVLNSWTDQDSKDSTYSMSSTLTLTKDEYERHNSYT CEATHKTSTSPIVKSFNRNEC | 91 |

-Plectin (hemidesmosomal protein 1), Homo sapiens; target protein underlined

>SEQ ID NO: 92
SSSDGVVKSMIIDRRSGRQYDIDDAIAKNLIDRSALDQYRAGTLSITEFA
DMLSGNAGGFRSRSSSVGSSSSYPISPAVSRTQLASWSDPTEETGPVAGI
LDTETLEKVSITEAMHRNLVDNITGQRLLEAQACTGGIIDPSTGERFPVT
DAVNKGLVDKIMVDRINLAQKAFCGFEDPRTKTKMSAAQALKKGWLYYEA
GQRFLEVQYLTGGLIEPDTPGRVPLDEALQRGTVDARTAQKLRDVGAYSK
YLTCPKTKLKISYKDALDRSMVEEGTGLRLLEAAAQSTKGYYSPYSVSGS
GSTAGSRTGSRTGSRAGSRRGSFDATGSGFSMTFSSSSYSSSGYGRRYAS
GSSASLGGPESAVA

The invention claimed is:

1. An antibody or antigen binding fragment thereof that specifically binds to a cell-surface exposed plectin-1 antigen, wherein the antibody or antigen binding fragment thereof comprises a heavy chain variable region having a sequence set forth as: SEQ ID NO: 24 and a light chain variable region having a sequence set forth as: SEQ ID NO: 46; or a heavy chain variable region having a sequence set forth as: SEQ ID NO: 68 and a light chain variable region having a sequence set forth as: SEQ ID NO: 90.

2. The antibody of claim 1, wherein the antibody or antigen binding fragment thereof comprises a heavy chain variable region having a sequence set forth as: SEQ ID NO: 24 and a light chain variable region having a sequence set forth as: SEQ ID NO: 46.

3. The antibody of claim 1, wherein the antibody or antigen binding fragment thereof comprises a heavy chain variable region having a sequence set forth as: SEQ ID NO: 68 and a light chain variable region having a sequence set forth as: SEQ ID NO: 90.

4. The antibody of claim 1, wherein the antibody is coupled to a targeted agent.

5. An antibody, or antigen binding fragment thereof, that specifically binds to cell-surface exposed plectin-1 antigen, and that comprises six complementarity determining regions (CDRs): CDRH1, CDRH2, CDRH3, CDRL1, CDRL2, and CDRL3,
wherein CDRH1 comprises a sequence as set forth in SEQ ID NO: 18, CDRH2 comprises a sequence as set forth in SEQ ID NO: 20, CDRH3 comprises a sequence as set forth in SEQ ID NO:22, CDRL1 comprises a sequence as set forth in SEQ ID NO: 40, CDRL2 comprises a sequence as set forth in SEQ ID NO: 42, and CDRL3 comprises a sequence as set forth in SEQ ID NO: 44; or
wherein CDRH1 comprises a sequence as set forth in SEQ ID NO: 62, CDRH2 comprises a sequence as set forth in SEQ ID NO: 64, CDRH3 comprises a sequence as set forth in SEQ ID NO: 66, CDRL1 comprises a sequence as set forth in SEQ ID NO: 84, CDRL2 comprises a sequence as set forth in SEQ ID NO: 86, and CDRL3 comprises a sequence as set forth in SEQ ID NO: 88.

6. The antibody or antigen binding fragment thereof of claim 5, wherein the antibody or antigen binding fragment thereof comprises
a heavy chain variable region having a sequence with at least 85% identity to SEQ ID NO: 24 and a light chain variable region with at least 85% identity to SEQ ID NO: 46; or
a heavy chain variable region having a sequence with at least 85% identity to SEQ ID NO: 68 and a light chain variable region with at least 85% identity to SEQ ID NO: 90.

7. The antibody or antigen binding fragment thereof of claim 5, wherein the antibody or antigen binding fragment thereof is coupled to a targeted agent.

8. A composition comprising the antibody or antigen binding fragment thereof of claim 5, optionally further comprising a pharmaceutically acceptable excipient.

9. A method for treating cancer, the method comprising administering to a subject having cancer an effective amount of an antibody or antigen binding fragment thereof of claim 1, wherein the cancer is characterized by surface expression of plectin-1 and is selected from the group consisting of pancreatic cancer, ovarian cancer, esophageal cancer, prostate cancer, lung cancer, and head and neck squamous cell carcinoma.

10. A method for detecting a cancer cell, the method comprising contacting a cancer cell in vitro with the antibody or antigen binding fragment thereof of claim 5.

* * * * *